United States Patent
Carlsen et al.

(10) Patent No.: US 6,849,618 B2
(45) Date of Patent: *Feb. 1, 2005

(54) URACIL SUBSTITUTED PHENYL SULFAMOLY CARBOXAMIDES

(75) Inventors: Marianne Carlsen, Yardley, PA (US); Michael Anthony Guaciaro, Hightstown, NJ (US); James Jan Takasugi, Lawrenceville, NJ (US)

(73) Assignee: BASF Aktiengesellschaft, Ludwigshafen (DE)

(*) Notice: Subject to any disclaimer, the term of this patent is extended or adjusted under 35 U.S.C. 154(b) by 2 days.

This patent is subject to a terminal disclaimer.

(21) Appl. No.: 10/684,940

(22) Filed: Oct. 15, 2003

(65) Prior Publication Data

US 2004/0220172 A1 Nov. 4, 2004

Related U.S. Application Data

(62) Division of application No. 10/347,920, filed on Jan. 22, 2003, now Pat. No. 6,689,773, which is a division of application No. 09/848,881, filed on May 4, 2001, now Pat. No. 6,534,492.
(60) Provisional application No. 60/201,824, filed on May 4, 2000.

(51) Int. Cl.$^7$ .................. A61K 31/33; A61K 31/415; A61K 31/41; C07D 257/00; C07D 249/08
(52) U.S. Cl. .................. 514/183; 514/277; 514/385; 514/381; 514/408; 546/1; 546/290; 546/329; 548/250; 548/262.2; 548/300.1
(58) Field of Search .................. 514/183, 277, 514/385, 381, 408; 546/1, 290, 329; 548/250, 262.2, 300.1

(56) References Cited

U.S. PATENT DOCUMENTS

| | | | |
|---|---|---|---|
| 4,746,352 A | 5/1988 | Wenger et al. | 71/90 |
| 4,760,163 A | 7/1988 | Wenger et al. | 560/34 |
| 4,812,164 A * | 3/1989 | Wenger et al. | 504/243 |
| 4,859,229 A | 8/1989 | Wenger et al. | 71/92 |
| 5,484,763 A | 1/1996 | Wepplo | 548/207 |
| 5,523,278 A | 6/1996 | Wepplo | 504/271 |
| 6,077,813 A | 6/2000 | Linker et al. | 504/272 |
| 6,534,492 B2 * | 3/2003 | Carlsen et al. | 514/183 |
| 6,689,773 B2 * | 2/2004 | Carlsen et al. | 514/183 |

FOREIGN PATENT DOCUMENTS

| | | |
|---|---|---|
| DE | 44 37 197 | 4/1996 |
| DE | 196 10 786 | 9/1997 |
| DE | 196 27 901 | 1/1998 |
| DE | 196 32 005 | 2/1998 |
| DE | 197 31 784 | 2/1999 |
| EP | 464900 * | 1/1992 |
| WO | 96/08151 | 3/1996 |

OTHER PUBLICATIONS

Santel et al., Derwent Abstract 96–210261/22, and esp@cwnet abstract of DE 44 37 197.

* cited by examiner

Primary Examiner—Richard L. Raymond
Assistant Examiner—Sudhaker B. Patel
(74) Attorney, Agent, or Firm—Keil & Weinkauf

(57) ABSTRACT

Novel uracil substituted phenyl sulfamoyl carboxamides I

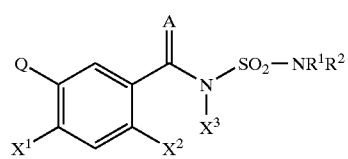

and salts thereof, where
A=oxygen or sulfur;
$X^1$=H, halogen, $C_1$–$C_4$-alkyl;
$X^2$=H, CN, CS—$NH_2$, halogen, $C_1$–$C_4$-alkyl, $C_1$–$C_4$-haloalkyl;
$X^3$=H, CN, $C_1$–$C_6$-alkyl, $C_1$–$C_6$-alkoxyalkyl, $C_3$–$C_7$-cycloalkyl, $C_3$–$C_6$-alkenyl, $C_3$–$C_6$-alkynyl, optionally substituted benzyl;
$R^1$, $R^2$=H, halogen, optionally substituted hydroxy, $C_1$–$C_{10}$-alkyl, $C_2$–$C_{10}$-alkenyl, $C_3$–$C_{10}$-alkynyl, $C_3$–$C_7$-cycloalkyl, phenyl, benzyl or $C_5$–$C_7$-cycloalkenyl, or $R^1$+$R^2$ together with the atom to which they are attached form a 3- to 7-membered heterocyclic ring;
Q is selected from $Q^1$ to $Q^{40}$ as defined in the description.

Use: As herbicides; for the desiccation/defoliation of plants.

14 Claims, No Drawings

URACIL SUBSTITUTED PHENYL SULFAMOLY CARBOXAMIDES

This application is a divisional of U.S. application Ser. No. 10/347,920, filed on Jan. 22, 2003, now U.S. Pat. No. 6,689,773 (allowed), the entire disclosure of which is herewith incorporated by reference, which is a divisional of U.S. application Ser. No. 09/848,881, filed on May 4, 2001, (now U.S. Pat. No. 6,534,492), the entire disclosure of which is here-with incorporated by reference, which claims the benefit of U.S. Provisional Application No. 60/201,824, filed on May 4, 2000, the entire disclosure of which is herewith incorporated by reference.

Weeds cause tremendous global economic losses by reducing crop yields and lowering crop quality. Worldwide, agronomic crops must compete with hundreds of weed species.

In spite of the commercial herbicides available today, damage to crops caused by weeds still occurs. Accordingly, there is ongoing research to create more effective and/or more selective herbicidal agents.

In WO 98/06706 are disclosed the use of certain p-trifluoro-methylphenyl uracils, their method of production and their use as herbicides. In addition, WO 96/08151 discloses herbicidal aryl uracils and arylthiouracils in which the aryl ring is an optionally substituted phenyl group. In neither disclosure, however is there mentioned a sulfamoyl carboxamide group substituent.

Therefore, it was an object of the present invention to provide novel 3-phenyluracils which are highly effective fox the control of undesirable plant species. The object also extends to providing novel compounds which act as desiccants/defoliants.

It was also an object of the present invention to provide a method for the control of undesirable plant species and compositions useful therefor.

It is an advantage of the present invention that the method for the control of undesirable plant species may be employed in the presence of a crop.

It was a further object of the present invention to provide a process for the preparation of herbicidal phenylsulfamoyl carboxamides and an intermediate compound useful therefor.

These and other objects and advantages of the present invention will become more apparent from the detailed description thereof set forth below.

We have found that this object is achieved in accordance with the invention by the novel uracil substituted phenylsulfamoyl carboxamides of the formula I $$\text{Q} \underset{X^1}{\overset{A}{\diagdown}} \text{SO}_2-NR^1R^2,$$

I wherein the variables have the following meanings:
A oxygen or sulfur;
$X^1$ hydrogen, halogen or $C_1$–$C_4$-alkyl;
$X^2$ hydrogen, cyano, CS—NH$_2$, halogen, $C_1$–$C_4$-alkyl or $C_1$–$C_4$-haloalkyl;
$X^3$ hydrogen, cyano, $C_1$–$C_6$-alkyl, $C_1$–$C_6$-alkoxy-alkyl, $C_3$–$C_7$-cycloalkyl, $C_3$–$C_6$-alkenyl, $C_3$–$C_6$-alkynyl or optionally substituted benzyl;
$R^1$ and $R^2$ independently of one another
hydrogen, halogen, $OR^{48}$, $C_1$–$C_{10}$-alkyl, $C_2$–$C_{10}$-alkenyl, $C_3$–$C_{11}$-alkynyl, $C_3$–$C_7$-cycloalkyl, phenyl, benzyl or $C_5$–$C_7$-cycloalkenyl, whereas each of the last-mentioned 7 groups can be substituted with any combination of one to six halogen atoms, one to three $C_1$–$C_6$-alkoxy groups, one or two $C_1$–$C_8$-haloalkoxy groups, one or two cyano groups, one or two $C_3$–$C_7$-cycloalkyl groups, one or two $C(O)R^{49}$ groups, one or two CO—$OR^{50}$ groups, one or two CO—$SR^{51}$ groups, one or two CO—$NR^{52}R^{53}$ groups, one to three $OR^{54}$ groups, one to three $SR^{54}$ groups, one optionally substituted four to 10-membered monocyclic or fused bicyclic heterocyclic ring, one or two optionally substituted phenyl groups or one or two optionally substituted benzyl groups,
or $R^1$ and $R^2$ together with the atom to which they are attached form a 3- to 7-membered heterocyclic ring;
Q is selceted from -continued
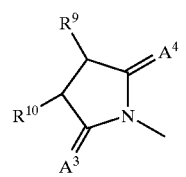 Q⁸
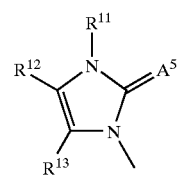 Q⁹
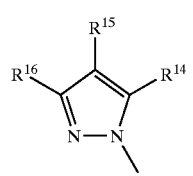 Q¹⁰
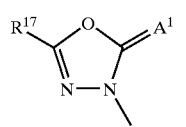 Q¹¹
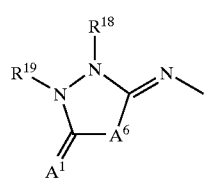 Q¹²
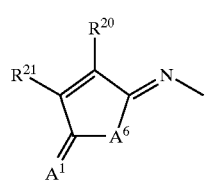 Q¹³
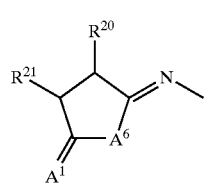 Q¹⁴
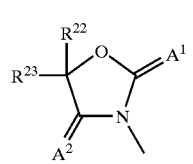 Q¹⁵
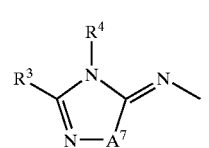 Q¹⁶
-continued
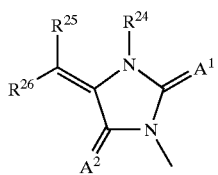 Q¹⁷
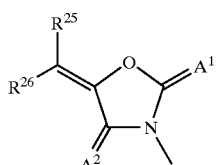 Q¹⁸
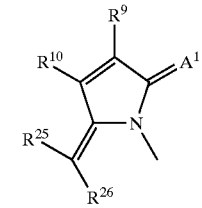 Q¹⁹
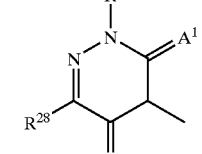 Q²⁰
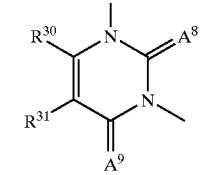 Q²¹
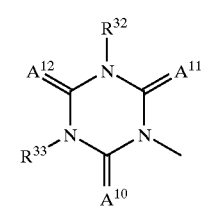 Q²²
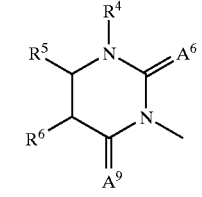 Q²³
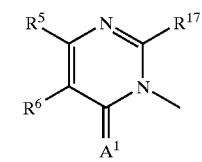 Q²⁴

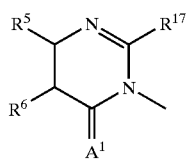 Q25

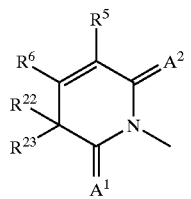 Q26

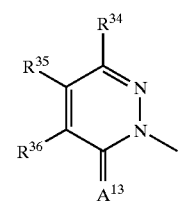 Q27

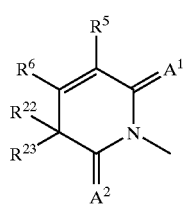 Q28

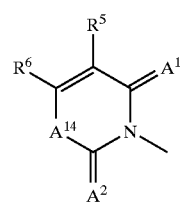 Q29

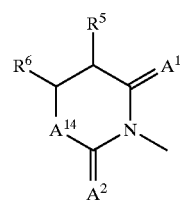 Q30

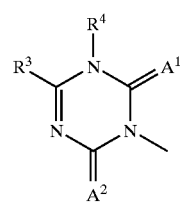 Q31

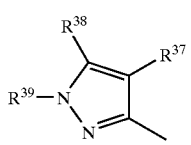 Q32

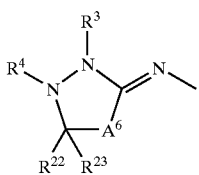 Q33

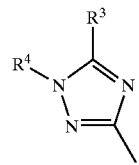 Q34

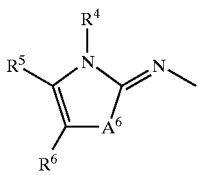 Q35

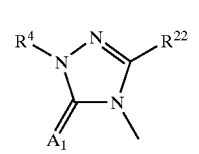 Q36

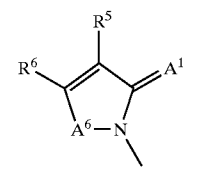 Q37

Q38

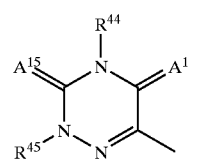 Q39

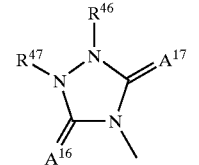 Q40 wherein $A^1$ to $A^{17}$ are each independently oxygen or sulfur;

$R^3$, $R^4$, $R^7$, $R^8$, $R^{11}$, $R^{12}$, $R^{18}$, $R^{19}$, $R^{27}$, $R^{29}$, $R^{32}$, $R^{33}$, $R^{38}$, $R^{39}$, $R^{44}$, $R^{45}$, $R^{46}$ and $R^{47}$ are each independently
hydrogen, cyano, amino, $C_1$–$C_6$-alkyl, $C_1$–$C_6$-haloalkyl, $C_1$–$C_6$-haloalkoxy, $C_3$–$C_7$-cycloalkyl, $C_2$–$C_6$-alkenyl, $C_2$–$C_6$-haloalkenyl, $C_3$–$C_6$-alkynyl, benzyl, $OR^{55}$, $C_1$–$C_3$-cyanoalkyl, or $R^3$ and $R^4$, $R^7$ and $R^8$, $R^{11}$ and $R^{12}$, $R^{18}$ and $R^{19}$ or $R^{46}$ and $R^{47}$ may be taken together with the atoms to which they are attached to represent a four- to seven-membered ring, optionally interrupted by oxygen, sulfur or nitrogen and optionally substituted with one or sore halogen or $C_2$–$C_4$-alkyl groups;

$R^5$, $R^6$, $R^9$, $R^{10}$, $R^{15}$, $R^{16}$, $R^{20}$, $R^{21}$, $R^{30}$, $R^{33}$, $R^{35}$, $R^{36}$, $R^{41}$, $R^{42}$ and $R^{43}$ are each independently hydrogen, $C_1$–$C_6$-alkyl, $C_1$–$C_6$-haloalkyl, $C_3$–$C_7$-cycloalkyl, $C_2$–$C_6$-alkenyl, $C_2$–$C_6$-haloalkenyl, $C_3$–$C_6$-alkynyl, $OR^{56}$, $S(O)_nR^{57}$, $O$—$SO_2$—$R^{57}$, $NR^{58}R^{59}$ or $R^5$ and $R^6$, $R^9$ and $R^{10}$, $R^{15}$ and $R^{16}$, $R^{20}$ and $R^{21}$ or $R^{30}$ and $R^{31}$ may be taken together with the atoms to which they are attached to represent a four- to seven membered zing optionally substituted with one or more halogen or $C_1$–$C_4$-alkyl groups;

$R^{13}$, $R^{14}$, $R^{22}$, $R^{23}$, $R^{25}$ and $R^{26}$ are each independently hydrogen, halogen or $C_1$–$C_6$-alkyl;

$R^{17}$, $R^{28}$, $R^{34}$, $R^{37}$ or $R^{40}$ are each independently hydrogen, halogen, $C_1$–$C_6$-alkyl, $C_1$–$C_6$-haloalkyl, $C_3$–$C_7$-cycloalkyl, $C_2$–$C_6$-alkenyl, $C_2$–$C_6$-haloalkenyl, $C_3$–$C_6$-alkynyl, $OR^{60}$ or $SR^{61}$;

$R^{24}$ is hydrogen, $C_1$–$C_4$-alkyl, $C_1$–$C_4$-haloalkyl, $C_2$–$C_4$-alkenyl, $C_3$–$C_4$-alkynyl, $C_1$–$C_4$-haloalkoxy or amino;

$R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$ and $R^{61}$ are independently of one another hydrogen, $C_1$–$C_6$-alkyl, $C_1$–$C_6$-haloalkyl, $C_3$–$C_7$-cycloalkyl, $C_2$–$C_6$-alkenyl, $C_3$–$C_6$-alkynyl, optionally substituted phenyl or optionally substituted benzyl;

n is zero, 1 or 2;

and the agriculturally useful salts of the compounds I.

Furthermore, the invention relates to the use of the compounds I as herbicides and/or for the desiccation/defoliation of plants, herbicidal compositions and compositions for the desiccation/defoliation of plants which comprise compounds I as active substances, processes for preparing the compounds I and herbicidal compositions and compositions for the desiccation/defoliation of plants using the compounds I, methods for controlling undesirable vegetation and for the desiccation/defoliation of plants using the compounds I, and novel intermediates of the formula II.

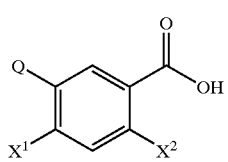

(II)

wherein Q, $X^1$ and $X^2$ are as defined hereinabove, with the proviso that Q must be other than $Q^{21}$.

Preferred compounds of the formulae I and II can be seen from the sub-claims and from the description which follows.

Depending on the substitution pattern, the compounds of the formula I can contain one or more chiral centers, in which case they exist in the form of enantiomer or diastereomer mixtures. This invention provides both the pure enantiomers or diasteromers and mixtures thereof.

Agriculturally useful salts are in particular the salts of those cations and the acid addition salts of those acids whose cations and anions, respectively, do not adversely affect the herbicidal activity of the compounds I. Suitable cations are therefore in particular the ions of the alkali metals, preferably sodium and potassium, of the alkaline earth metals, preferably calcium, magnesium and barium, and of the transition metals, preferably manganese, copper, zinc and iron, and the ammonium ion, which may carry one to four $C_1$–$C_4$-alkyl substituents, and/or one phenyl or benzyl substituent, preferably diisopropylammonium, tetramethylammonium, tetrabutylammonium, trimethylbenzylammonium, and furthermore phosphonium ions, sulfonium ions, preferably tri($C_1$–$C_4$-alkyl)sulfonium and sulfoxonium ions, preferably tri($C_1$–$C_4$-alkyl) sulfoxonium.

Anions of useful acid addition salts are primarily chloride, bromide, fluoride, hydrogensulfate, sulfate, dihydrogenphosphate, hydrogenphosphate, phosphate, nitrate, hydrogencarbonate, carbonate, hexafluorosilicate, hexafluorophosphate, benzoate, and the anions of $C_1$–$C_4$-alkanoic acids, preferably formate, acetate, propionate and butyrate.

The organic moieties mentioned for the substituents $X^3$ and $R^1$ to $R^{61}$ or as radicals on phenyl or heterocyclic rings are collective terms for individual enumerations of each of the group members, as is the meaning halogen. All carbon chains, ie. all alkyl, haloalkyl, alkenyl, alkynyl and phenylalkyl moieties can be straight-chain or branched.

The terms haloalkyl, haloalkoxy and haloalkenyl as used in the specification and claims designate an alkyl group, an alkoxy group or an alkenyl group substituted with one or more halogen atoms, respectively. The halogen atoms may be the same or different.

Halogenated substituents preferably have attached to them one to five identical or different halogen atoms.

In formula I above, 4- to 10-membered monocyclic or fused bicyclic, heterocyclic rings include, but are not limited to, benzimidazole, imidazole, imidazoline-2-thione, indole, isatoic anhydride, morpholine, piperazine, piperidine, purine, pyrazole, pyrrole, pyrrolidine and 1,2,4-triazole rings, wherein each ring is optionally substituted with one or more groups independently selected from halogen, cyano, nitro, amino, hydroxyl, $C_1$–$C_4$-alkyl, $C_1$–$C_4$-haloalkyl, $C_1$–$C_4$-alkoxy, $C^1$–$C_4$-haloalkoxy or $C_1$–$C_4$-haloalkylsulfonyl groups.

When the terms phenyl or benzyl are designated as being optionally substituted, the substituents which are optionally present may be any one or more of those customarily employed in the development of pesticidal compounds and/or the modification of such compounds to influence their structure/activity, persistence, penetration or other property. Specific examples of such substituents include, for example, halogen atoms, nitro, cyano, thiocyanato, cyanato, hydroxyl, alkyl, haloalkyl, alkoxy, haloalkoxy, amino, alkylamino, dialkylamino, formyl, alkoxy-carbonyl, carboxyl, alkanoyl, alkylthio, alkylsulphinyl, alkyl-sulfonyl, carbamoyl, alkylamido, phenyl, phenoxy, benzyl, benzyl-oxy, heterocyclyl, especially furyl, and cycloalkyl, expecially cyclopropyl, groups. Typically, zero to three substituents may be present. When any of the foregoing substituents represents or contains an alkyl substituent group, this may be linear or branched and may contain up to 12, preferably up to 6, and especially up to 4 carbon atoms.

In formula I above, 3- to 7-membered heterocyclic rings include, but are not limited to, imidazole and phthalimide rings wherein each ring is optionally substituted with any combination of one to three halogen atoms, one to three $C_1$–$C_4$-alkyl groups, one to three $C_1$–$C_4$-haloalkyl groups, one to three $C_1$–$C_4$-alkoxy groups, or one to three $C_1$–$C_4$-haloalkoxy groups.

The uracil substituted phenyl sulfamoyl carboxamides I possess an unexpected level of herbicidal activity and surprising crop selectivity.

Examples of individual meanings are:

halogen: fluorine, chlorine, bromine or iodine, preferably fluorine or chlorine;

$C_1$–$C_4$-alkyl; $CH_3$, $C_2H_5$, $CH_2$—$C_2H_5$, $CH(CH_3)_2$, n-$C_4H_9$, $CH(CH_3)$—$C_2H_5$, $CH_2$—$CH(CH_3)_2$ or $C(CH_3)_3$;

$C_1$–$C_6$-alkyl and the alkyl moiety of $C_1$–$C_6$-alkoxy-$C_1$–$C_6$-alkyl: methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably $C_1$–$C_4$-alkyl, in particular methyl or ethyl;

$C_1$–$C_3$-cyanoalkyl: $CH_2CN$, 1-cyanoethyl, 2-cyanoethyl, 1-cyanoprop-1-yl, 2-cyanoprop-1-yl, 3-cyanoprop-1-yl or 1-($CH_2CN$)eth-1-yl;

$C_1$–$C_6$-haloalkyl: $C_1$–$C_6$-alkyl as mentioned above which is partially or fully substituted by fluorine, chlorine, bromine and/or iodine, eg. $CH_2F$, $CHF_2$, $CF_3$, $CH_2Cl$, $CH(Cl)_2$, $C(Cl)_3$, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, $C_2F_5$, 3-fluoropropyl, 3-chloropropyl or $CF_2$—$C_2F_5$, preferably $C_1$–$C_4$-haloalkyl, in particular trifluoromethyl or 1,2-dichloroethyl;

$C_2$–$C_6$-alkenyl: ethenyl, prep-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methybut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-on-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl, preferably $C_3$- or $C_4$-alkenyl;

$C_2$–$C_6$-haloalkenyl: $C_2$–$C_6$-alkenyl as mentioned above which is partially or fully substituted by fluorine, chlorine, bromine and/or iodine, ie. for example 2-chloroallyl, 3-chloroallyl, 2,3-dichloroallyl, 3,3-dichloroallyl, 2,3,4-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl;

$C_3$–$C_6$-alkynyl: prop-1-yn-1-yl, prop-2-yn-3-yl, n-but-1-yn-1-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-1-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl, preferably $C_3$- or $C_4$-alkynyl, in particular prop-2-yn-3-yl;

phenyl-$C_1$–$C_5$-alkyl: for example benzyl, 1-phenyleth-1-yl, 2-phenyleth-1-yl, 1-phenylprop-1-yl, 2-phenylprop-1-yl, 3-phenylprop-1-yl, 1-phenylprop-2-yl, 2-phenylprop-2-yl, 1-phenylbut-1-yl, 2-phenylbut-1-yl, 3-phenylbut-1-yl, 4-phenylbut-1-yl, 1-phenylbut-2-yl, 2-phenylbut-2-yl, 1-phenylbut-3-yl, 2-phenylbut-3-yl, 1-phenyl-2-methylprop-3-yl, 2-phenyl-2-methylprop-3-yl, 3-phenyl-2-methylprop-3-yl or 2-benzylprop-2-yl, preferably phenyl-$C_1$–$C_4$-alkyl, in particular 2-phenyleth-1-yl;

$C_1$–$C_6$-alkoxy and the alkoxy moiety of $C_1$–$C_6$-Alkoxy-$C_1$–$C_6$-alkyl: methoxy, ethoxy, n-propoxy, 1-methylethoxy, n-butoxy, 1-methylpropoxy, 2-methylpropoxy, 1,1-dimethylethoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy, preferably $C_1$–$C_4$-alkoxy, in particular $OCH_3$, $OC_2H_5$ or $OCH(CH_3)_2$;

$C_3$–$C_7$-cycloalkyl: cyclopropyl, cyclobutyl, cyclopentyl, cyclohexyl and cycloheptyl;

$C_5$–$C_7$-cycloalkenyl: cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclooct-1-enyl, cyclooct-2-enyl, cyclooct-3-enyl and cyclooct-4-enyl.

3- to 7-membered heterocycle is a saturated, partially or fully unsaturated or aromatic heterocycle having one to three hetero atoms selected from a group consisting of one to three nitrogens, one or two oxygens and one or two sulfur atoms.

With a view to the use of the compounds I as herbicides and/or compounds which have a desiccant/defoliant action, the variables preferably have the following meanings, to be precise in each case alone or in combination:

$X^1$ is hydrogen or halogen, in particular hydrogen or chlorine;
$X^2$ is cyano or halogen, in particular cyano or chlorine;
$x^3$ is hydrogen;
Q is $Q^5$, $Q^7$, $Q^{21}$, $Q^{22}$, $Q^{27}$, $Q^{32}$, $Q^{38}$, $Q^{39}$ or $Q^{40}$;
$A^1$ is oxygen;
$A^3$, $A^4$ are, independently of one another, oxygen;
$A^8$, $A^9$ are, independently of one another, oxygen;
$A^{10}$, $A^{11}$ are, independently of one another, oxygen;
$A^{12}$ is sulfur;
$A^{13}$ is oxygen;
$A^{15}$ is sulfur;
$R^1$ is $C_1-C_4$-alkyl;
$R^2$ is $C_1-C_6$-alkyl, $C_2-C_6$-alkenyl or $C_2-C_6$-alkynyl;
$R^7$ is amino, $C_1-C_6$-alkyl, $C_1-C_6$-haloalkyl, $C_1-C_6$-alkoxy or $C_1-C_6$-haloalkoxy;
$R^8$ is $C_1-C_6$-alkyl, $C_1-C_6$-haloalkyl, $C_3-C_7$-cycloalkyl, $C_2-C_6$-alkenyl or $C_1-C_6$-haloalkoxy;
$R^7$ and $R^8$ may be taken together with the atoms to which they are attached to represent a four to seven membered ring, optionally interrupted by oxygen, sulfur or nitrogen;
$R^9$, $R^{10}$ are, independently of one another, hydrogen, $C_1-C_6$-alkyl, $C_1-C_6$-alkoxy or together with the atoms to which they are attached to represent a 5- or 6-membered ring;
$R^{29}$ is hydrogen, amino or $C_1-C_6$-alkyl;
$R^{30}$ is $C_1-C_6$-haloalkyl, $C_2-C_6$-haloalkoxy or $C_1-C_6$-alkylsulfonyl and
$R^{31}$ is hydrogen, amino, $C_1-C_5$-alkyl, $C_3-C_7$-cycloalkyl or $C_2-C_6$-alkenyl or
$R^{30}$ and $R^{31}$ together with the atoms to which they are attached to represent a 5- or 6-membered ring;
$R^{32}$ is hydrogen, amino, $C_1-C_6$-alkyl, $C_1-C_6$-haloalkyl or $C_2-C_6$-alkenyl;
$R^{33}$ is hydrogen, amino, $C_1-C_6$-alkyl, $C_1-C_6$-haloalkyl or $C_2-C_6$-alkenyl;
$R^{34}$ is hydrogen oder $C_1-C_6$-alkyl;
$R^{35}$ is $C_1-C_6$-haloalkyl, $C_1-C_6$-haloalkoxy or $C_1-C_6$-alkylsulfonyl;
$R^{36}$ is hydrogen, amino, $C_1-C_6$-alkyl, $C_3-C_7$-cycloalkyl or $C_2-C_6$-alkenyl;
$R^{37}$ is hydrogen, cyano, halogen, $C_1-C_6$-alkyl or $C_1-C_6$-alkoxy;
$R^{38}$ is cyano, $C_1-C_6$-alkyl, $C_1-C_6$-haloalkyl, $C_1-C_6$-haloalkoxy or $C_1-C_6$-alkylsulfonyl;
$R^{39}$ is cyano, $C_1-C_6$-alkyl, $C_1-C_6$-haloalkyl, $C_1-C_6$-haloalkoxy or $C_1-C_6$-alkylsulfonyl;
$R^{40}$ is halogen;
$R^{41}$ is hydrogen, amino or $C_1-C_6$-alkyl;
$R^{42}$ is $C_1-C_6$-haloalkyl, $C_1-C_6$-haloalkoxy, $C_1-C_6$-alkylsulfonyl or $C_1-C_6$-alkylsulfonyloxy;
$R^{43}$ is hydrogen, amino or $C_1-C_6$-alkyl;
$R^{44}$ is hydrogen, amino or $C_1-C_6$-alkyl;
$R^{45}$ is hydrogen, amino or $C_1-C_6$-alkyl;
$R^{46}$, $R^{47}$ are, independently of one another, $C_1-C_6$-haloalkyl or together with the nitrogen atoms to which they are attached to represent a 5- or 6-membered ring, optionally interrupted by one oxygen or sulfur ring member.

Very especially preferred are the compounds of the formula Ia (☐ I where $X^1$=fluorine; $X^2$=chlorine; Q=$Q^{21}$; $X^3$=hydrogen; A, $A^8$, $A^9$=oxygen; $R^{29}$=methyl; $R^{30}$=trifluoromethyl; $R^{31}$=hydrogen)

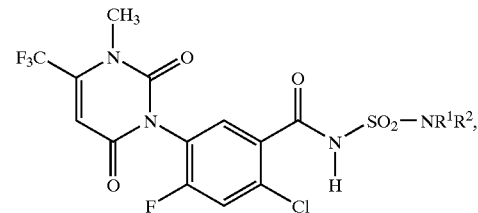

in particular the compounds of Table 1:

TABLE 1

| No. | $R^1$ | $R^2$ |
|---|---|---|
| Ia.1 | H | $CH_3$ |
| Ia.2 | H | $C_2H_5$ |
| Ia.3 | H | $CH_2CH_2$—Cl |
| Ia.4 | H | $CH_2CH_2$—CN |
| Ia.5 | H | $CH_2$—CO—$OCH_3$ |
| Ia.6 | H | $CH_2$—CO—$OC_2H_5$ |
| Ia.7 | H | $CH(CH_3)$—CO—$OCH_3$ |
| Ia.8 | H | $CH_2CH_2$—$OCH_3$ |
| Ia.9 | H | $CH_2$—$C_2H_5$ |
| Ia.10 | H | $CH_2CH_2$—$C_2H_5$ |
| Ia.11 | H | $CH(CH_3)_2$ |
| Ia.12 | H | $CH(CH_3)$—$C_2H_5$ |
| Ia.13 | H | $CH_2$—$CH(CH_3)_2$ |
| Ia.14 | H | $C(CH_3)_3$ |
| Ia.15 | H | $CH(CH_3)$—$CH_2$—$C_2H_5$ |
| Ia.16 | H | $CH_2$—$CH(CH_3)$—$C_2H_5$ |
| Ia.17 | H | $CH_2CH_2$—$CH(CH_3)_2$ |
| Ia.18 | H | $CH_2$—CH=$CH_2$ |
| Ia.19 | H | $CH(CH_3)$=$CH_2$ |
| Ia.20 | H | $CH_2$=CH—$CH_3$ |
| Ia.21 | H | $CH_2$—C≡CH |
| Ia.22 | H | $CH(CH_3)$—C≡CH |
| Ia.23 | H | Cyclopropyl |
| Ia.24 | H | $CH_2$-Cyclopropyl |
| Ia.25 | H | Cyclopentyl |
| Ia.26 | H | $CH_2$-Cyclopentyl |
| Ia.27 | H | $CH_2$-(1,3-Dioxolanyl) |
| Ia.28 | H | $CH_2$-(2-Furyl) |
| Ia.29 | H | $CH_2$-(3-Furyl) |
| Ia.30 | H | $CH_2$-(2-Thienyl) |
| Ia.31 | H | $CH_2$-(3-Thienyl) |
| Ia.32 | H | Phenyl |
| Ia.33 | H | 2-Chlorophenyl |
| Ia.34 | H | 3-Chlorophenyl |
| Ia.35 | H | 4-Chlorophenyl |
| Ia.36 | H | 2-Fluorophenyl |
| Ia.37 | H | 3-Fluorophenyl |
| Ia.38 | H | 4-Fluorophenyl |
| Ia.39 | H | 2-Methylphenyl |
| Ia.40 | H | 3-Methylphenyl |
| Ia.41 | H | 4-Methylphenyl |
| Ia.42 | H | 2-Methoxyphenyl |
| Ia.43 | H | 3-Methoxyphenyl |
| Ia.44 | H | 4-Methoxyphenyl |
| Ia.45 | H | 2-(Methoxycarbonyl)phenyl |
| Ia.46 | H | 3-(Methoxycarbonyl)phenyl |
| Ia.47 | H | 4-(Methoxycarbonyl)phenyl |
| Ia.48 | H | 2-Nitrophenyl |
| Ia.49 | H | 3-Nitrophenyl |
| Ia.50 | H | 4-Nitrophenyl |
| Ia.51 | H | 2-(Dimethylamino)phenyl |
| Ia.52 | H | 3-(Dimethylamino)phenyl |
| Ia.53 | H | 4-(Dimethylamino)phenyl |
| Ia.54 | H | 2-(Trifluoromethyl)phenyl |
| Ia.55 | H | 3-(Trifluoromethyl)phenyl |
| Ia.56 | H | 4-(Trifluoromethyl)phenyl |
| Ia.57 | H | 3-(Phenoxy)phenyl |
| Ia.58 | H | 4-(Phenoxy)phenyl |
| Ia.59 | H | 2,4-Difluorophenyl |
| Ia.60 | H | 2,4-Dichlorophenyl |
| Ia.61 | H | 3,4-Difluorophenyl |

TABLE 1-continued

| No. | R¹ | R² |
|---|---|---|
| Ia.62 | H | 3,4-Dichlorophenyl |
| Ia.63 | H | 3,5-Difluorophenyl |
| Ia.64 | H | 3,5-Dichlorophenyl |
| Ia.65 | H | 2-Pyridyl |
| Ia.66 | H | 3-Pyridyl |
| Ia.67 | H | 4-Pyridyl |
| Ia.68 | H | α-Naphthyl |
| Ia.69 | H | Benzyl |
| Ia.70 | H | 2-Chlorobenzyl |
| Ia.71 | H | 3-Chlorobenzyl |
| Ia.72 | H | 4-Chlorobenzyl |
| Ia.73 | H | 2-Methoxybenzyl |
| Ia.74 | H | 3-Methoxybenzyl |
| Ia.75 | H | 4-Methoxybenzyl |
| Ia.76 | CH₃ | CH₃ |
| Ia.77 | CH₃ | C₂H₅ |
| Ia.78 | CH₃ | CH₂CH₂—Cl |
| Ia.79 | CH₃ | CH₂CH₂—CN |
| Ia.80 | CH₃ | CH₂—CO—OCH₃ |
| Ia.81 | CH₃ | CH₂—CO—OC₂H₅ |
| Ia.82 | CH₃ | CH(CH₃)—CO—OCH₃ |
| Ia.83 | CH₃ | CH₂CH₂—OCH₃ |
| Ia.84 | CH₃ | CH₂—C₂H₅ |
| Ia.85 | CH₃ | CH₂CH₂—C₂H₅ |
| Ia.86 | CH₃ | CH(CH₃)₂ |
| Ia.87 | CH₃ | CH(CH₃)—C₂H₅ |
| Ia.88 | CH₃ | CH₂—CH(CH₃)₂ |
| Ia.89 | CH₃ | C(CH₃)₃ |
| Ia.90 | CH₃ | CH(CH₃)—CH₂—C₂H₅ |
| Ia.91 | CH₃ | CH₂—CH(CH₃)—C₂H₅ |
| Ia.92 | CH₃ | CH₂CH₂—CH(CH₃)₂ |
| Ia.93 | CH₃ | CH₂—CH=CH₂ |
| Ia.94 | CH₃ | CH(CH₃)=CH₂ |
| Ia.95 | CH₃ | CH₂=CH—CH₃ |
| Ia.96 | CH₃ | CH₂—C≡CH |
| Ia.97 | CH₃ | CH(CH₃)—C≡CH |
| Ia.98 | CH₃ | Cyclopropyl |
| Ia.99 | CH₃ | CH₂-Cyclopropyl |
| Ia.100 | CH₃ | Cyclopentyl |
| Ia.101 | CH₃ | CH₂-Cyclopentyl |
| Ia.102 | CH₃ | CH₂-(1,3-Dioxolanyl) |
| Ia.103 | CH₃ | CH₂-(2-Furyl) |
| Ia.104 | CH₃ | CH₂-(3-Furyl) |
| Ia.105 | CH₃ | CH₂-(2-Thienyl) |
| Ia.106 | CH₃ | CH₂-(3-Thienyl) |
| Ia.107 | CH₃ | Phenyl |
| Ia.108 | CH₃ | 2-Chlorophenyl |
| Ia.109 | CH₃ | 3-Chlorophenyl |
| Ia.110 | CH₃ | 4-Chlorophenyl |
| Ia.111 | CH₃ | 2-Fluorophenyl |
| Ia.112 | CH₃ | 3-Fluorophenyl |
| Ia.113 | CH₃ | 4-Fluorophenyl |
| Ia.114 | CH₃ | 2-Methylphenyl |
| Ia.115 | CH₃ | 3-Methylphenyl |
| Ia.116 | CH₃ | 4-Methylphenyl |
| Ia.117 | CH₃ | 2-Methoxyphenyl |
| Ia.118 | CH₃ | 3-Methoxyphenyl |
| Ia.119 | CH₃ | 4-Methoxyphenyl |
| Ia.120 | CH₃ | 2-(Methoxycarbonyl)phenyl |
| Ia.121 | CH₃ | 3-(Methoxycarbonyl)phenyl |
| Ia.122 | CH₃ | 4-(Methoxycarbonyl)phenyl |
| Ia.123 | CH₃ | 2-Nitrophenyl |
| Ia.124 | CH₃ | 3-Nitrophenyl |
| Ia.125 | CH₃ | 4-Nitrophenyl |
| Ia.126 | CH₃ | 2-(Dimethylamino)phenyl |
| Ia.127 | CH₃ | 3-(Dimethylamino)phenyl |
| Ia.128 | CH₃ | 4-(Dimethylamino)phenyl |
| Ia.129 | CH₃ | 2-(Trifluoromethyl)phenyl |
| Ia.130 | CH₃ | 3-(Trifluoromethyl)phenyl |
| Ia.131 | CH₃ | 4-(Trifluoromethyl)phenyl |
| Ia.132 | CH₃ | 3-(Phenoxy)phenyl |
| Ia.133 | CH₃ | 4-(Phenoxy)phenyl |
| Ia.134 | CH₃ | 2,4-Difluorophenyl |
| Ia.135 | CH₃ | 2,4-Dichlorophenyl |
| Ia.136 | CH₃ | 3,4-Difluorophenyl |
| Ia.137 | CH₃ | 3,4-Dichlorophenyl |
| Ia.138 | CH₃ | 3,5-Difluorophenyl |
| Ia.139 | CH₃ | 3,5-Dichlorophenyl |
| Ia.140 | CH₃ | 2-Pyridyl |
| Ia.141 | CH₃ | 3-Pyridyl |
| Ia.142 | CH₃ | 4-Pyridyl |
| Ia.143 | CH₃ | α-Naphthyl |
| Ia.144 | CH₃ | Benzyl |
| Ia.145 | CH₃ | 2-Chlorobenzyl |
| Ia.146 | CH₃ | 3-Chlorobenzyl |
| Ia.147 | CH₃ | 4-Chlorobenzyl |
| Ia.148 | CH₃ | 2-Methoxybenzyl |
| Ia.149 | CH₃ | 3-Methoxybenzyl |
| Ia.150 | CH₃ | 4-Methoxybenzyl |
| Ia.151 | C₂H₅ | C₂H₅ |
| Ia.152 | C₂H₅ | CH₂CH₂—Cl |
| Ia.153 | C₂H₅ | CH₂CH₂—CN |
| Ia.154 | C₂H₅ | CH₂—CO—OCH₃ |
| Ia.155 | C₂H₅ | CH₂—CO—OC₂H₅ |
| Ia.156 | C₂H₅ | CH(CH₃)—CO—OCH₃ |
| Ia.157 | C₂H₅ | CH₂CH₂—OCH₃ |
| Ia.158 | C₂H₅ | CH₂—C₂H₅ |
| Ia.159 | C₂H₅ | CH₂CH₂—C₂H₅ |
| Ia.160 | C₂H₅ | CH(CH₃)₂ |
| Ia.161 | C₂H₅ | CH(CH₃)—C₂H₅ |
| Ia.162 | C₂H₅ | CH₂—CH(CH₃)₂ |
| Ia.163 | C₂H₅ | C(CH₃)₃ |
| Ia.164 | C₂H₅ | CH(CH₃)—CH₂—C₂H₅ |
| Ia.165 | C₂H₅ | CH₂—CH(CH₃)—C₂H₅ |
| Ia.166 | C₂H₅ | CH₂CH₂—CH(CH₃)₂ |
| Ia.167 | C₂H₅ | CH₂—CH=CH₂ |
| Ia.168 | C₂H₅ | CH(CH₃)=CH₂ |
| Ia.169 | C₂H₅ | CH₂=CH—CH₃ |
| Ia.170 | C₂H₅ | CH₂—C≡CH |
| Ia.171 | C₂H₅ | CH(CH₃)—C≡CH |
| Ia.172 | C₂H₅ | Cyclopropyl |
| Ia.173 | C₂H₅ | CH₂-Cyclopropyl |
| Ia.174 | C₂H₅ | Cyclopentyl |
| Ia.175 | C₂H₅ | CH₂-Cyclopentyl |
| Ia.176 | C₂H₅ | CH₂-(1,3-Dioxolanyl) |
| Ia.177 | C₂H₅ | CH₂-(2-Furyl) |
| Ia.178 | C₂H₅ | CH₂-(3-Furyl) |
| Ia.179 | C₂H₅ | CH₂-(2-Thienyl) |
| Ia.180 | C₂H₅ | CH₂-(3-Thienyl) |
| Ia.181 | C₂H₅ | Phenyl |
| Ia.182 | C₂H₅ | 2-Chlorophenyl |
| Ia.183 | C₂H₅ | 3-Chlorophenyl |
| Ia.184 | C₂H₅ | 4-Chlorophenyl |
| Ia.185 | C₂H₅ | 2-Fluorophenyl |
| Ia.186 | C₂H₅ | 3-Fluorophenyl |
| Ia.187 | C₂H₅ | 4-Fluorophenyl |
| Ia.188 | C₂H₅ | 2-Methylphenyl |
| Ia.189 | C₂H₅ | 3-Methylphenyl |
| Ia.190 | C₂H₅ | 4-Methylphenyl |
| Ia.191 | C₂H₅ | 2-Methoxyphenyl |
| Ia.192 | C₂H₅ | 3-Methoxyphenyl |
| Ia.193 | C₂H₅ | 4-Methoxyphenyl |
| Ia.194 | C₂H₅ | 2-(Methoxycarbonyl)phenyl |
| Ia.195 | C₂H₅ | 3-(Methoxycarbonyl)phenyl |
| Ia.196 | C₂H₅ | 4-(Methoxycarbonyl)phenyl |
| Ia.197 | C₂H₅ | 2-Nitrophenyl |
| Ia.198 | C₂H₅ | 3-Nitrophenyl |
| Ia.199 | C₂H₅ | 4-Nitrophenyl |
| Ia.200 | C₂H₅ | 2-(Dimethylamino)phenyl |
| Ia.201 | C₂H₅ | 3-(Dimethylamino)phenyl |
| Ia.202 | C₂H₅ | 4-(Dimethylamino)phenyl |
| Ia.203 | C₂H₅ | 2-(Trifluoromethyl)phenyl |
| Ia.204 | C₂H₅ | 3-(Trifluoromethyl)phenyl |
| Ia.205 | C₂H₅ | 4-(Trifluoromethyl)phenyl |
| Ia.206 | C₂H₅ | 3-(Phenoxy)phenyl |
| Ia.207 | C₂H₅ | 4-(Phenoxy)phenyl |
| Ia.208 | C₂H₅ | 2,4-Difluorophenyl |
| Ia.209 | C₂H₅ | 2,4-Dichlorophenyl |
| Ia.210 | C₂H₅ | 3,4-Difluorophenyl |
| Ia.211 | C₂H₅ | 3,4-Dichlorophenyl |
| Ia.212 | C₂H₅ | 3,5-Difluorophenyl |
| Ia.213 | C₂H₅ | 3,5-Dichlorophenyl |
| Ia.214 | C₂H₅ | 2-Pyridyl |
| Ia.215 | C₂H₅ | 3-Pyridyl |

TABLE 1-continued

| No. | R¹ | R² |
|---|---|---|
| Ia.216 | C₂H₅ | 4-Pyridyl |
| Ia.217 | C₂H₅ | α-Naphthyl |
| Ia.218 | C₂H₅ | Benzyl |
| Ia.219 | C₂H₅ | 2-Chlorobenzyl |
| Ia.220 | C₂H₅ | 3-Chlorobenzyl |
| Ia.221 | C₂H₅ | 4-Chlorobenzyl |
| Ia.222 | C₂H₅ | 2-Methoxybenzyl |
| Ia.223 | C₂H₅ | 3-Methoxybenzyl |
| Ia.224 | C₂H₅ | 4-Methoxybenzyl |
| Ia.225 | CH₂—C₂H₅ | C₂H₅ |
| Ia.226 | CH₂—C₂H₅ | CH₂CH₂—Cl |
| Ia.227 | CH₂—C₂H₅ | CH₂CH₂—CN |
| Ia.228 | CH₂—C₂H₅ | CH₂—CO—OCH₃ |
| Ia.229 | CH₂—C₂H₅ | CH₂—CO—OC₂H₅ |
| Ia.230 | CH₂—C₂H₅ | CH(CH₃)—CO—OCH₃ |
| Ia.231 | CH₂—C₂H₅ | CH₂CH₂—OCH₃ |
| Ia.232 | CH₂—C₂H₅ | CH₂—C₂H₅ |
| Ia.233 | CH₂—C₂H₅ | CH₂CH₂—C₂H₅ |
| Ia.234 | CH₂—C₂H₅ | CH(CH₃)₂ |
| Ia.235 | CH₂—C₂H₅ | CH(CH₃)—C₂H₅ |
| Ia.236 | CH₂—C₂H₅ | CH₂—CH(CH₃)₂ |
| Ia.237 | CH₂—C₂H₅ | C(CH₃)₃ |
| Ia.238 | CH₂—C₂H₅ | CH(CH₃)—CH₂—C₂H₅ |
| Ia.239 | CH₂—C₂H₅ | CH₂—CH(CH₃)—C₂H₅ |
| Ia.240 | CH₂—C₂H₅ | CH₂CH₂—CH(CH₃)₂ |
| Ia.241 | CH₂—C₂H₅ | CH₂—CH=CH₂ |
| Ia.242 | CH₂—C₂H₅ | CH(CH₃)=CH₂ |
| Ia.243 | CH₂—C₂H₅ | CH₂=CH—CH₃ |
| Ia.244 | CH₂—C₂H₅ | CH₂—C≡CH |
| Ia.245 | CH₂—C₂H₅ | CH(CH₃)—C≡CH |
| Ia.246 | CH₂—C₂H₅ | Cyclopropyl |
| Ia.247 | CH₂—C₂H₅ | CH₂-Cyclopropyl |
| Ia.248 | CH₂—C₂H₅ | Cyclopentyl |
| Ia.249 | CH₂—C₂H₅ | CH₂-Cyclopentyl |
| Ia.250 | CH₂—C₂H₅ | CH₂-(1,3-Dioxolanyl) |
| Ia.251 | CH₂—C₂H₅ | CH₂-(2-Furyl) |
| Ia.252 | CH₂—C₂H₅ | CH₂-(3-Furyl) |
| Ia.253 | CH₂—C₂H₅ | CH₂-(2-Thienyl) |
| Ia.254 | CH₂—C₂H₅ | CH₂-(3-Thienyl) |
| Ia.255 | CH₂—C₂H₅ | Phenyl |
| Ia.256 | CH₂—C₂H₅ | 2-Chlorophenyl |
| Ia.257 | CH₂—C₂H₅ | 3-Chlorophenyl |
| Ia.258 | CH₂—C₂H₅ | 4-Chlorophenyl |
| Ia.259 | CH₂—C₂H₅ | 2-Fluorophenyl |
| Ia.260 | CH₂—C₂H₅ | 3-Fluorophenyl |
| Ia.261 | CH₂—C₂H₅ | 4-Fluorophenyl |
| Ia.262 | CH₂—C₂H₅ | 2-Methylphenyl |
| Ia.263 | CH₂—C₂H₅ | 3-Methylphenyl |
| Ia.264 | CH₂—C₂H₅ | 4-Methylphenyl |
| Ia.265 | CH₂—C₂H₅ | 2-Methoxyphenyl |
| Ia.266 | CH₂—C₂H₅ | 3-Methoxyphenyl |
| Ia.267 | CH₂—C₂H₅ | 4-Methoxyphenyl |
| Ia.268 | CH₂—C₂H₅ | 2-(Methoxycarbonyl)phenyl |
| Ia.269 | CH₂—C₂H₅ | 3-(Methoxycarbonyl)phenyl |
| Ia.270 | CH₂—C₂H₅ | 4-(Methoxycarbonyl)phenyl |
| Ia.271 | CH₂—C₂H₅ | 2-Nitrophenyl |
| Ia.272 | CH₂—C₂H₅ | 3-Nitrophenyl |
| Ia.273 | CH₂—C₂H₅ | 4-Nitrophenyl |
| Ia.274 | CH₂—C₂H₅ | 2-(Dimethylamino)phenyl |
| Ia.275 | CH₂—C₂H₅ | 3-(Dimethylamino)phenyl |
| Ia.276 | CH₂—C₂H₅ | 4-(Dimethylamino)phenyl |
| Ia.277 | CH₂—C₂H₅ | 2-(Trifluoromethyl)phenyl |
| Ia.278 | CH₂—C₂H₅ | 3-(Trifluoromethyl)phenyl |
| Ia.279 | CH₂—C₂H₅ | 4-(Trifluoromethyl)phenyl |
| Ia.280 | CH₂—C₂H₅ | 3-(Phenoxy)phenyl |
| Ia.281 | CH₂—C₂H₅ | 4-(Phenoxy)phenyl |
| Ia.282 | CH₂—C₂H₅ | 2,4-Difluorophenyl |
| Ia.283 | CH₂—C₂H₅ | 2,4-Dichlorophenyl |
| Ia.284 | CH₂—C₂H₅ | 3,4-Difluorophenyl |
| Ia.285 | CH₂—C₂H₅ | 3,4-Dichlorophenyl |
| Ia.286 | CH₂—C₂H₅ | 3,5-Difluorophenyl |
| Ia.287 | CH₂—C₂H₅ | 3,5-Dichlorophenyl |
| Ia.288 | CH₂—C₂H₅ | 2-Pyridyl |
| Ia.289 | CH₂—C₂H₅ | 3-Pyridyl |
| Ia.290 | CH₂—C₂H₅ | 4-Pyridyl |
| Ia.291 | CH₂—C₂H₅ | α-Naphthyl |
| Ia.292 | CH₂—C₂H₅ | Benzyl |
| Ia.293 | CH₂—C₂H₅ | 2-Chlorobenzyl |
| Ia.294 | CH₂—C₂H₅ | 3-Chlorobenzyl |
| Ia.295 | CH₂—C₂H₅ | 4-Chlorobenzyl |
| Ia.296 | CH₂—C₂H₅ | 2-Methoxybenzyl |
| Ia.297 | CH₂—C₂H₅ | 3-Methoxybenzyl |
| Ia.298 | CH₂—C₂H₅ | 4-Methoxybenzyl |
| Ia.299 | CH₂—CH₂—C₂H₅ | CH₂CH₂—Cl |
| Ia.300 | CH₂—CH₂—C₂H₅ | CH₂CH₂—CN |
| Ia.301 | CH₂—CH₂—C₂H₅ | CH₂—CO—OCH₃ |
| Ia.302 | CH₂—CH₂—C₂H₅ | CH₂—CO—OC₂H₅ |
| Ia.303 | CH₂—CH₂—C₂H₅ | CH(CH₃)—CO—OCH₃ |
| Ia.304 | CH₂—CH₂—C₂H₅ | CH₂CH₂—OCH₃ |
| Ia.305 | CH₂—CH₂—C₂H₅ | CH₂CH₂—C₂H₅ |
| Ia.306 | CH₂—CH₂—C₂H₅ | CH(CH₃)₂ |
| Ia.307 | CH₂—CH₂—C₂H₅ | CH(CH₃)—C₂H₅ |
| Ia.308 | CH₂—CH₂—C₂H₅ | CH₂—CH(CH₃)₂ |
| Ia.309 | CH₂—CH₂—C₂H₅ | C(CH₃)₃ |
| Ia.310 | CH₂—CH₂—C₂H₅ | CH(CH₃)—CH₂—C₂H₅ |
| Ia.311 | CH₂—CH₂—C₂H₅ | CH₂—CH(CH₃)—C₂H₅ |
| Ia.312 | CH₂—CH₂—C₂H₅ | CH₂CH₂—CH(CH₃)₂ |
| Ia.313 | CH₂—CH₂—C₂H₅ | CH₂—CH=CH₂ |
| Ia.314 | CH₂—CH₂—C₂H₅ | CH(CH₃)=CH₂ |
| Ia.315 | CH₂—CH₂—C₂H₅ | CH₂=CH—CH₃ |
| Ia.316 | CH₂—CH₂—C₂H₅ | CH₂—C≡CH |
| Ia.317 | CH₂—CH₂—C₂H₅ | CH(CH₃)—C≡CH |
| Ia.318 | CH₂—CH₂—C₂H₅ | Cyclopropyl |
| Ia.319 | CH₂—CH₂—C₂H₅ | CH₂-Cyclopropyl |
| Ia.320 | CH₂—CH₂—C₂H₅ | Cyclopentyl |
| Ia.321 | CH₂—CH₂—C₂H₅ | CH₂-Cyclopentyl |
| Ia.322 | CH₂—CH₂—C₂H₅ | CH₂-(1,3-Dioxolanyl) |
| Ia.323 | CH₂—CH₂—C₂H₅ | CH₂-(2-Furyl) |
| Ia.324 | CH₂—CH₂—C₂H₅ | CH₂-(3-Furyl) |
| Ia.325 | CH₂—CH₂—C₂H₅ | CH₂-(2-Thienyl) |
| Ia.326 | CH₂—CH₂—C₂H₅ | CH₂-(3-Thienyl) |
| Ia.327 | CH₂—CH₂—C₂H₅ | Phenyl |
| Ia.328 | CH₂—CH₂—C₂H₅ | 2-Chlorophenyl |
| Ia.329 | CH₂—CH₂—C₂H₅ | 3-Chlorophenyl |
| Ia.330 | CH₂—CH₂—C₂H₅ | 4-Chlorophenyl |
| Ia.331 | CH₂—CH₂—C₂H₅ | 2-Fluorophenyl |
| Ia.332 | CH₂—CH₂—C₂H₅ | 3-Fluorophenyl |
| Ia.333 | CH₂—CH₂—C₂H₅ | 4-Fluorophenyl |
| Ia.334 | CH₂—CH₂—C₂H₅ | 2-Methylphenyl |
| Ia.335 | CH₂—CH₂—C₂H₅ | 3-Methylphenyl |
| Ia.336 | CH₂—CH₂—C₂H₅ | 4-Methylphenyl |
| Ia.337 | CH₂—CH₂—C₂H₅ | 2-Methoxyphenyl |
| Ia.338 | CH₂—CH₂—C₂H₅ | 3-Methoxyphenyl |
| Ia.339 | CH₂—CH₂—C₂H₅ | 4-Methoxyphenyl |
| Ia.340 | CH₂—CH₂—C₂H₅ | 2-(Methoxycarbonyl)phenyl |
| Ia.341 | CH₂—CH₂—C₂H₅ | 3-(Methoxycarbonyl)phenyl |
| Ia.342 | CH₂—CH₂—C₂H₅ | 4-(Methoxycarbonyl)phenyl |
| Ia.343 | CH₂—CH₂—C₂H₅ | 2-Nitrophenyl |
| Ia.344 | CH₂—CH₂—C₂H₅ | 3-Nitrophenyl |
| Ia.345 | CH₂—CH₂—C₂H₅ | 4-Nitrophenyl |
| Ia.346 | CH₂—CH₂—C₂H₅ | 2-(Dimethylamino)phenyl |
| Ia.347 | CH₂—CH₂—C₂H₅ | 3-(Dimethylamino)phenyl |
| Ia.348 | CH₂—CH₂—C₂H₅ | 4-(Dimethylamino)phenyl |
| Ia.349 | CH₂—CH₂—C₂H₅ | 2-(Trifluoromethyl)phenyl |
| Ia.350 | CH₂—CH₂—C₂H₅ | 3-(Trifluoromethyl)phenyl |
| Ia.351 | CH₂—CH₂—C₂H₅ | 4-(Trifluoromethyl)phenyl |
| Ia.352 | CH₂—CH₂—C₂H₅ | 3-(Phenoxy)phenyl |
| Ia.353 | CH₂—CH₂—C₂H₅ | 4-(Phenoxy)phenyl |
| Ia.354 | CH₂—CH₂—C₂H₅ | 2,4-Difluorophenyl |
| Ia.355 | CH₂—CH₂—C₂H₅ | 2,4-Dichlorophenyl |
| Ia.356 | CH₂—CH₂—C₂H₅ | 3,4-Difluorophenyl |
| Ia.357 | CH₂—CH₂—C₂H₅ | 3,4-Dichlorophenyl |
| Ia.358 | CH₂—CH₂—C₂H₅ | 3,5-Difluorophenyl |
| Ia.359 | CH₂—CH₂—C₂H₅ | 3,5-Dichlorophenyl |
| Ia.360 | CH₂—CH₂—C₂H₅ | 2-Pyridyl |
| Ia.361 | CH₂—CH₂—C₂H₅ | 3-Pyridyl |
| Ia.362 | CH₂—CH₂—C₂H₅ | 4-Pyridyl |
| Ia.363 | CH₂—CH₂—C₂H₅ | α-Naphthyl |
| Ia.364 | CH₂—CH₂—C₂H₅ | Benzyl |
| Ia.365 | CH₂—CH₂—C₂H₅ | 2-Chlorobenzyl |
| Ia.366 | CH₂—CH₂—C₂H₅ | 3-Chlorobenzyl |
| Ia.367 | CH₂—CH₂—C₂H₅ | 4-Chlorobenzyl |
| Ia.368 | CH₂—CH₂—C₂H₅ | 2-Methoxybenzyl |
| Ia.369 | CH₂—CH₂—C₂H₅ | 3-Methoxybenzyl |

TABLE 1-continued

| No. | R¹ | R² |
|---|---|---|
| Ia.370 | CH₂—CH₂—C₂H₅ | 4-Methoxybenzyl |
| Ia.371 | CH(CH₃)₂ | CH₂CH₂—Cl |
| Ia.372 | CH(CH₃)₂ | CH₂CH₂—CN |
| Ia.373 | CH(CH₃)₂ | CH₂—CO—OCH₃ |
| Ia.374 | CH(CH₃)₂ | CH₂—CO—OC₂H₅ |
| Ia.375 | CH(CH₃)₂ | CH(CH₃)—CO—OCH₃ |
| Ia.376 | CH(CH₃)₂ | CH₂CH₂—OCH₃ |
| Ia.377 | CH(CH₃)₂ | CH(CH₃)₂ |
| Ia.378 | CH(CH₃)₂ | CH(CH₃)—C₂H₅ |
| Ia.379 | CH(CH₃)₂ | CH₂—CH(CH₃)₂ |
| Ia.380 | CH(CH₃)₂ | C(CH₃)₃ |
| Ia.381 | CH(CH₃)₂ | CH(CH₃)—CH₂—C₂H₅ |
| Ia.382 | CH(CH₃)₂ | CH₂—CH(CH₃)—C₂H₅ |
| Ia.383 | CH(CH₃)₂ | CH₂CH₂—CH(CH₃)₂ |
| Ia.384 | CH(CH₃)₂ | CH₂—CH=CH₂ |
| Ia.385 | CH(CH₃)₂ | CH(CH₃)=CH₂ |
| Ia.386 | CH(CH₃)₂ | CH₂=CH—CH₃ |
| Ia.387 | CH(CH₃)₂ | CH₂—C≡CH |
| Ia.388 | CH(CH₃)₂ | CH(CH₃)—C≡CH |
| Ia.389 | CH(CH₃)₂ | Cyclopropyl |
| Ia.390 | CH(CH₃)₂ | CH₂-Cyclopropyl |
| Ia.391 | CH(CH₃)₂ | Cyclopentyl |
| Ia.392 | CH(CH₃)₂ | CH₂-Cyclopentyl |
| Ia.393 | CH(CH₃)₂ | CH₂-(1,3-Dioxolanyl) |
| Ia.394 | CH(CH₃)₂ | CH₂-(2-Furyl) |
| Ia.395 | CH(CH₃)₂ | CH₂-(3-Furyl) |
| Ia.396 | CH(CH₃)₂ | CH₂-(2-Thienyl) |
| Ia.397 | CH(CH₃)₂ | CH₂-(3-Thienyl) |
| Ia.398 | CH(CH₃)₂ | Phenyl |
| Ia.399 | CH(CH₃)₂ | 2-Chlorophenyl |
| Ia.400 | CH(CH₃)₂ | 3-Chlorophenyl |
| Ia.401 | CH(CH₃)₂ | 4-Chlorophenyl |
| Ia.402 | CH(CH₃)₂ | 2-Fluorophenyl |
| Ia.403 | CH(CH₃)₂ | 3-Fluorophenyl |
| Ia.404 | CH(CH₃)₂ | 4-Fluorophenyl |
| Ia.405 | CH(CH₃)₂ | 2-Methylphenyl |
| Ia.406 | CH(CH₃)₂ | 3-Methylphenyl |
| Ia.407 | CH(CH₃)₂ | 4-Methylphenyl |
| Ia.408 | CH(CH₃)₂ | 2-Methoxyphenyl |
| Ia.409 | CH(CH₃)₂ | 3-Methoxyphenyl |
| Ia.410 | CH(CH₃)₂ | 4-Methoxyphenyl |
| Ia.411 | CH(CH₃)₂ | 2-(Methoxycarbonyl)phenyl |
| Ia.412 | CH(CH₃)₂ | 3-(Methoxycarbonyl)phenyl |
| Ia.413 | CH(CH₃)₂ | 4-(Methoxycarbonyl)phenyl |
| Ia.414 | CH(CH₃)₂ | 2-Nitrophenyl |
| Ia.415 | CH(CH₃)₂ | 3-Nitrophenyl |
| Ia.416 | CH(CH₃)₂ | 4-Nitrophenyl |
| Ia.417 | CH(CH₃)₂ | 2-(Dimethylamino)phenyl |
| Ia.418 | CH(CH₃)₂ | 3-(Dimethylamino)phenyl |
| Ia.419 | CH(CH₃)₂ | 4-(Dimethylamino)phenyl |
| Ia.420 | CH(CH₃)₂ | 2-(Trifluoromethyl)phenyl |
| Ia.421 | CH(CH₃)₂ | 3-(Trifluoromethyl)phenyl |
| Ia.422 | CH(CH₃)₂ | 4-(Trifluoromethyl)phenyl |
| Ia.423 | CH(CH₃)₂ | 3-(Phenoxy)phenyl |
| Ia.424 | CH(CH₃)₂ | 4-(Phenoxy)phenyl |
| Ia.425 | CH(CH₃)₂ | 2,4-Difluorophenyl |
| Ia.426 | CH(CH₃)₂ | 2,4-Dichlorophenyl |
| Ia.427 | CH(CH₃)₂ | 3,4-Difluorophenyl |
| Ia.428 | CH(CH₃)₂ | 3,4-Dichlorophenyl |
| Ia.429 | CH(CH₃)₂ | 3,5-Difluorophenyl |
| Ia.430 | CH(CH₃)₂ | 3,5-Dichlorophenyl |
| Ia.431 | CH(CH₃)₂ | 2-Pyridyl |
| Ia.432 | CH(CH₃)₂ | 3-Pyridyl |
| Ia.433 | CH(CH₃)₂ | 4-Pyridyl |
| Ia.434 | CH(CH₃)₂ | α-Naphthyl |
| Ia.435 | CH(CH₃)₂ | Benzyl |
| Ia.436 | CH(CH₃)₂ | 2-Chlorobenzyl |
| Ia.437 | CH(CH₃)₂ | 3-Chlorobenzyl |
| Ia.438 | CH(CH₃)₂ | 4-Chlorobenzyl |
| Ia.439 | CH(CH₃)₂ | 2-Methoxybenzyl |
| Ia.440 | CH(CH₃)₂ | 3-Methoxybenzyl |
| Ia.441 | CH(CH₃)₂ | 4-Methoxybenzyl |
| Ia.442 | —(CH₂)₄— | |
| Ia.443 | —CH₂—CH=CH—CH₂— | |

Other very especially preferred compounds I are those of the formulae Ib to Iz, Iφ, Iλ, Iπ, Iψ and Iζ, in particular the compounds Ib.1 to Ib.443, which differ from the corresponding compounds Ia.1 to Ia.443 only in that $R^{29}$ is amino:

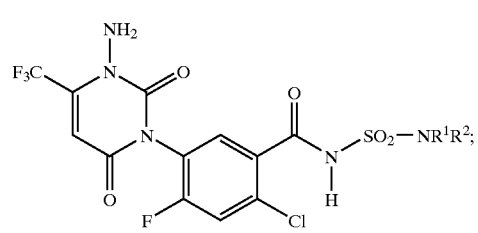

Ib the compounds Ic.1 to Ic.443, which differ from the corresponding compounds Ia.1 to Ia.443 only in that $X^1$ is hydrogen:

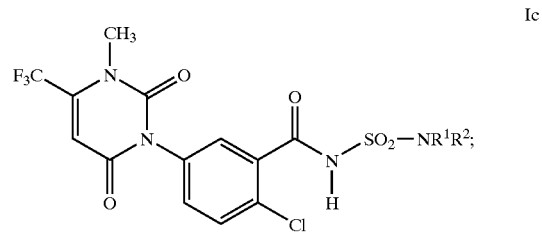

Ic the compounds Id.1 to Id.443, which differ from the corresponding compounds Ia.1 to Ia.443 only in that $X^1$ is hydrogen and $R^{29}$=amino:

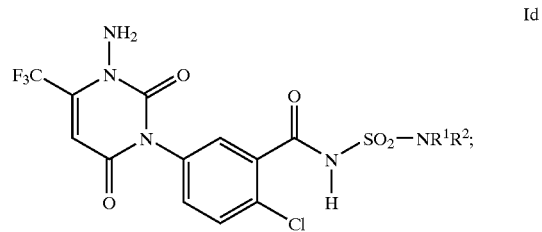

Id the compounds Ie.1 to Ie.443, which differ from the corresponding compounds Ia.1 to Ia.443 in that Q is $Q^5$, $A^1$ is oxygen, $R^7$ is difluoromethyl and $R^8$ is methyl:

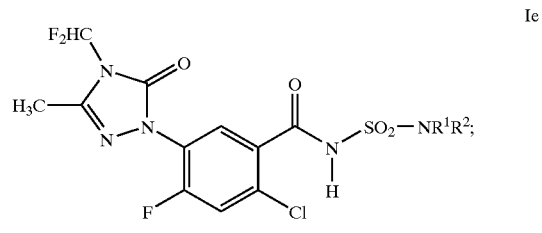

Ie the compounds If.1 to If.443, which differ from the corresponding compounds Ia.1 to Ia.443 in that $X^1$ is chlorine, Q is $Q^5$, $A^1$ is oxygen, $R^7$ is difluoromethyl and $R^8$ is methyl:

If

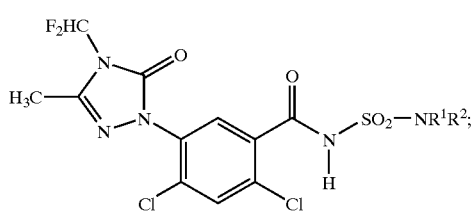

the compounds Ig.1 to Ig.443, which differ from the corresponding compounds Ia.1 to Ia.443 in that Q is $Q^5$, $A^1$ is oxygen and $R^7+R^8$ is tetramethylene;

Ig

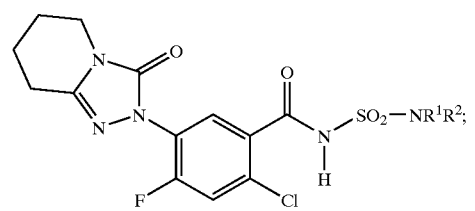

the compounds Ih.1 to Ih.443, which differ from the corresponding compounds Ia.1 to Ia.443 in that $X^1$ is chlorine, Q is $Q^5$, $A^1$ is oxygen and $R^7+R^8$ is tetramethylene:

Ih

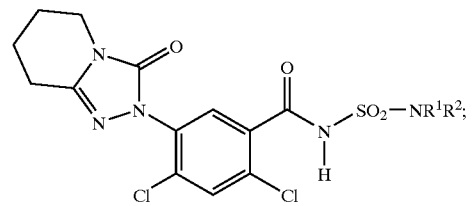

the compounds Ij.1 to Ij.443, which differ from the corresponding compounds Ia.1 to Ia.443 in that Q is $Q^{22}$, $A^{10}$ and $A^{11}$ are oxygen, $A^{12}$ is sulfur and $R^{32}$, $R^{33}$ are methyl:

Ij

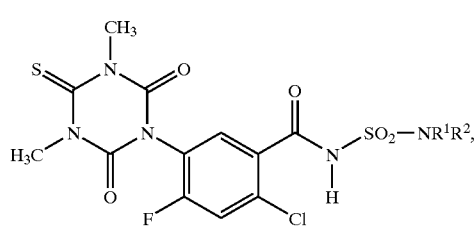

the compounds Ik.1 to Ik.443, which differ from the corresponding compounds Ia.1 to Ia.443 in that Q is $Q^{22}$, $A^{10}$, $A^{11}$ & $A^{12}$ are oxygen and $R^{32}$ & $R^{33}$ are methyl:

Ik

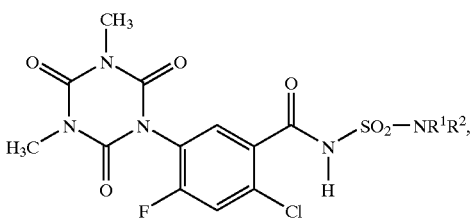

the compounds Im.1 to Im.443, which differ from the corresponding compounds Ia.1 to Ia.443 in that Q is $Q^{27}$, $A^{13}$ is oxygen, $R^{34}$ & $R^{36}$ are hydrogen and $R^{35}$ is trifluoromethyl:

Im

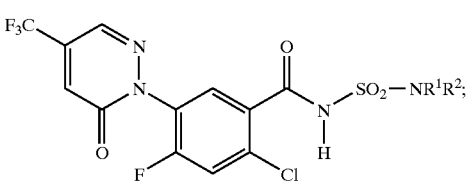

the compounds In.1 to In.443, which differ from the corresponding compounds Ia.1 to Ia.443 in that Q is $Q^{27}$, $A^{13}$ is oxygen, $R^{34}$ is hydrogen, $R^{35}$ is trifluoromethyl and $R^{36}$ is methyl:

In

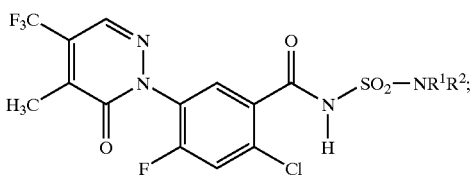

the compounds Io.1 to Io.443, which differ from the corresponding compounds Ia.1 to Ia.443 in that Q is $Q^{27}$, $A^{13}$ is oxygen, $R^{34}$ is hydrogen, $R^{35}$ is $SO_2$—$CH_3$ and $R^{36}$ is amino:

Io

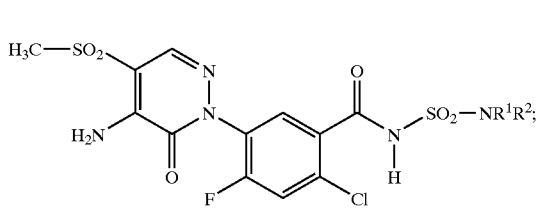

the compounds Ip.1 to Ip.443, which differ from the corresponding compounds Ia.1 to Ia.443 in that Q is $Q^{32}$, $R^{37}$ is chlorine, $R^{38}$ is difluoromethoxy and $R^{39}$ is methyl:

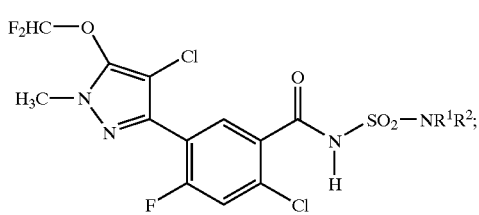

Ip the compounds Iq.1 to Iq.443, which differ from the corresponding compounds Ia.1 to Ia.443 in that Q is $Q^{32}$, $R^{37}$ is bromine, $R^{38}$ is difluoromethoxy and $R^{39}$ is methyl:

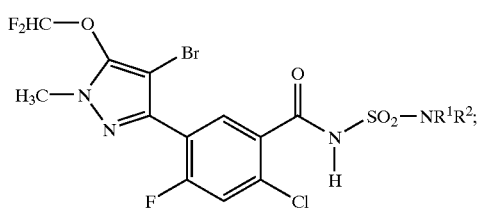

Iq the compounds Ir.1 to Ir.443, which differ from the corresponding compounds Ia.1 to Ia.443 in that $X^1$ is chlorine, Q is $Q^{32}$, $R^{37}$ is bromine, $R^{38}$ is difluoromethoxy and $R^{39}$ is methyl:

Ir the compounds Is.1 to Is.443, which differ from the corresponding compounds Ia.1 to Ia.443 in that Q is $Q^{32}$, $R^{37}$ is chlorine, $R^{38}$ is trifluoromethyl and $R^{39}$ is methyl:

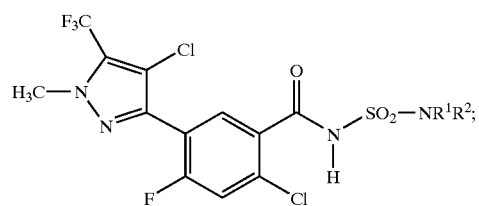

Is the compounds It.1 to It.443, which differ from the corresponding compounds Ia.1 to Ia.443 in that Q is $Q^{32}$, $R^{37}$ is bromine, $R^{38}$ is trifluoromethyl and $R^{39}$ is methyl:

It the compounds Iu.1 to Iu.443, which differ from the corresponding compounds Ia.1 to Ia.443 in that $X^1$ is chlorine, Q is $Q^{32}$, $R^{37}$ is bromine, $R^{38}$ is trifluoromethyl and $R^{39}$ is methyl:

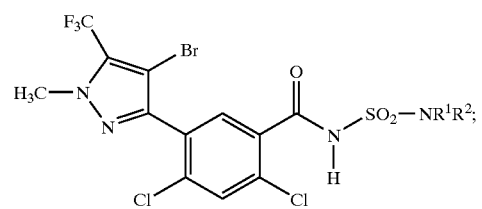

Iu the compounds Iv.1 to Iv.443, which differ from the corresponding compounds Ia.1 to Ia.443 in that Q is $Q^{32}$, $R^{37}$ is chlorine, $R^{38}$ is $SO_2$—$CH_3$ and $R^{39}$ is methyl:

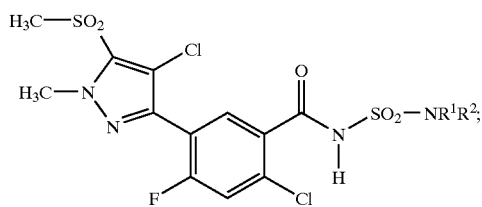

Iv the compounds Iw.1 to Iw.443, which differ from the corresponding compounds Ia.1 to Ia.443 in that Q is $Q^{32}$, $R^{37}$ is bromine, $R^{38}$ is $SO_2$—$CH_3$ and $R^{39}$ is methyl:

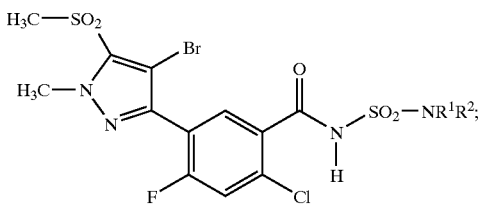

Iw the compounds Ix.1 to Ix.443, which differ from the corresponding compounds Ia.1 to Ia.443 in that $X^1$ is chlorine, Q is $Q^{32}$, $R^{37}$ is bromine, $R^{38}$ is $SO_2$—$CH_3$ and $R^{39}$ is methyl:

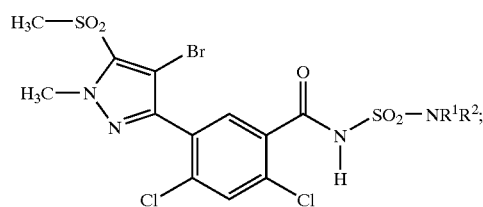

Ix the compounds Iy.1 to Iy.443, which differ from the corresponding compounds Ia.1 to Ia.443 in that Q is $Q^{38}$, $R^{40}$ is chlorine, $R^{41}$, $R^{43}$ are hydrogen and $R^{42}$ is trifluoromethyl:

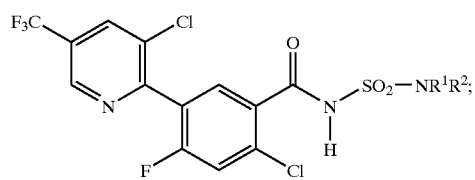

Iy the compounds Iz.1 to Iz.443, which differ from the corresponding compounds Ia.1 to Ia.443 in that Q is $Q^{39}$, $A^1$ is oxygen, $A^{15}$ is sulfur, $R^{44}$ and $R^{45}$ are methyl:

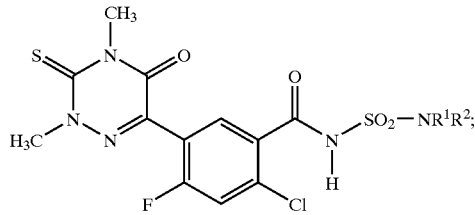

Iz the compounds Iφ.1 to Iφ.430 which differ from the corresponding compounds Ia.1 to Ia.443 in that Q is $Q^{40}$, $A^{16}$ & $A^{17}$ are oxygen and $R^{46}+R^{47}$ form a chain —CH$_2$CH$_2$—O—CH$_2$—:

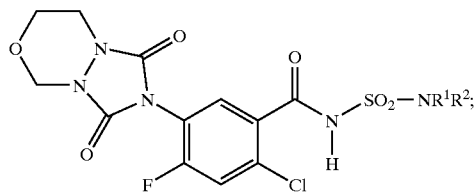

Iφ the compounds Iλ.1 to Iλ.443, which differ from the corresponding compounds Ia.1 to Ia.443 in that Q is $Q^{40}$, $A^{16}$ is sulfur, $A^{17}$ is oxygen and $R^{46}+R^{47}$ form a chain —CH$_2$CH$_2$—O—CH$_2$—:

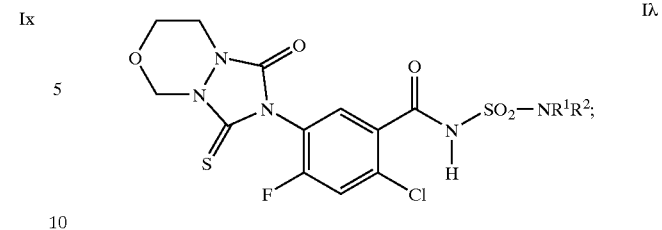

Iλ the compounds Iπ.1 to Iπ.443, which differ from the corresponding compounds Ia.1 to Ia.443 in that Q is $Q^{40}$, $A^{16}$ & $A^{17}$ are sulfur and $R^{46}+R^{47}$ form a chain —CH$_2$CH$_2$—O—CH$_2$—:

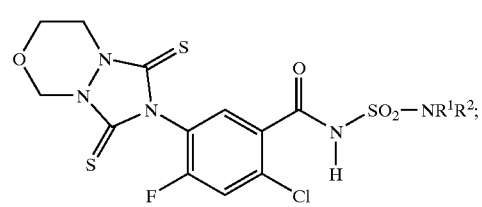

Iπ the compounds Iψ.1 to Iψ.443, which differ from the corresponding compounds Ia.1 to Ia.443 in that Q is $Q^{40}$, $A^{16}$ is oxygen, $A^{17}$ is sulfur and $R^{46}+R^{47}$ form a chain —CH$_2$CH$_2$—O—CH$_2$—:

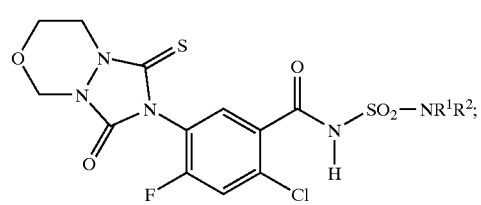

Iψ the compounds Iζ.1 to Iζ.443, which differ from the corresponding compounds Ia.1 to Ia.443 in that Q is $Q^7$, $A^3$ & $A^4$ are oxygen and $R^9+R^{10}$ form a tetramethylene chain:

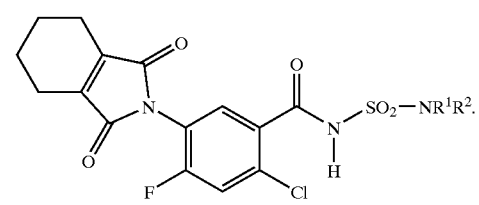

Iξ

The uracil substituted phenyl sulfamoyl carboxamides I according to the invention are obtainable by various routes available and known to those skilled to the art, preferably by one of the processes described hereinbelow.)

A) Reaction of a benzoic acid derivative II with a sulfamide III, optionally in the presence of a coupling agent such as N,N-carbonyldiimidazole (CDI) or after converting II into the corresponding acid chloride:

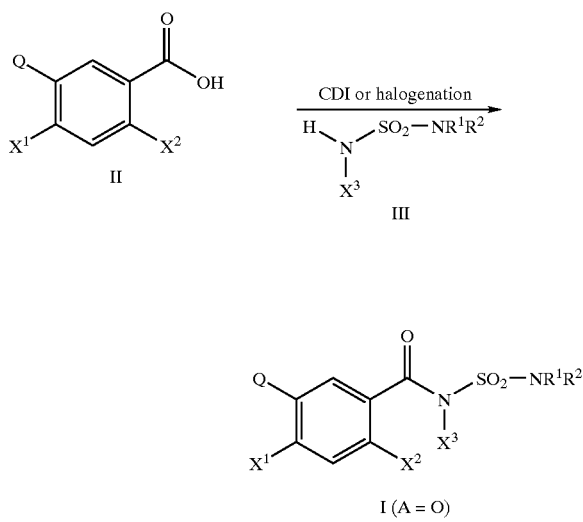

N,N'-carbonyldiimidazole (CDI) is added to a solution of the carboxylic acid derivative of formula II in an inert solvent such as tetrahydrofuran. The resulting mixture is stirred under reflux for a sufficient period of time to allow the reaction to come to completion, and is then cooled to room temperature. An optionally substituted sulfamide III is added followed by diazabicycloundecane (DBU) and the mixture is stirred until the reaction is complete. Standard workup and isolation methods give the product in purified form.

The benzoic acid derivatives II—and the corresponding carboxylates, which can be saponified in a simply manner to give the free acids II—are known from the literature or can be prepared analogously to methods known from the literature.

The methods for saponifying the esters to the benzoic acid derivatives II are sufficiently well known to the skilled artisan; consequently, details are not necessary. By way of example, reference is made to Kocienski, "Protecting Groups", Thieme Verlag 1994, and Greene, Wuts, Protecting groups in organic synthesis, Wiley 1999, and Houben-Weyl, Methoden der organischen Chemie, Vol. E5, Part I (1985), pp. 223 et seq.

In addition to activation to the imidazolones other methods are also suitable.

Various methods are suitable for activating the acids. They can, for example, be converted to the acid chloride by treating them with $SOCl_2$, $POCl_3$, $PCl_5$, $COCl_2$ or $(COCl)_2$. Alternatively, the imidazolide can be prepared by reaction with N,N-carbonyldiimidazole. The methods used are sufficiently well known to the skilled artisan, e.g., from Houben Weyl, Methoden der organischen Chemie, Vol. E5 (1985), Part 1, pp. 587 et seq. and Vol. E5 (1985), Part II, pp. 934 et seq.

Methods of preparing benzoic acid derivatives II where Q is other than $Q^{21}$ include those methods described in U.S. Pat. No. 5,872,253, U.S. Pat. No. 5,484,763 and in co-pending patent application Ser. No. 09/368,340 filed Aug. 4, 1999 and incorporated herein by reference thereto.

The precursors required for the synthesis of compounds I in which $Q=Q^{21}$, such as 2-chloro-5[3,6-dihydro-3-methyl-2,6-dioxo-4-(trifluoromethyl)-1(2H)-pyrimidinyl]-4-fluorobenzoic acid (CAS No. 120890-57-5), are described for example in EP-A 195 346, WO 89/02891, WO 98/08151 and the literature cited therein, or may be produced in the manner disclosed therein.

With regard to the esters of II where $Q=Q^5$, $A^1$=oxygen, $R^7$=difluoromethyl, $R^8$=methyl, $X^1$=fluorine or chlorine and $X^2$=chlorine, reference is made to U.S. Pat. No. 5,035,740 and GB-A 22 53 625; with regard to II where $Q=Q^5$ and where $R^7$ and $R^8$ together with the atoms to which they are attached form a 6-membered ring, such as 2-chloro-4-fluoro-5-(5,6,7,8-tetrahydro-3-oxo-1,2,4-triazolo[4,3-a]pyridin-2(3H)-yl)benzoic acid methyl ester (CAS No. 104799-37-3), reference is made to JP-A 61/069,776. Such compounds are also mentioned in WO 94/22860.

Benzoic acid derivatives II where Q is $Q^{22}$, $A^{10}$ & $A^{11}$=oxygen, $A^{12}$=oxygen or sulfur, $R^{32}$ & $R^{33}$=amino or alkyl, $X^1$=fluorine and $X^2$=chlorine are known from EP-A 584,655 and WO 00/50409, e.g. 2-chloro-5-(3,5-dimethyl-2,6-dioxo-4-thioxo-1,3,5-triazinan-1-yl)-4-fluorobenzoic acid (CAS No. 289882-59-3) and 2-chloro-5-(3,5-dimethyl-2,4,6-trioxo-1,3,5-triazinan-1-yl)-4-fluorobenzoic acid methyl ester (CAS No. 154883-47-3).

Benzoic acid derivatives II and their esters where Q is $Q^{27}$ are known from WO 97/07104, WO 96/39392, WO 99/14201 and WO 99/52870, e.g. 2-chloro-4-fluoro-5-(5-trifluormethyl-3-pyridazinon-2-yl) benzoic acid ($R^{34}$=hydrogen, $R^{35}$=trifluoromethyl, $R^{36}$=hydrogen, $X^1$=fluorine and $X^2$=chlorine) and 2-chloro-4-fluoro-5-(4-trifluoromethyl-5-trifluoromethyl-3-pyridazinon-2-yl) benzoic acid (CAS No. 259141-58-7; $R^{34}$=hydrogen, $R^{35}$=trifluoromethyl, $R^{36}$=methyl, $X^1$=fluorine, $X^2$=chlorine).

Benzoic acid derivatives II where Q is $Q^{32}$ are known from EP-A 361,114, WO 92/06962, WO 96/02515, U.S. Pat. No. 6,096,689 and WO 98/38169, e.g. 4-Chloro-3-[4-chloro-2-fluoro-5-carboxy-phenyl]-5-difluorormethoxy-1-methyl-1H-pyrazole (CAS No. 129631-53-4; $Q=Q^{32}$; $R^{37}$=chlorine, $R^{38}$=difluoromethoxy, $R^{39}$=methyl, $X^1$=fluorine, $X^2$=chlorine), 4-Chloro-3-[4-chloro-2-fluoro-5-carboxyphenyl]-5-trifluoromethyl-1-methyl-1H-pyrazole (CAS-No. 142622-56-8; $Q=Q^{32}$, $R^{37}$=chlorine, $R^{38}$=difluoromethoxy, $R^{39}$=methyl, $X^1$=fluorine, $X^2$=chlorine), or can be prepared in a manner similar to that described there.

Benzoic acid derivatives II where Q is $Q^{38}$ are known from WO 95/02580, U.S. Pat. No. 5,783,522 and WO 98/07700, e.g. 2-chloro-5-[3-chloro-5-(trifluoromethyl)-2-pyridinyl]-4-fluorobenzoic acid (CAS No. 188782-31-2), or can be prepared in a manner similar to that described there.

Benzoic acid derivatives II where Q is $Q^{39}$ are known from WO 99/59983 and DE-A 19 835 943, or can be prepared in a manner similar to that described there.

Benzoic acid derivatives II where Q is $Q^{40}$ are known from WO 94/10173 and WO 00/01700, or can be prepared in a manner similar to that described there.

Benzoic acid derivatives II where Q is $Q^5$ can be prepared according to U.S. Pat. No. 5,035,740 as follows:

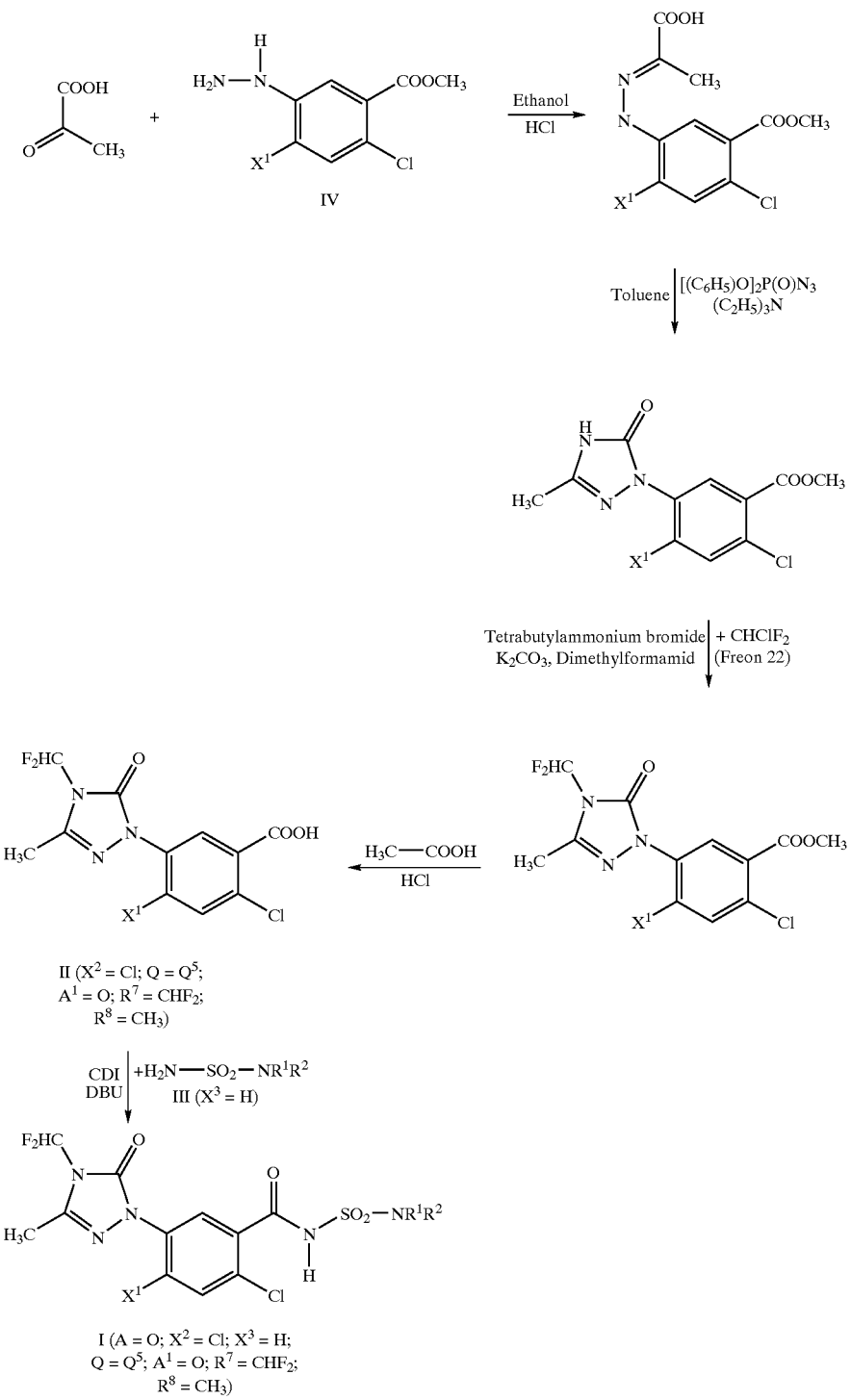

The hydrazines IV are known, e.g, from WO 97/07104 ($X^1$=fluorine), or may be prepared in known manner.

The sulfamides of the formula III are obtainable according to methods known per se, for example analogously to the method described in Hamprecht et al., Angew. Chemie 21, 151 (1981) and Houben-Weyl, Methoden der Organischen Chemie, Vol. E11 (1985), pp. 1019 et seq.

As an example, formula III sulfamides where $X^3$ is hydrogen may be prepared by reaction of S-chlorosulfonamide with an amine $HNR^1R^2$:

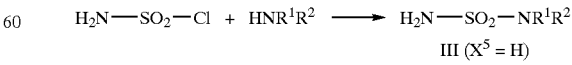

Formula III sulfamides where $X^3$ is not hydrogen may be prepared by reaction of sulfuryl chloride with an amine $HNR^1R^2$ to give the sulfamoyl chloride compound $Cl-SO_2-NR^1R^2$, and reacting said sulfamoyl chloride compound with an amine $X^3-NH_2$:

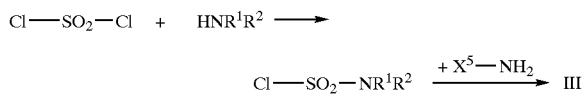

B) Displacement of a halide by Q:

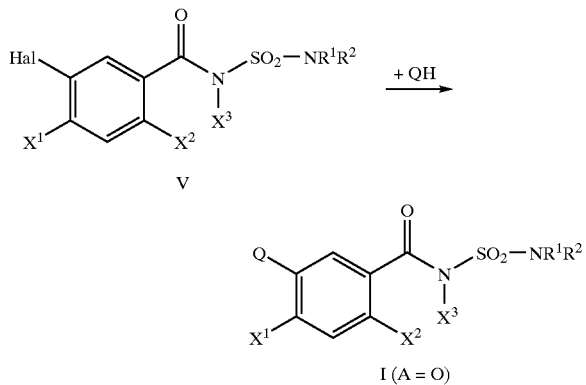

Hal=halogen, preferably fluorine, chlorine or bromine.

By this route, an aniline of formula IV is converted to a diazonium salt, then treated with iodine and potassium iodide to give the iodo compound of the formula V. Reaction of formula V compounds with an unsubstituted QH moiety, for example, a uracil of formula $Q^{21}H$ in the presence of a copper(I) catalyst gives a final product of formula Ia. In this way, compounds I according to the invention where $Q=Q^{21}$ can be obtained, by analogy to the method disclosed by T. Maruyama, K. Fujiwara and M. Fukuhara in J. Chem. Soc., Perkin Trans. 1995 (7), pp. 733–734, where Hal=iodine, and the reaction is carried out with the addition of a Cu(I) source.

However, transition-metal-free methods are also suitable if the substituents Hal, $X^1$ and $X^2$ are properly selected. In this respect, reference is made by way of example to WO 96/39392, which describes methods which are suitable for the manufacture of compounds I where $Q=Q^{27}$.

The haloaryl precursors V can be obtained by a Sandmeyer reaction from the corresponding anilines (see also formula scheme V). These methods are sufficiently well known to the skilled artisan, so reference is only made here to Houben-Weyl, Methoden der Org. Chemie, Vol. 5/4, 4th edition 1960, pp. 438 et seq.

C) Reaction of an aniline intermediate VI with an oxazinone compound of the formula VII to give a compound I where A is oxygen, $X^3$ is hydrogen, Q is $Q^{21}$, $A^8$ & $A^9$ are oxygen and $R^{29}$ is hydrogen, optionally followed by alkylation and hydrolysis:

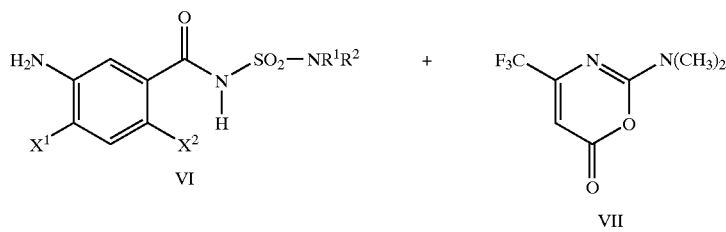

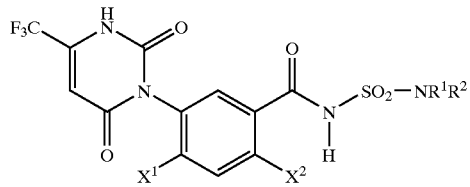

I
(A = O; $X^3$ = H; Q = $Q^{21}$; $A^8$, $A^9$ = O; $R^{29}$ = H)

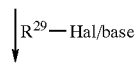

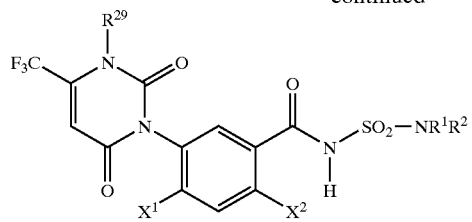

I (A = O; $X^3$ = H; Q = $Q^{21}$; $A^8$, $A^9$ = O; $R^{29}$ ☐ H; $R^{30}$ = $CF_3$; $R^{31}$ = H)

$R^{29}$—Hal represents a $C_1$-$C_6$-alkyl, $C_1$-$C_6$-haloalkyl, $C_3$-$C_7$-cycloalkyl, $C_2$-$C_6$-alkenyl, $C_2$-$C_6$-haloalkenyl or $C_3$-$C_6$-alkynyl halide.

Among the methods known for the preparation of oxazinone compounds VII are those described in WO 99/14216.

Formula VI aniline derivatives may be prepared by conventional procedures such as the conversion of the appropriately substituted benzoic acid IX to the corresponding sulfamoyl carboxamide X (see method A) above), which in turn is then nitrated and reduced:

The nitrated compounds XI can then be reduced to the aniline derivatives VI.

The reduction is generally carried out by reaction of the nitro compound with a transition metal such as iron, zinc or tin under acidic conditions or with a complex hydride such as lithium aluminium hydride and sodium borohydride, the reduction being carried out in bulk or in a solvent or diluent.

Examples of suitable solvents are—depending on the reducing agent selected—water, alcohols such as methanol, ethanol and isopropanol, or ethers such as diethyl ether,

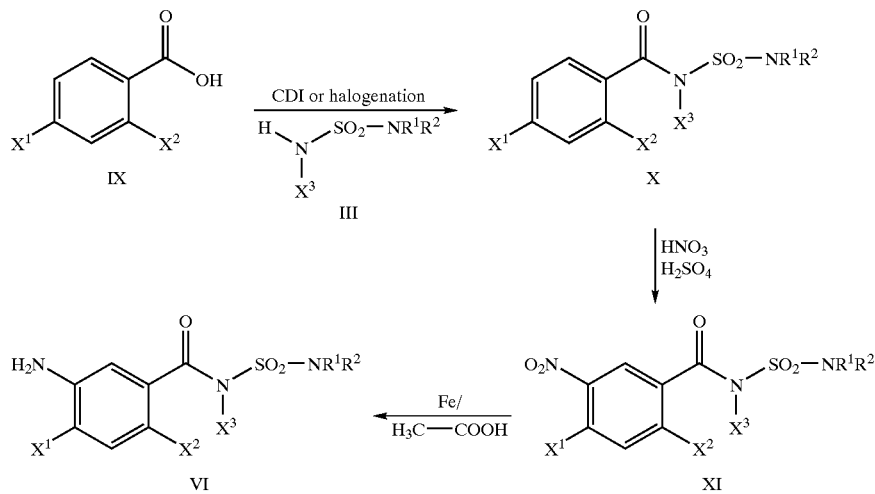

Suitable nitration reagents are for example nitric acid in various concentrations, including concentrated and fuming nitric acid, mixtures of sulfuric and nitric acid, and acetyl nitrates and alkyl nitrates.

The reaction can be carried out either without a solvent in an excess of the nitration reagent or in an inert solvent or diluent, suitable agents being, for example, water, mineral acids, organic acids, halohydrocarbons such as methylene chloride, anhydrides such as acetic anhydride, and mixtures thereof.

The sulfamoyl carboxamide X and the nitration reagent are expediently employed in approximately equimolar amounts; with regard to the yield of X, it may be advantageous to use the nitration reagent in an excess of up to about 10 times the molar amount, based on the amount of X. When the reaction is carried out without a solvent in the nitration reagent, the latter is present in an even greater excess.

The reaction temperature is generally from (−100)° C. to 200° C., preferably from (−30) to 50° C.

methyl tert-butyl ether, dioxane, tetrahydrofuran and ethylene glycol dimethyl ether.

If a metal is used for reduction purposes, it is preferable to work without a solvent in an inorganic acid, especially in concentrated or dilute hydrochloric acid, or in a liquid organic acid such as acetic acid and propionic acid. However, the acid can also be diluted with an inert solvent, e.g., one of those mentioned above. The reduction with complex hydrides is carried out preferably in a solvent, for example an ether or an alcohol.

The nitrated compound XI and the reducing agent are frequently used in approximately equimolar amounts; to optimize the reaction it may however be advantageous to use either component in an excess of up to about the 10-fold molar amount.

The amount of acid is not critical. So as to reduce the starting compound as completely as possible, it is expedient to use at least an equivalent amount of acid. Frequently, the acid is used in excess, based on the nitrated compound XI.

The reaction temperature is generally from (−30) to 200° C., preferably from 0 to 80° C.

For working up, the reaction mixture is as a rule diluted with water and the product is isolated by filtration, crystallization or extraction with a solvent which is substantially immiscible with water, e.g., ethyl acetate, diethyl ether or methylene chloride. If desired, the product VI can then be purified in conventional manner.

The nitro group of compounds XI can also be hydrogenated catalytically with hydrogen. Examples of suitable catalysts to this end are Raney nickel, palladium on charcoal, palladium oxide, platinum and platinum oxide. An amount of from 0.05 to 50 mol %, based on the compound XI to be reduced, is generally sufficient.

It is possible to dispense with a solvent, or to use an inert solvent or diluent, e.g., acetic acid, a mixture of acetic acid and water, ethyl acetate, ethanol or toluene. When the catalyst has been separated off, the reaction solution can be worked up as usual to give the product VI. Hydrogenation can be effected at atmospheric or superatmospheric hydrogen pressure.

Further methods and reaction conditions are given in the literature (see, for example, Houben-Weyl, Methoden der Organischen Chemie, nitrogen compounds I, Part 1 (1971), Vol. X/1, pp. 463 et seq.).

Not only the compounds I according to the invention where $Q=Q^{21}$, but also compounds I where $Q=Q^7$, $Q^{22}$ or $Q^{40}$ can be produced from the aniline derivatives VI. To prepare compounds I where $Q=Q^{22}$, reference is made to the methods described in WO 00/50409 and EP-A 584 655, and to prepare compounds I where $Q=Q^{40}$, reference is made to the methods taught in WO 94/10173 and WO 00/01700.

The aniline derivatives VI can, however, also be converted in conventional manner (see, for example, WO 97/07104 and Houben-Weyl, Methoden der Organischen Chemie, Vol. E1, nitrogen compounds) to the corresponding hydrazines, from which compounds I where $Q=Q^5$ oder $Q^{27}$ can be prepared.

Further methods for preparing compounds I according to the invention are given in Böger, Wakabayashi Peroxidizing herbicides, Springer Verlag 1999.

D) Reacting a benzoic acid derivative VIII with an electrophilic amination reagent in the presence of a base to give the corresponding N-amino uracil benzoic ester, hydrolyzing said ester to give the benzoic acid II (with $Q=Q^{21}$; $A^8$ & $A^9$=O; $R^{29}$=NH$_2$) and converting the latter to the compounds I (A=O; $Q=Q^{21}$; $A^8$ & $A^9$=O; $R^{29}$=NH$_2$) by the route described above:

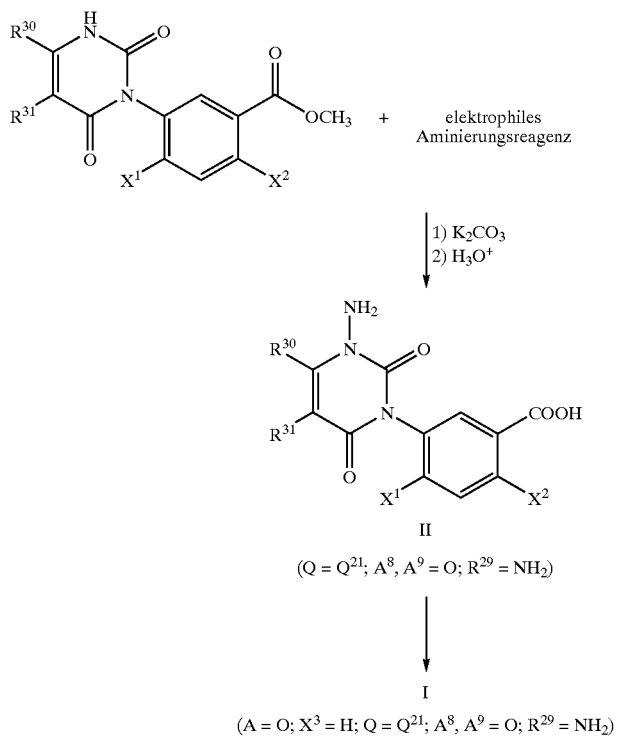

Examples of electrophilic amination reagents are in particular 2,4-dinitrophenylhydroxylamine and O-mesitylenesulfonyl hydroxylamine.

Examples of suitable reaction conditions are given in DE-A 19 652 431.

All the processes described above are expediently carried out under atmospheric pressure or under the inherent pressure of the reaction mixture in question.

As a rule, the reaction mixtures are worked up by methods known per se, for example by removing the solvent, partitioning the residue between a mixture of water and a suitable organic solvent and working up the organic phase to obtain the product.

The uracil substituted phenyl sulfamoyl carboxamides I according to the invention can be obtained from the preparation as isomer mixtures which, if desired, can be separated into the pure isomers by the methods conventionally used for this purpose, eg. by means of crystallization or chromatography on an optically active adsorbate. Pure optically active isomers can, for example, also be prepared from suitable optically active starting materials.

Compounds I with C—H acidic substituents can be converted into their alkali metal salts in a manner known per se by reaction with a base of the corresponding cation.

Salts of I whose metal ion is not an alkali metal ion can normally be prepared by double decomposition of the corresponding alkali metal salt in aqueous solution.

Other metal salts, such as manganese, copper, zinc, iron, calcium, magnesium and barium salts, can be prepared from the sodium salts in the customary manner, and also ammonium and phosphonium salts by means of ammonia, phosphonium, sulfonium or sulfoxonium hydroxides.

The compounds I and their agriculturally useful salts are suitable as herbicides, both in the form of isomer mixtures and in the form of the pure isomers. The herbicidal compositions comprising I effect very good control of vegetation on non-crop areas, especially at high rates of application. In crops such as wheat, rice, maize, soybeans and cotton they act against broad-leaved weeds and grass weeds without damaging the crop plants substantially. This effect is observed especially at low rates of application.

Depending on the application method in question, the compounds I, or compositions comprising them, can additionally be employed in a further number of crop plants for eliminating undesirable plants. Examples of suitable crops are the following: *Allium cepa, Ananas comosus, Arachis hypogaea, Asparagus officinalis, Beta vulgaris* spec. *altissima, Beta vulgaris* spec. *rapa, Brassica napus* var. *napes, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N.rustica*), *Olea europaea, Oryza sativa, Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays.*

Moreover, the compounds I may also be used in crops which have been made fully or partially tolerant to the action of herbicides due to breeding including genetic engineering methods.

Furthermore, the substituted hydroximic acid derivatives I are also suitable for the desiccation and/or defoliation of plants.

As desiccants, they are especially suitable for desiccating the aerial parts of crop plants such as potatoes, oilseed rape, sunflowers and soybeans. This allows completely mechanical harvesting of these important crop plants.

Also of economic interest is facilitated harvesting, which is made possible by concentrating, over a period of time, dehiscence, or reduced adhesion to the tree, in the case of citrus fruit, olives or other species and varieties of pomaceous fruit, stone fruit and nuts. The same mechanism, ie. promotion of the formation of abscission tissue between fruit or leaf and shoot of the plants, is also essential for readily controllable defoliation of useful plants, in particular cotton.

Moreover, a shortened period of time within which the individual cotton plants ripen results in an increased fiber quality after harvesting.

The compounds I, or the compositions comprising them, can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring. The use forms depend on the intended purposes; in any case, they should guarantee the finest possible distribution of the active ingredients according to the invention.

Suitable inert additives are essentially: mineral oil fractions of medium to high boiling point such as kerosene and diesel oil, furthermore coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone or strongly polar solvents, eg. amines such as N-methylpyrrolidone or water.

Aqueous use forms can be prepared from emulsion concentrates, suspensions, pastes, wettable powders or water-dispersible granules by adding water. To prepare emulsions, pastes or oil dispersions, the substituted hydroximic acid derivatives as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

Suitable surfactants are the alkali metal, alkaline earth metal and ammonium salts of aromatic sulfonic acids, eg. ligno-, phenol-, naphthalene- and dibutylnaphthalenesulfonic acid, and of fatty acids, of alkyl- and alkylaryl sulfonates, of alkyl sulfates, lauryl ether sulfates and fatty alcohol sulfates, and salts of sulfated hexa-, hepta- and octadecanols, and of fatty alcohol glycol ether, condensates of sulfonated naphthalene and its derivatives with formaldehyde, condensates of naphthalene, or of the naphthalenesulfonic acids, with phenol and formaldehyde, polyoxyethylene octylphenyl ether, ethoxylated isooctyl-, octyl- or nonylphenol, alkylphenyl and tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or concomitantly grinding the active substances with a solid carrier.

Granules, eg. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The concentrations of the active ingredients I in the ready-to-use products can be varied within wide ranges. In general, the formulations comprise approximately from 0.001 to 98% by weight, preferably 0.01 to 95% by weight, of at least one active ingredient. The active ingredients are normally employed in a purity of from 90% to 100%, preferably 95% to 100% (according to NMR spectrum).

The formulation examples below illustrate the preparation of such formulations:

I. 20 parts by weight of an uracil substituted phenyl sulfamoyl carboxamide I are dissolved in a mixture composed of 80 parts by weight of alkylated benzene, 10 parts by weight of the adduct of 8 to 10 mol of ethylene oxide and 1 mol of oleic acid N-monoethanolamide, 5 parts by weight of calcium dodecylbenzenesulfonate and 5 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

II. 20 parts by weight of an uracil substituted phenyl sulfamoyl carboxamide I are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

III. 20 parts by weight of an uracil substituted phenyl sulfamoyl carboxamide I are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

IV. 20 parts by weight of an uracil substituted phenyl sulfamoyl carboxamide I are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel and the mixture is ground in a hammer mill. Finely distributing the mixture in 20,000 parts by weight of water gives a spray mixture which comprises 0.1% by weight of the active ingredient.

V. 3 parts by weight of an uracil substituted phenyl sulfamoyl carboxamide I are mixed with 97 parts by weight of finely divided kaolin. This gives a dust which comprises 3% by weight of the active ingredient.

VI. 20 parts by weight of an uracil substituted phenyl sulfamoyl carboxamide I are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of an uracil substituted phenyl sulfamoyl carboxamide I is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of an uracil substituted phenyl sulfamoyl carboxamide I is dissolved in a mixture composed of 80 parts by weight of cyclohexanone and 20 parts by weight of Wettol® EM 31 (non-ionic emulsifier based on ethoxylated castor oil; BASF AG). This gives a stable emulsion concentrate.

The active ingredients I, or the herbicidal compositions comprising them, can be applied pre- or post-emergence. If the active ingredients are less well tolerated by certain crop plants, application techniques may be used in which the herbicidal compositions are sprayed, with the aid of the spray apparatus, in such a way that they come into as little contact as possible, if any, with the leaves of the sensitive crop plants while reaching the leaves of undesirable plants which grow underneath, or the bare soil (post-directed, lay-by).

Depending on the intended aim of the control measures, the season, the target plants and the growth stage, the application rates of active ingredient are from 0.001 to 3.0, preferably 0.01 to 1 kg/ha active substance (a.s.).

To widen the spectrum of action and to achieve synergistic effects, the substituted hydroximic acid derivatives I can be mixed and applied jointly with a large number of representatives of other groups of herbicidally or growth-regulatory active ingredients. Suitable components in mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-aroyl-1,3-cyclohexanediones, hetaryl aryl ketones, benzylisoxazolidinones, meta-$CF_3$-phenylderivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4, 5,6-tetrahydrophthalimides, oxadiazoles, oxiranes, phenols, aryloxy- or hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Moreover, it may be advantageous to apply the compounds I, alone or in combination with other herbicides, in the form of a mixture with additional other crop protection agents, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates can also be added.

PREPARATION EXAMPLES

In order to facilitate a further understanding of the invention, the following examples are presented to illustrate more specific details thereof. The term NMR designates nuclear magnetic resonance; HPLC designates high performance liquid chromatography; TLC designates thin layer chromatography; GLC designates gas-liquid chromatography and IR designates infrared spectroscopy.

Example 1

Preparation of 2-Chloro-4-fluoro-5-nitrobenzoic Acid

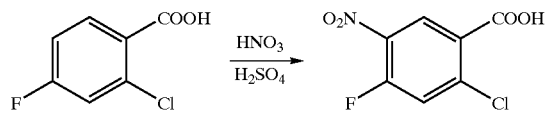

A solution of 2-chloro-4-fluorobenzoic acid (24.4 g, 0.142 mol) in 150 ml of concentrated sulfuric acid at 0° C. was treated dropwise with 90% nitric acid (13.2 ml, 20 mol %, 0.284 mol) over a 10 min. period at 10° C., stirred for 2.5 hours at 0 to 10° C., poured onto one liter of ice. The white solid was filtered. The filtercake was air-dried and recrystallized from ethyl acetate/heptane to afford the title compound as off-white needles. Yield: 18.0 g (58.1%); identified by NMR spectral analysis.

Example 2

Preparation of 2-Chloro-4-fluoro-5-aminobenzoic acid

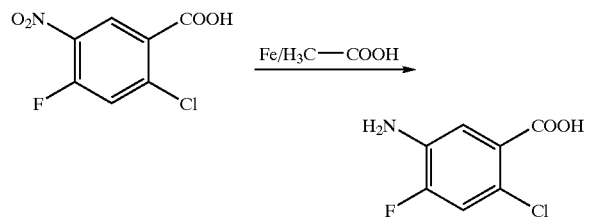

A solution of 2-chloro-4-fluoro-5-nitrobenzoic acid (18.0 g, 0.0824 mol) in 75 ml of acetic acid was heated at reflux temperature. Iron powder (18.4 g, 0.328 mol) was added in several portions and the resulting suspension was cooled to room temperature and diluted with water and ethyl acetate. The mixture was filtered and the filtrate was saved. The organic layer was washed with brine, dried over anhydrous magnesium sulfate and concentrated under reduced pressure to afford the title compound as a tan solid. Yield: 9.00 g (58.1%); mp.: 153–155° C.; identified by NMR and mass spectral analysis.

Example 3

Preparation of 3-(5-Carboxy-4-choro-2-fluorophenyl)-1,2,3,4-dihydro-6-trifluoromethylpyrimidin-2,4-dione

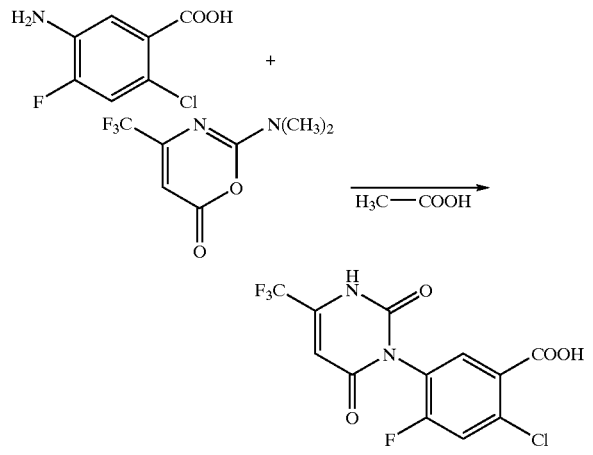

A mixture of 2-chloro-4-fluoro-5-aminobenzoic acid (8.30 g, 0.04308 mol), 2-dimethylamino-4-(trifluoromethyl)-6H-1,3-oxazin-6-one (9.57 g, 0.0460 mol) and acetic acid was stirred three hours at reflux temperature, diluted with ice water and extracted twice with ethyl acetate. The combined organic layers were washed with brine, dried over anhydrous magnesium sulfate and concentrated under reduced pressure to afford the title compound as a tan solid. Yield: 14.0 g (92.1%); identified by NMR and mass spectral analysis.

Example 4

Preparation of 3-(5-Carboxymethoxy-4-choro-2-fluoro-phenyl)-1,2,3,4-dihydro-1-methyl-6-trifluoromethylpyrimidin-2,4-dione

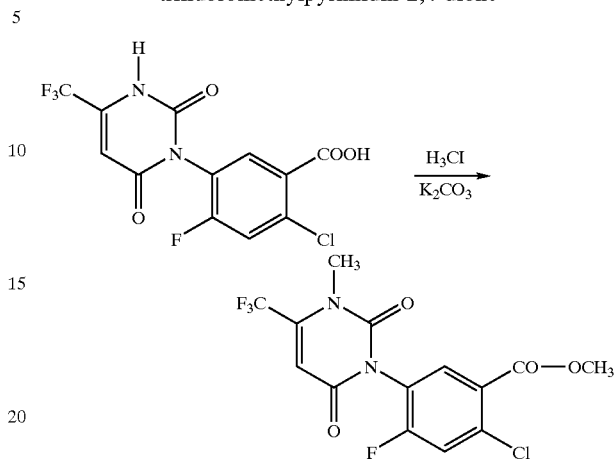

A mixture of 3-(5-carboxy-4-choro-2-fluorophenyl)-1,2,3,4-dihydro-6-trifluoromethylpyrimidin-2,4-dione (13.3 g, 0.0377 mol), potassium carbonate (13.0 g, 0.0943 mol), methyl iodide (5.87 ml, 0.0943 mol) and dimethyl formamide (150 ml) was stirred overnight at room temperature and diluted with water (500 ml). The resulting mixture was extracted three times with ethyl acetate. The combined organic layers were washed three times with water, aqueous sodium hydroxide (0.1 N) and brine, dried over anhydrous magnesium sulfate and concentrated under reduced pressure to give a beige solid. Recrystallization of the residue from ethanol-water (250 ml) afforded the title compound as white needles. Yield: 11.5 g (80.4%); mp.: 172–173° C.; identified by NMR and mass spectral analysis.

Example 5

Preparation of 3-(5-Carbomethoxy-4-chloro-2-fluoro-phenyl)-1,2,3,4-dihydro-6-trifluoromethylpyrimidin-2,4-dione

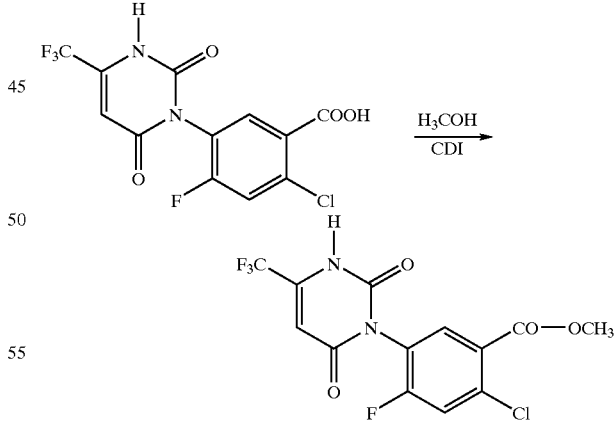

Carbonyl diimidazole (2.97 g, 18.4 mmol) was added to a solution of 3-(5-carboxy-4-chloro-2-fluorophenyl)-1,2,3,4-dihydro-6-trifluoromethylpyrimidin-2,4-dione (4.61 g, 13.1 mmol) in tetrahydrofuran and the resulting mixture was heated to reflux temperature, stirred two minutes and cooled to room temperature. Methanol (2.70 ml, 66.6 mmol) was added and the mixture was stirred overnight at room temperature. Subsequently, the mixture was concentrated under reduced pressure and the resultant residue was taken up in methylene chloride. The organic mixture was washed twice with hydrochloric acid (10% aqueous and 5% aqueous) and water. The organic layer was concentrated under reduced spectral analysis.

Example 4

Preparation of 3-(5-Carboxymethoxy-4-choro-2-fluoro-phenyl)-1,2,3,4-dihydro-1-methyl-6-trifluoromethylpyrimidin-2,4-dione

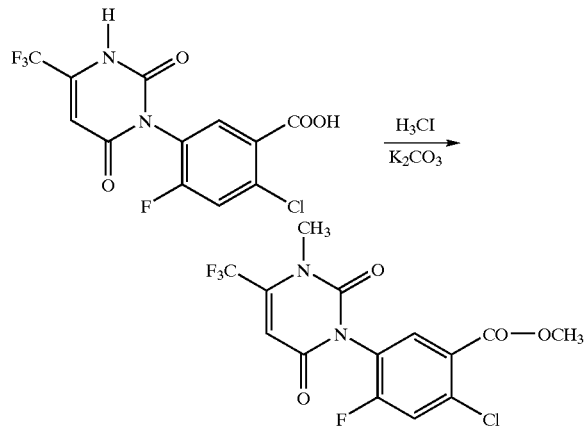

A mixture of 3-(5-carboxy-4-choro-2-fluorophenyl)-1,2,3,4-dihydro-6-trifluoromethylpyrimidin-2,4-dione (13.3 g, 0.0377 mol), potassium carbonate (13.0 g, 0.0943 mol), methyl iodide (5.87 ml, 0.0943 mol) and dimethyl formamide (150 ml) was stirred overnight at room temperature and diluted with water (500 ml). The resulting mixture was extracted three times with ethyl acetate. The combined organic layers were washed three times with water, aqueous sodium hydroxide (0.1 N) and brine, dried over anhydrous magnesium sulfate and concentrated under reduced pressure to give a beige solid. Recrystallization of the residue from ethanol-water (250 ml) afforded the title compound as white needles. Yield: 11.5 g (80.4%); mp.: 172–173° C.; identified by NMR and mass spectral analysis.

Example 5

Preparation of 3-(5-Carbomethoxy-4-chloro-2-fluoro-phenyl)-1,2,3,4-dihydro-6-trifluoromethylpyrimidin-2,4-dione

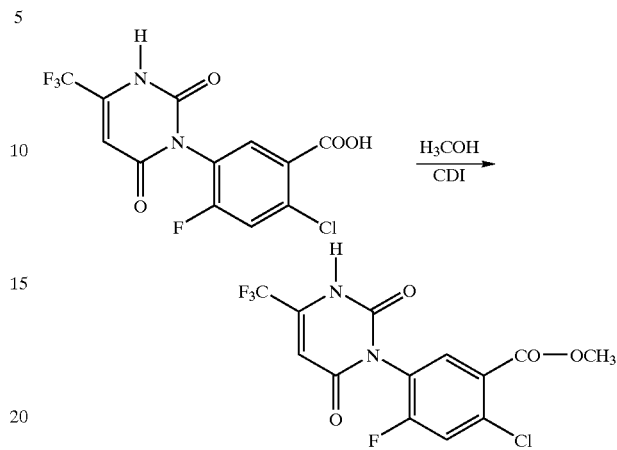

Carbonyl diimidazole (2.97 g, 18.4 mmol) was added to a solution of 3-(5-carboxy-4-chloro-2-fluorophenyl)-1,2,3,4-dihydro-6-trifluoromethylpyrimidin-2,4-dione (4.61 g, 13.1 mmol) in tetrahydrofuran and the resulting mixture was heated to reflux temperature, stirred two minutes and cooled to room temperature. Methanol (2.70 ml, 66.6 mmol) was added and the mixture was stirred overnight at room temperature. Subsequently, the mixture was concentrated under reduced pressure and the resultant residue was taken up in methylene chloride. The organic mixture was washed twice with hydrochloric acid (10% aqueous and 5% aqueous) and water. The organic layer was concentrated under reduced pressure to give a brown solid, which was suspended in methylene chloride, followed by filtration. The filtercake was washed three times with methylene chloride, filtered and dried to afford the title compound as a white solid, which was identified by NMR spectral analysis. Yield: 4.27 g (89.0%).

Example 6

Preparation of 3-(5-Carbomethoxy-4-chloro-2-fluoro-phenyl)-1,2,3,4-dihydro-1-amino-6-trifluoromethylpyrimidin-2,4-dione

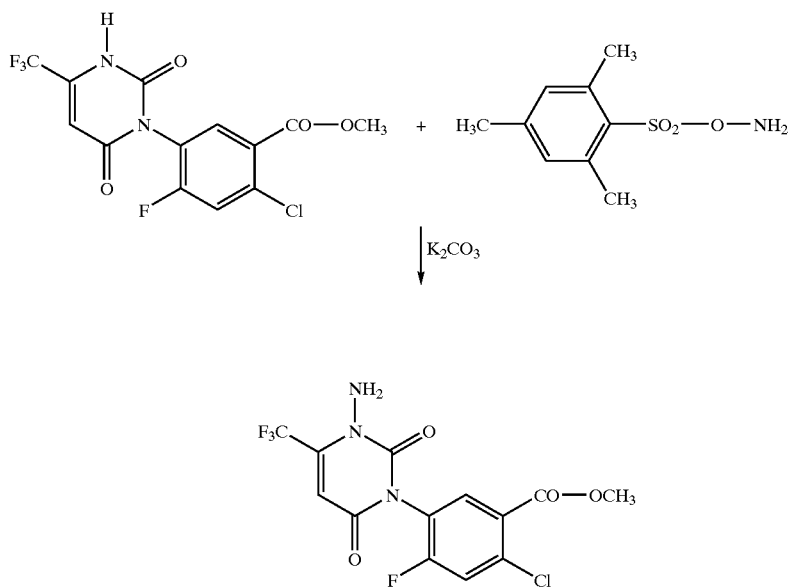

To a suspension of 3-(5-carbomethoxy-4-chloro-2-fluorophenyl)-1,2,3,4-dihydro-6-trifluoromethylpyrimidin-2,4-dione (4.24 g, 11.6 mmol) in anhydrous tetrahydrofuran was added potassium carbonate (1.60 g, 11.6 mmol) followed by O-mesitylenesulfonyl hydroxylamine (3.04 g, 14.1 mmol; J. G. Krause, Synthesis, 1972, 140). The resulting mixture was stirred overnight at room temperature and diluted with water. The mixture was extracted four times with ethyl acetate. The combined extracts were dried over anhydrous magnesium sulfate and concentrated under reduced pressure to afford the title compound as a foam, which was identified by NHR spectral analysis. Yield: 4.63 g (>100%).

Example 7

Preparation of 3-(5-Carboxy-4-chloro-2-fluorophenyl)-1,2,3,4-dihydro-1-amino-6-trifluoromethylpyrimidin-2,4-dione

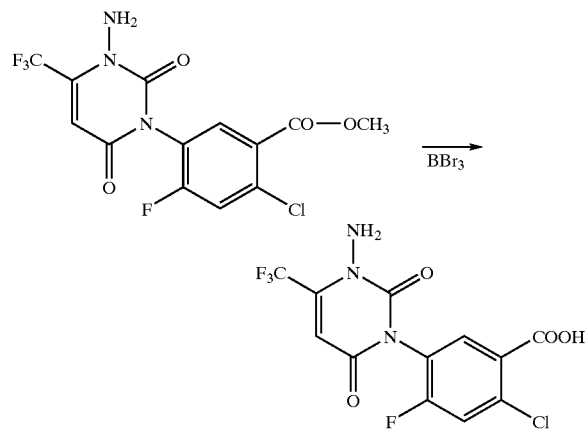

To a solution of 3-(5-carbomethoxy-4-chloro-2-fluorophenyl)-1,2,3,4-dihydro-1-amino-6-trifluoromethylpyrimidin-2,4-dione (1.53 g, 4.01 mmol) in anhydrous methylene chloride was added boron tribromide (1M in methylene chloride, 16.0 ml, 16.0 mmol). The resultant mixture was stirred overnight at room temperature and then diluted with water. The aqueous layer was separated and allowed to stand at room temperature overnight; filtration and drying afforded the title compound as a white solid, which was identified by NHR and mass spectral analysis. Yield: 0.61 g (41.5%).

The original organic layer was concentrated under reduced pressure to a glassy solid, which was triturated with water to afford an additional amount of the title compound as a tan solid, which was identified by NMR and mass spectral analysis. Yield: 0.310 g (21.1%); mp.: 150° C. (decomposition).

Example 8

Preparation of 3-(5-carboxy-4-chloro-2-fluorophenyl)-1,2,3,4-dihydro-1-methyl-6-trifluoromethylpyrimidin-2,4-dione

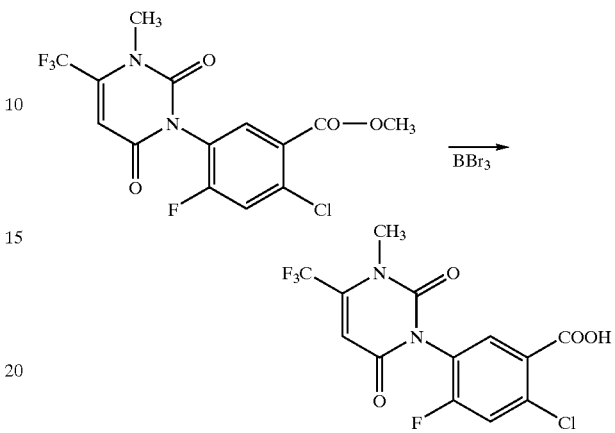

Boron tribromide (84.0 ml, 0.0840 mol, 1M in methylene chloride) was added dropwise to a mixture of 3-(5-carbomethoxy-4-chloro-2-fluorophenyl)-1,2,3,4-dihydro-1-methyl-6-trifluoromethylpyrimidin-2,4-dione (10.7 g, 0.0281 mol) and methylene chloride (150 ml). The resulting mixture wan stirred overnight at room temperature and diluted with ice water. The organic layer is saved and the aqueous layer was extracted twice with ethyl acetate. The extracts were combined with the organic layer, washed with brine, dried over anhydrous magnesium sulfate and concentrated under reduced pressure to afford the title compound as a white solid, which was identified by NMR and mass spectral analysis. Yield: 10.2 g (100%); mp.: 240–241° C.

Example 9

Preparation of S-Chlorosulfonamide

Formic acid (10.9 ml, 0.287 mol) was added dropwise over a two hour period to chlorosulfonyl isocyanate (25.0 ml, 0.287 mol), maintaining the temperature below 20° C. The resulting suspension was stirred two hours at 20° C. and diluted with anhydrous toluene (100 ml). The resulting mixture was stirred overnight at ambient temperature and filtered. The filtrate was concentrated under reduced pressure to afford the title compound as an off-white solid, which was identified by IR spectral analysis. Yield: 32.1 g (97.3%).

Example 10

Preparation of N-Methylsulfamide

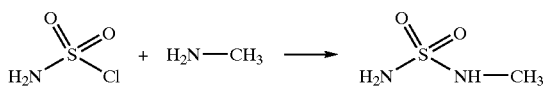

A solution of S-chlorosulfonamide (3.00 g, 0.0260 mol) in tetrahydrofuran (10 ml) was added dropwise to methylamine (40 ml, 2M in tetrahydrofuran) at 10° C. The resulting mixture was stirred one hour at 0° C. and three days at room temperature. The suspension was filtered and the filtrate concentrated under reduced pressure to give a yellow solid. Chromatography on silica gel (9:1 methylene chloride—methanol) afforded the title compound as an off-white solid, which was identified by NMR and mass spectral analysis. Yield: 1.36 g (47.4%).

Examples 11–15

Preparation of N-substituted sulfamides

Using essentially the same procedure as described in Example 10 hereinabove and substituting the appropriate amine starting material, the following compounds are prepared:

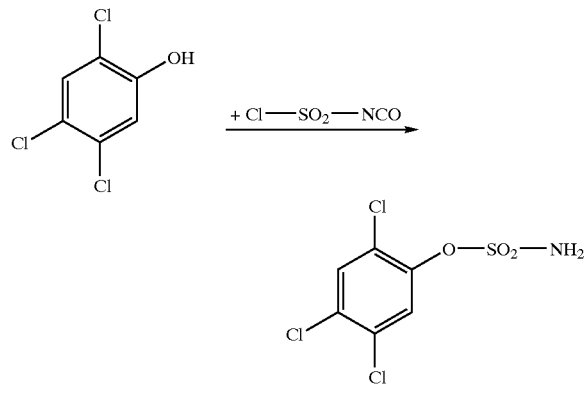

| Example | $R^1$ | $R^2$ | mp. [° C.] |
|---|---|---|---|
| 11 | H | $CH_2$—$C(CH_3)_3$ | — |
| 12 | $CH_3$ | $CH_2$—$CH$=$CH_2$ | 36–38 |
| 13 | $CH_3$ | benzyl | 91–94 |
| 14 | $CH(CH_3)_2$ | $CH(CH_3)_2$ | — |
| 15 | H | H | — |

Example 16

Preparation of O-2,4,5-trichlorophenyl sulfamate

A solution of 2,4,5-trichlorophenol (96.0 g, 0.486 mol) in toluene (95 ml) was treated dropwise with chlorosulfonyl isocyanate (67.4 g, 0.476 mol) at 40–50° C. The resulting mixture was stirred three hours at reflux temperature, cooled to 40° C. and quenched with water until gas evolution ceases. The suspension was filtered and the filtercake was air-dried to afford the title compound as a white solid, which is identified by NMR and IR spectral analysis. Yield; 118.5 g (90.0%).

Example 17

Preparation of N-methyl-N-isopropyl sulfamide

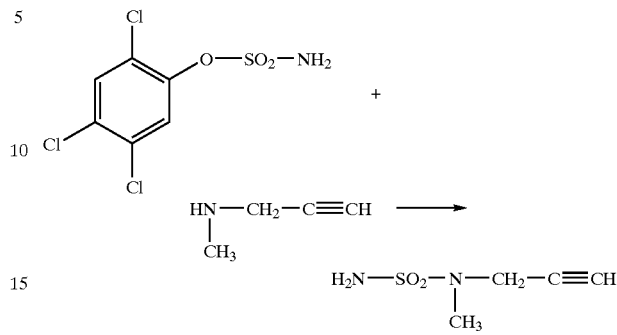

Triethylamine (2.50 ml, 0.0181 mol) was added to a solution of methyl propargylamine (1.55 ml, 0.0181 mol) in acetonitrile. To the resulting mixture was added O-2,4,5-trichlorophenyl sulfamate (5.00 g, 0.0181 mol). The resulting mixture was stirred for one hour at room temperature and filtered through silica gel with methylene chloride. The filtrate was concentrated under reduced pressure to afford a white solid. Chromatography of the residue on silica gel (0.5% methanol-methylene chloride) afforded the title compound, which was identified by NMR spectral analysis. Yield: 1.84 g (68.7%).

Examples 18–52

Preparation of N-Substituted Sulfamides

Using essentially the same procedure as described in Example 17 hereinabove and substituting the appropriate amine starting material, the following sulfamides were prepared:

| | $H_2N$—$SO_2$—$NR^1R^2$ | | |
|---|---|---|---|
| Example | $R^1$ | $R^2$ | mp. [° C.]/ $^1H$—NMR [ppm] |
| 18 | $CH_3$ | $CH_3$ | — |
| 19 | $CH_3$ | 3-chlorobenzyl | — |
| 20 | $CH_3$ | $CH_2$—$C_2H_5$ | — |
| 21 | $C_2H_5$ | $C_2H_5$ | 39–41 |
| 22 | H | $CH(CH_3)$—$C_2H_5$ | — |
| 23 | $CH_3$ | $C_2H_5$ | 32–34 |
| 24 | H | $C(CH_3)_3$ | 49–53 |
| 25 | H | $CH_2$—$C_2H_5$ | 32–35 |
| 26 | $CH_3$ | 3-methoxybenzyl | — |
| 27 | $CH_3$ | $CH_2$—$CH(CH_3)_2$ | 103–104 |
| 28 | H | $CH(CH_3)_2$ | — |
| 29 | $CH_3$ | $CH(CH_3)_2$ | 63–65 |
| 30 | H | $C_2H_5$ | — |
| 31 | $C_2H_5$ | $CH_2$—$C_2H_5$ | — |
| 32 | H | $CH_2$—$CH_2$—$CH(CH_3)_2$ | — |
| 33 | $CH_3$ | $CH_2$—$CH_2$-phenyl | — |
| 34 | $CH_3$ | phenyl | 84–86 |
| 35 | H | $CH_2$—C≡CH | — |
| 36 | H | $CH_2$-(2-furyl) | 62–64 |
| 37 | $CH_3$ | $CH(CH_3)$—$C_2H_5$ | — |
| 38 | H | $CH_2$-(2-thienyl) | 93–96 |
| 39 | H | cyclopentyl | 55 |
| 40 | H | 4-methoxybenzyl | — |
| 41 | $CH_3$ | $CH_2$—$CH_2$—$C_2H_5$ | — |
| 42 | $CH_3$ | $CH_2$—$CH_2$—CN | — |
| 43 | $CH_3$ | $CH_2$-(1,3-dioxalanyl) | — |

-continued

H₂N—SO₂—NR¹R²

| Example | R¹ | R² | mp. [° C.]/ ¹H—NMR [ppm] |
|---|---|---|---|
| 44 | H | 4-chlorobenzyl | — |
| 45 | CH₃ | C(CH₃)₃ | 54–57 |
| 46 | —CH₂—CH=CH—CH₂— | | — |
| 47 | H | cyclopropyl | 58–60 |
| 48 | —CH₂—CH₂—CH₂—CH₂— | | 84–86 |
| 49 | CH₃ | cyclopropyl | — |
| 50 | C₂H₅ | CH(CH₃)₂ | — |
| 51 | H | CH₂—CH(CH₃)₂ | — |
| 52 | H | CH₂—CH₂—C₂H₅ | — |
| 53 | CH₃ | CH₂—CO—OC₂H₅ | 5.1(br., s, 2H), 4.25(q, 2H), 4.1(s, 2H), 3.0(s, 3H), 1.3(t, 3H) |

Example 54

Preparation of 3-(5-(N,N-dimethyl)sulfamoylcarboxamido-4-chloro-2-fluorophenyl)-1,2,3,4-dihydro-6-trifluoromethylpyrimidin-2,4-dione

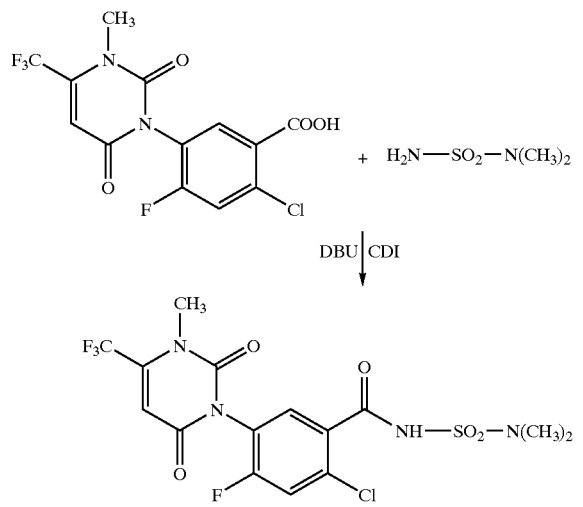

To a solution of 3-(5-carboxy-4-chloro-2-fluorophenyl)-1,2,3,4-dihydro-1-methyl-6-(trifluoromethyl)pyrimidin-2,4-dione (1.50 g, 4.09 mmol) in tetrahydrofuran was added N,N'-carbonyldiimidazole (1.00 g, 6.14 mol). The resulting mixture was stirred one hour at reflux temperature and cooled to room temperature. Dimethyl sulfamide (0.760 g, 6.14 mmol) was added, followed by diazabicycloundecane (0.930 ml, 6.14 mmol) after 10 min. The resulting mixture was stirred overnight at room temperature and then concentrated under reduced pressure. The resultant residue was partitioned between ethyl acetate and hydrochloric acid (2N). The organic layer was saved and the aqueous phase was extracted three times with ethyl acetate. The extracts were combined with the saved organic layer, washed with 10% sodium bicarbonate, dried over anhydrous magnesium sulfate and concentrated under reduced pressure to give a first residue.

The aqueous phase was acidified and extracted with ethyl acetate.

The organic layers were dried and concentrated under reduced pressure to give a second residue.

The residues were combined and washed with ethyl acetate to afford the title compound as a white solid, which was identified by NMR and mass spectral analysis. Yield: 0.61 g (42.0%); mp. 213–214° C.

Examples 55–93

Preparation of 3-[5-(N-substituted)sulfamoylcarboxamido-4-chlorophenyl)-1,2,3,4-dihydro-6-(trifluoromethyl)pyrimidin-2,4-diones Using essentially the above same procedure as described in Example 54 and substituting the appropriate sulfamide starting material, the following compounds were obtained:

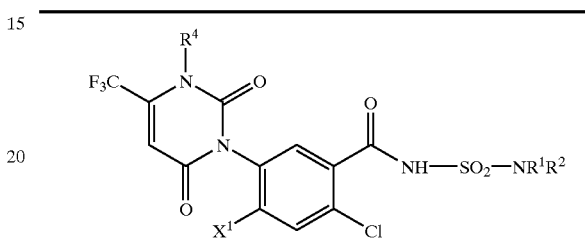

| Example No. | x¹ | R¹ | R² | R²⁹ | mp. [° C.] |
|---|---|---|---|---|---|
| 55 | F | CH₃ | 3-chlorobenzyl | CH₃ | 78–79 |
| 56 | F | H | CH₃ | CH₃ | 232–233 |
| 57 | F | CH₃ | CH₂—C≡CH | CH₃ | 195–196 |
| 58 | F | H | H | CH₃ | 141–142 |
| 59 | F | CH₃ | allyl | CH₃ | 189 |
| 60 | F | CH(CH₃)₂ | CH(CH₃)₂ | CH₃ | 81–82 |
| 61 | F | CH₃ | benzyl | CH₃ | 90–91 |
| 62 | F | C₂H₅ | CH₂—C₂H₅ | CH₃ | 74–76 |
| 63 | F | H | CH₂—C₂H₅ | CH₃ | 206–207 |
| 64 | F | H | CH(CH₃)—C₂H₅ | CH₃ | 221 |
| 65 | F | H | C(CH₃)₃ | CH₃ | 115 |
| 66 | F | CH₃ | C₂H₅ | CH₃ | 215–216 |
| 67 | F | CH₃ | CH₂—C₂H₅ | CH₃ | 72 |
| 68 | F | C₂H₅ | C₂H₅ | CH₃ | 210–211 |
| 69 | F | CH₃ | CH(CH₃)—C₂H₅ | CH₃ | 74 |
| 70 | F | CH₃ | 3-methoxybenzyl | CH₃ | 79 |
| 71 | F | H | CH₂—C≡CH | CH₃ | 195–196 |
| 72 | F | H | CH₂—CH₂—CH(CH₃)₂ | CH₃ | 222–223 |
| 73 | F | CH₃ | phenyl | CH₃ | 104–105 |
| 74 | F | CH₃ | CH₂—CH₂-phenyl | CH₃ | 90–91 |
| 75 | F | CH₃ | phenyl | NH₂ | 120–142 |
| 76 | F | CH₃ | CH(CH₃)₂ | NH₂ | 117–120 |
| 77 | F | H | CH₂-(2-thienyl) | CH₃ | 127–128 |
| 78 | F | H | cyclopentyl | CH₃ | 232–233 |
| 79 | F | H | CH(CH₃)₂ | CH₃ | 221 |
| 80 | F | H | C₂H₅ | CH₃ | 211 |
| 81 | F | H | CH₂-(2-furyl) | CH₃ | 178–180 |
| 82 | F | H | 4-methoxybenzyl | CH₃ | 186–188 |
| 83 | F | CH₃ | CH₂—CH₂—C₂H₅ | CH₃ | 156–157 |
| 84 | F | CH₃ | CH₂—CH₂—CN | CH₃ | 99–103 |
| 85 | F | CH₃ | CH₂-(1,3-dioxolanyl) | CH₃ | 93–96 |
| 86 | F | H | 4-chlorobenzyl | CH₃ | 95–99 |
| 87 | F | CH₃ | C(CH₃)₃ | CH₃ | 126 |
| 88 | F | —CH₂—CH=CH—CH₂— | | CH₃ | 231 |
| 89 | F | H | cyclopropyl | CH₃ | 208 |
| 90 | F | —CH₂—CH₂—CH₂—CH₂— | | CH₃ | 230 |
| 91 | F | CH₃ | cyclopropyl | CH₃ | 156 |
| 92 | F | C₂H₅ | CH(CH₃)₂ | CH₃ | 146 |
| 93 | F | H | CH₂—CH(CH₃)₂ | CH₃ | 202 |
| 94 | F | H | CH₂—CH₂—C₂H₅ | CH₃ | 227 |
| 95 | H | CH₃ | Phenyl | CH₃ | 108–110 |
| 96 | F | CH₃ | 4-(methoxycarbonyl)phenyl | CH₃ | 102 |
| 97 | F | C₂H₅ | Phenyl | CH₃ | 214–215 |
| 98 | F | CH₃ | 3-Pyridyl | CH₃ | 208 |
| 99 | F | CH₃ | 3,4-dichlorophenyl | CH₃ | 118 |
| 100 | F | CH₃ | 3-chlorophenyl | CH₃ | 183–184 |
| 101 | F | CH₃ | CH(CH₃)₂ | CH₃ | 93–95 |
| 102 | F | CH₃ | CH₃ | NH₂ | 252 |

-continued

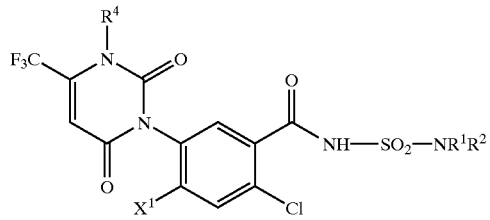

| Example No. | $X^1$ | $R^1$ | $R^2$ | $R^{29}$ | mp. [° C.] |
|---|---|---|---|---|---|
| 103 | H | $CH_3$ | $CH_2$—C≡CH | $CH_3$ | 228.2–229.0 |
| 104 | F | $CH_3$ | 4-(methoxy)phenyl | $CH_3$ | 136–138 |
| 105 | F | $CH_3$ | 4-chlorophenyl | $CH_3$ | 110–111 |
| 106 | F | $CH_3$ | 4-nitrophenyl | $CH_3$ | 111–112 |
| 107 | F | $CH_3$ | 4-methylphenyl | $CH_3$ | 102 |
| 108 | H | H | H | $CH_3$ | 143.5–145.8 |
| 109 | H | $CH_3$ | $CH_2$—$C_2H_5$ | $CH_3$ | 187.0–189.5 |
| 110 | H | $CH_3$ | $C_2H_5$ | $CH_3$ | 245.5–246.0 |
| 111 | H | $CH_3$ | $CH_2$—$CH(CH_3)_2$ | $CH_3$ | 164.1–164.7 |
| 112 | H | $C_2H_5$ | $C_2H_5$ | $CH_3$ | 244.4–245.4 |
| 113 | H | $CH_3$ | $CH_2$—$CH_2$—$C_2H_5$ | $CH_3$ | 167.9–172.0 |
| 114 | H | $CH_3$ | $CH_3$ | $CH_3$ | 228.8–231.5 |
| 115 | F | $CH_3$ | 2-methylphenyl | $CH_3$ | 125–127 |
| 116 | F | $CH_3$ | 3-methylphenyl | $CH_3$ | 187–189 |
| 117 | F | $CH_3$ | α-naphthyl | $CH_3$ | 131–133 |
| 118 | F | $CH_3$ | 2,4-difluorophenyl | $CH_3$ | 118–119 |
| 119 | F | $CH_3$ | 2-chlorophenyl | $CH_3$ | 133 |
| 120 | F | $CH_3$ | 2-(trifluoromethyl)phenyl | $CH_3$ | 98–106 |
| 121 | H | $CH_3$ | 4-(phenoxy)phenyl | $CH_3$ | 95 |
| 122 | F | $CH_3$ | 4-(trifluoromethyl)phenyl | $CH_3$ | 133 |
| 123 | F | $CH_3$ | 4-(dimethylamino)phenyl | $CH_3$ | 87 |
| 124 | F | $CH_3$ | 4-diphenyl | $CH_3$ | 125–133 |
| 125 | F | $CH_3$ | $CH(CH_3)$—$C_2H_5$ | $NH_2$ | yellow glass |
| 126 | F | $CH_3$ | $C(CH_3)_3$ | $NH_2$ | yellow glass |
| 127 | F | $CH_3$ | $CH_2$—$CH(CH_3)_2$ | $NH_2$ | yellow glass |
| 128 | F | $CH(CH_3)_2$ | $CH(CH_3)_2$ | $NH_2$ | yellow glass |
| 129 | F | $CH_3$ | 3-(methoxy)phenyl | $CH_3$ | 86 |
| 130 | H | $CH_3$ | 4-fluorophenyl | $CH_3$ | 120 |
| 131 | F | $CH_3$ | 3-(dimethylamino)phenyl | $CH_3$ | 85 |
| 132 | F | $CH_3$ | 3,5-(dichloro)phenyl | $CH_3$ | 104 |
| 133 | F | $CH_3$ | $CH_2$—CO—$OC_2H_5$ | $CH_3$ | 118–119 |
| 134 | F | $CH_3$ | indanyl | | 112 |

Example 135

Preparation of N'-{2-chloro-4-fluoro-5-[4-(difluoromethyl)-4,5-dihydro-3-methyl-5-oxo-1H-1,2,4-triazol-1-yl]-benzoyl}-N-isopropyl-N-methylsulfamide Step 1: 2-(2-Fluoro-4-chloro-5-carbomethoxyphenylhdrazonyl)propionic acid A solution of pyruvic acid (3.92 g, 44.5 mmol) in water (4 ml) was added to a mixture of hydrazine x1 (18.00 g, 36.6 mmol), ethanol (240 ml) and hydrochloric acid (10% strength, 37 ml). The mixture was stirred for 35 minutes at 45–60° C., cooled to 30° C. and filtered. The filtrate was concentrated under reduced pressure to –50% of the original volume and added slowly to water (700 ml). The resultant suspension was stirred for 20 minutes and filtered. The title compound was obtained as a yellow solid. Yield: 9.60 g (90.9%)

Step 2: 2-chloro-4-fluoro-5-[4,5-dihydro-3-methyl-5-oxo-1H-1,2,4-triazol-1-yl]-benzonic acid methyl ester A mixture of the hydrazone from step 1 (9.00 g, 31.0 mmol) and triethylamine (4.35 ml, 31.0 mmol) was heated to 50° C. and treated with a mixture of azide 12 (7.98 g, 29.0 mmol) and toluene (10ml). The resultant mixture was stirred for 100 minutes at 50° C., cooled to room temperature and concentrated under reduced pressure. The residue was partitioned between water and ethyl acetate. The organic layer was dried and concentrated under reduced pressure to give the title compound as an off-white solid, which was used in the next step without further purification. Yield: 6.35 g (71.9%).

Step 3: 2-Chloro-4-fluoro-5-[4-(difluoromethyl)-4,5-dihydro-3-methyl-5-ox o-1H-1,2,4-triazol-1-yl]-benzoic acid methylester An excess of chlorodifluoromethane (97 g) was bubbled into a mixture of triazolinone from step 2 (7.04 g, 24.6 mmol), tetrabutylammonium bromide (9.67 g, 30.0 mmol), potassium carbonate (16.6 g, 122 mmol) and dimethylformamide (200 ml) in such a way that T<36° C. over a period of 30 minutes. The mixture was cooled and filtered. The filtrate was concentrated under reduced presssure and the residue partitioned between water and methylene chloride. The organic layer was washed with water, dried and concentrated under reduced pressure to give a dark oil (9.00 g), which was chromatographed on silica gel (eluent: ethyl acetate/hexane) to give the title compound. Yield: 1.48 g (17.9%).

Step 4: 2-Chloro-4-fluoro-5-[4-(difluoromethyl)-4,5-dihydro-3-methyl-5-oxo-1H-1,2,4-triazol-1-yl]-benzoic acid (IIba)

A mixture of ester II with Q=$Q^5$; $R^7$=$CHF_2$, $A^4$=O, $R^8$=$CH_3$, $X^1$=F and $X^2$=Cl (0.950 g, 2.83 mmol), acetic acid (10 ml) and hydrochloric acid (6N, 5.0 ml) was stirred for 24 hours at 64–100° C., cooled to room temperature and concentrated under reduced pressure. The residue was partitioned between methylene chloride and water. The organic layer was washed twice with water, dried and concentrated under reduced pressure to yield the title compound as a pale yellow solid. Yield: 0.42 g (46%); mp.: 132–135° C.

Step 5: N'-[[2-chloro-4-fluoro-5-[4-(difluoromethyl)-4,5-dihydro-3-methyl-5-oxo-1H-1,2,4-triazol-1-yl]-benzoyl]]-N-isopropyl-N-methylsulfamide A mixture of acid II (0.370 g, 1.15 mmol), the sulfamide (0.210 g, 1.38 mmol), carbonyl diimidazole (0.244 g, 1.50 mmol), DBU (0.228 g, 1.50 mmol) and tetrahydrofuran was stirred for four days at ambient temperature. The resultant mixture was treated with additional sulfamide (0.150 g, 0.986 mmol) and DBU (0.150 g, 0.986 mmol). The mixture was refluxed for two hours, cooled and concentrated under reduced pressure. The residue was taken up in water and acidified with hydrochloric acid (1 N). The mixture was extracted four times with methylene chloride. The combined extracts were washed with water, dried and concentrated under reduced pressure to give a yellow oil, which was chromatographed on silica gel (eluent: ethyl acetate/hexane), yielding the title compound as an off-white solid. Yield: 0.160 g (30.5%); mp.=118–122° C.

Example 136

Preparation of N'-{2-chloro-4-fluoro-5-(5,6,7,8-tetrahydro-3-oxo-1,2,4-triazolo[4,3-a]pyridin-2(3H)-yl)-benzoyl}-N,N-dialkylsulfamide Step 1: 2-Chloro-4-fluoro-5-(5,6,7,8-tetrahydro-3-oxo-1,2,4-triazolo[4,3-a]pyridin-2(3H)-yl)-benzoic acid Boron tribromide (19.4 ml, 19.4 mmol, 1N in methylene chloride) was added dropwise to a mixture of I with A=O, $X^1$=F, $X^2$=Cl, Q=$Q^5$, $A^4$=O and $R^7+R^8$=—$(CH_2)_4$— (1.90 g, 5.54 mmol) and methylene chloride (20 ml). The resultant mixture was stirred overnight at room temperature. Water (40 ml) was added dropwise and the mixture stirred for three hours at room temperature. The organic layer was separated and concentrated under reduced pressure to give the title compound as a pale yellow solid. Yield: 1.34 g (77.4%); mp.: 91–94° C.

Step 2: N'-{2-chloro-4-fluoro-5-(5,6,7,8-tetrahydro-3-oxo-1,2,4-triazolo[4,3-a]pyridin-2(3H)-yl)-benzoyl}-N-isopropyl-N-methyl-sulfenamide Carbonyl diimidazole (0.500 g, 3.08 mmol) was added to a solution of the compound of step 1 (0.640 g, 2.05 mmol) in anhydrous methylene chloride (15 ml). The resultant mixture was stirred for 30 minutes at room temperature, brought to reflux temperature and immediately cooled to room temperature. The sulfamide (0.370 g, 2.46 mmol) and the DBU (0.470 g, 3.08 mmol) were added and the resultant mixture was stirred overnight at room temperature. The mixture was diluted with ethyl acetate (10 ml) and 3% strength hydrochloric acid (15 ml) and stirred for 10 minutes. Removal of the methylene chloride under reduced pressure gives an aqueous residue which was extracted with ethyl acetate. The combined organic layers were washed with water and brine, and dried over anhydrous magnesium sulfate. Concentration under reduced pressure and recrystallization from methylene chloride yielded a solid, which was taken up in methylene chloride and filtered through a column of basic alumina with methanol/methylene chloride, giving the title compound as a white solid. Yield: 0.360 g (39.4%); mp.: 250–251° C.

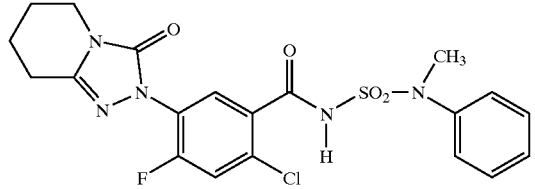

Example 137

Using an identical procedure as described in Example 136 hereinabove and the sulfamide $H_2N$—$SO_2$—N($CH_3$)-phenyl, the following compound was isolated as a white solid of m.p. 200–201° C.:

Example 138

Preparation of N'-[2-chloro-5-(3,5-dimethyl-2,6-dioxo-4-thioxo-1,3,5-triazinan-1-yl)-4-fluorobenzoyl]-N-isopropyl-N-methylsulfamide A solution of 0.502 g (1.45 mmol) of the acid III with $X^1$=F, $X^2$=Cl, Q=$Q^{22}$, $R^{32}$ & $R^{33}$=$CH_3$, $A^{15}$ & $A^{16}$=O and $A^{17}$=S in 5 ml of tetrahydrofuran was treated with 0.283 g (1.74 mmol) of N,N-carbonyl-diimidazole at 60° C. After this solution had been cooled to ambient temperature, a solution of 0.287 g (1.89 mmol) N,N-methyldiisopropylsulfamide and 0.276 g (1.82 mmol) of DBU in 10 ml of tetrahydrofuran was added and the mixture was stirred overnight. After removal of the volatiles under reduced pressure, the crude product was chromatographed on silica gel with ethyl acetate and cyclohexane. Yield: 0.180 mg of the desired product.

$^1$H-NMR (270 MHz; in $CDCl_3$): δ [ppm]=1.25 (d, 6H), 2.95 (s, 3H, $SO_2$—$NCH_3$), 3.8 (s, 6H, $NCH_3$), 4.3 (m, 1H), 7.4 (d, 1H, Ar—H), 7.8 (d, 1H, Ar—H), 8.9 (bs, 1H, NH).

Example 139

Preparation of N'-[2-chloro-4-fluoro-5-(5-trifluoromethylpyridazon-3-on-2-yl)-benzoyl]-N-isopropyl-N-methylsulfenamides Step 1: 2-Fluoro-4-chloro-5-(5-trifluoromethylpyridazin-3-on-2-yl)-benzoic acid Pyridazinone ester II with $X^1$=F, $X^2$=Cl, Q=$Q^{27}$, $R^{34}$=H, $R^{35}$=$CF_3$ and $R^{36}$=H (3 g, 8.56 mmol) was dissolved in anhydrous $CH_2Cl_2$ (100 ml). A solution of $BBr_3$ (30 ml, 1 N in $CH_2Cl_2$, 30 mmol) was added to the solution and the mixture was stirred at room temperature for 17 hours. Water (50 ml) was added and the mixture stirred vigorously for 3 hours. A rotary evaporator was used to remove the $CB_2Cl_2$ and the suspended solid was filtered, washed with water and dried to give 2.76 g of the product as a pale yellow solid. Yield: 95%.

Using an identical procedure, the ester II with $X^1$=F, $X^2$=Cl, Q=$Q^{27}$, $R^{34}$=H, $R^{35}$=$CF_3$ and $R^{36}$=$CH_3$, shown above, was converted to the corresponding acid III in 97% yield.

Step 2: N'-{2-chloro-4-fluoro-5-(5-trifluoromethyl-pyridazon-3-on-2-yl)-benzoyl}-N-isopropyl-N-methylsulfenamides The carboxylic acid III with $X^1$=F, $X^2$=Cl, Q=$Q^{27}$, $R^{34}$=H, $R^{35}$=$CF_3$ and $R^{36}$=$CH_3$ (0.71 g, 2.10 mmol) was dissolved in anhydrous tetrahydrofuran (15 ml) and CDI (0.51 g, 3.15 mmol) was added as a single portion. The mixture was stirred at room temperature for 30 minutes. The mixture was refluxed for 5 minutes, then cooled to room temperature. The sulfamide (0.32 g, 2.10 mmol) was added, followed by DBU (0.48 g, 3.15 mmol). The reaction was stirred at room temperature for 17 hours. 5% strength HCl (15 ml) and ethyl acetate (10 ml) were added to the reaction, and the mixture was stirred vigorously for 10 minutes. The mixture was extracted with ethyl acetate (3×15 ml) and the combined extracts were washed with water, dried over $MgSO_4$ and concentrated in a rotary evaporator to give a brown semi-solid. The crude product was purified by chromatography on a basic alumina column (eluted with $CH_2Cl_2$, 1%, 2% $H_3C$—OH/$CH_2Cl_2$ then 1% acetic acid/$CH_2Cl_2$) to give the final product Ida.xxx (0.45 g) as an off-white solid. Yield: 45%; mp.: 82° C.

The following compounds were prepared using the same procedure and with the appropriate acid and sulfamide.

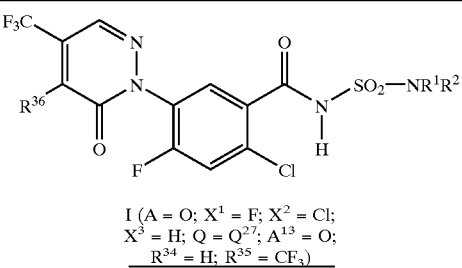

I (A = O; $X^1$ = F; $X^2$ = Cl; $X^3$ = H; Q = $Q^{27}$; $A^{13}$ = O; $R^{34}$ = H; $R^{35}$ = $CF_3$)

| Example No. | $R^1$ | $R^2$ | $R^{36}$ | mp. [° C.] |
|---|---|---|---|---|
| 140 | $CH_3$ | phenyl | H | 182 |
| 141 | $CH_3$ | phenyl | $CH_3$ | 74–75 |
| 142 | $CH_3$ | $CH(CH_3)_2$ | $CH_3$ | 181–182 |
| 143 | $CH_3$ | $CH_3$ | $CH_3$ | 205–206 |
| 144 | $CH_3$ | $CH_3$ | H | 184–186 |

Example 145

Preparation of 4-chloro-3-[4-chloro-2-fluoro-5-(N-methyl-N-isopropyl)-sulfamoylcarboxamidophenyl]-5-difluorormethoxy-1-methyl-1H-pyrazole A solution of 3-[5-carboxy-4-chloro-2-fluorophenyl]-4-chloro-5-difluoromethoxy-1-methyl-1H-pyrazole (2.00 g, 5.63 mmol) in tetrahydrofuran was treated with N,N'-carbonyldiimidazole (1.13 g, 6.98 mmol), stirred for 1 hour under reflux, cooled to room temperature, treated with N-methyl-N-isopropylsulfamide (1.10 g, 7.23 mmol), stirred for 10 minutes, treated with diazabicyclo-undecene (1.06 g, 6.97 mmol), stirred overnight at room temperature and concentrated under reduced pressure. Chromatography on silica gel (cyclohexane/ethylacetate=4:1) gave 0.90 g of the raw product. Further crystallization from cyclohexane/ethylacetate (4:1) yielded 0.45 g (16.4%) of the title compound (analyzed by NMR).

$^1$H-NMR (in $CDCl_3$): δ [ppm]=8.8 (s, 1H, NH), 8.0 (d, 1H), 7.3 (d, 1H), 6.7 (t, 1H), 4.3 (hpt, 1H), 3.8 (s, 3H), 3.0 (s, 3H), 1.2 (d, 6H).

Step 1: 2-Chloro-5-[3-chloro-5-(trifluoromethyl)-2-pyridinyl]-4-fluorobenzoic acid 5.3 g (13.4 mmol) of isopropyl ester II with A=O, $X^1$=F, $X^2$=Cl $X^3$=H, Q=$Q^{38}$, $R^{40}$=Cl, $R^{41}$ & $R^{43}$=H and $R^{42}$=$CF_3$, dissolved in 25 ml of glacial acid and 125 ml of concentrated HCl were stirred at 70° C. for 6 hours and at ambient temperature overnight. Then, the reaction mixture was dripped into ice water and the precipiate was filtered off and washed with water. There was obtained 4.1 g as a white solid.

$^1$H-NMR [in $(CD_3)_2SO$]: δ [ppm]=9.1 (s, 1H), 8.7 (s, 1H), 8.1 (d, 1H), 7.8 (d, 1H). {Remark: the exchange of the OH proton for those of water resulted in a broad singulett at 3.3 ppm}.

Step 2: N'-[[(2-Chloro-5-[3-chloro-5-(trifluoromethyl)-2-pyridinyl]-4-fluorobenzoyl]]-N-isopropyl-N-methylsulfamide 1.0 g (2.8 mmol) free acid from step 1 was dissolved in 10 ml of tetrahydrofuran, 0.57 g (3.5 mmol) of carbonyldiimidazole was added and the mixture was heated to 60° C. for 1 hour and cooled to ambient temperature. Then a mixture of 0.55 g (3.6 mmol) of the sulfamide and 0.54 g (3.5 mmol) of 1,8-diazabicyclo[5,4,0]-un-decen-7-ene in 10 ml of tetrahydrofuran was added and stirring was continued at room temperature overnight. The solvent was removed and the crude product was subjected to column chromatography with methyl-tert.-butylether and ethyl acetate. The product-containing fraction was dissolved in methyl-tert.-butylether, washed three times with 10% strength HCl and twice with water and dried over $Na_2SO_4$. Removal of the solvent gave 0.48 g of the title compound as an oil.

$^1$H-NMR [in $(CD_3)_2SO$]: δ [ppm]=9.1 (s, 1 H), 8.7 (s, 1 H), 7.8–7.7 (m, 2 H), 4.1 (m, 1 H), 2.7 (s, 3 H), 1.1 (m 6 H). {Remark: the exchange of the N—H protons for those of water resulted in a broad singulett at 3.3 ppm}.

Example 146

Preparation of 8-(5'-N-Isopropyl-N-methylsulfamoyl-carboxamido-4'-chloro-2'-fluorophenyl)-4-oxo-7,9-dioxo-1,2,8-triaza(4.3.0.)nonane 5.4 g (45.5 mmol) of thionyl chloride was added to a mixture of 12.0 g (36.4 mmol) acid III with $X^1$=F, $X^2$=Cl, Q=$Q^{40}$, $A^{20}$ & $A^{21}$=O, $R^{46}$+$R^{47}$=—$(CH_2)_3$—O—, and 2 drops of pyridine in 200 ml of 1,2-dichloroethane. After 4 hours at 83° C., the volatiles were removed under reduced pressure and the crude acid chloride (12.6 g) was used without further purification:

0.44 g (2.87 mmol) of N-isopropyl-N-methylaminosulfamide in 50 ml of tetrahydrofuran was added to a suspension of 0.07 g of NaH (97% purity) in 50 ml of tetrahydrofuran. After 30 minutes at room temperature, 1.0 g (2.87 mmol) of the crude acid chloride was added and the reaction mixture was stirred overnight at ambient temperature and additionally for 2 hours at 50° C. The solvent was removed under reduced pressure, 1 N HCl and methylene chloride were added and the organic layer was separated. Chromatography on silica-gel gave 0.35 g of the title compound; mp.: 115–120° C.

USE EXAMPLES FOR THE HERBICIDAL ACTIVITY

Example 147

Postemergence herbicidal evaluation of test compounds

The herbicidal activity of the compounds of the present invention was evaluated by the following tests.

Seedling plants were grown in jiffy flats for about two weeks. The test compounds were dispersed in 80/20 acetone/water mixtures containing 1.0% SUN-IT®II, a methylated seed oil, in sufficient quantities to provide the equivalent of about 0.016 to 0.032 kg per hectare of active compound when applied to the plants through a spray nozzle operating at 40 psi for a predetermined time. After spraying, the plants were placed on greenhouse benches and were cared for in accordance with conventional greenhouse Procedures. Approximately two to three weeks after treatment, the seedling plants were examined and rated according to the rating scale (0–9) set forth below. Where more than one test is involved for a given a given compound, the data are averaged. Results obtained are reported in Table I below. Where more than one test is involved for a given compound, the data are averaged.

| HERBICIDE RATING SCALE | |
|---|---|
| Rating | % Control as compared to the untreated check |
| 9 | 100 |
| 8 | 91–99 |
| 7 | 80–90 |
| 6 | 65–79 |
| 5 | 45–64 |
| 4 | 30–44 |
| 3 | 16–29 |
| 2 | 6–15 |
| 1 | 1–5 |
| 0 | 0 |

The scale based upon a visual observation of plant stand, vigor, malformation, size, chlorosis and overall plant appearance as compared with a control.

Plant species employed in these evaluations are reported by header abbreviation, common name and scientific name.

PLANT SPECIES EMPLOYED

| Header abbreviation | Common name | Scientific name |
|---|---|---|
| ABUTH | Velvetleaf | *Abutilon theophrasti,* Medic. |
| AMBEL | Ragweed, Common | *Ambrosia artemiisifolia,* L. |
| CHEAL | Lambsquarters | *Chenopodium album,* L. Common |
| IPOHE | Morningglory, Ivyleaf | *Ipomoea hederacea,* (L)Jacq. |
| XANST | Cocklebur | *Xanthium strumariam* |
| ALOMY | Blackgrass | *Alopecurus myosuroides* |
| DIGSA | Crabgrass, (Hairy) L | *Digitaria sanguinalis,* (L)Scop |
| ECHCG | Barnyardgrass | *Echinochloa crusgalli,* (L.)Beau |
| SETVI | Green foxtail | *Setaria viridis,* (L.)Beau |
| GLXMA | Soybean | *Glycine max,* (L.) Merr. |
| TRZAW | Winter wheat | *Tritium Aestivum,* L. (Winter) |
| ZEAMX | Field corn | *Zea mays* L. |

TABLE A

Postemergence Herbicidal Evaluation

| Ex. No. | Rate [kg/ha] | ABUTH | AMBEL | CHEAL | IPOHE | XANST | ALMOY | DIGSA | ECHCG | SETVI | GLXMA | TRZAW | ZEAMX |
|---|---|---|---|---|---|---|---|---|---|---|---|---|---|
| 53 | 0.032 | 9.0 | 9.0 | 8.4 | 9.0 | 9.0 | 3.0 | 6.6 | 8.8 | 7.5 | 8.4 | 6.2 | 7.6 |
|    | 0.016 | 9.0 | 8.9 | 8.1 | 8.8 | 9.0 | 2.3 | 5.3 | 8.1 | 6.4 | 8.1 | 5.6 | 7.2 |
| 54 | 0.032 | 9.0 | 9.0 | 9.0 | 9.0 | 9.0 | 2.0 | 6.0 | 8.0 | 7.0 | 8.5 | 6.0 | 7.5 |
|    | 0.016 | 9.0 | 9.0 | 9.0 | 9.0 | 9.0 | 2.0 | 5.0 | 6.0 | 7.0 | 8.0 | 5.5 | 6.5 |
| 55 | 0.032 | 9.0 | 9.0 | 7.0 | 9.0 | 8.0 | 2.0 | 6.0 | 7.0 | 8.0 | 8.0 | 6.0 | 8.0 |
|    | 0.016 | 9.0 | 8.0 | 7.0 | 8.0 | 9.0 | 2.0 | 5.0 | 7.0 | 7.0 | 8.0 | 6.0 | 8.0 |
| 56 | 0.032 | 9.0 | 9.0 | 7.0 | 9.0 | 9.0 | 2.0 | 5.0 | 7.0 | 7.0 | 8.5 | 5.0 | 8.0 |
|    | 0.016 | 9.0 | 8.0 | 7.0 | 9.0 | 9.0 | 2.0 | 3.0 | 7.0 | 6.0 | 8.5 | 4.0 | 7.5 |
| 57 | 0.032 | 5.0 | 2.0 | 2.0 | 4.0 | 3.0 | 1.0 | 2.0 | 2.0 | 3.0 | 6.5 | 2.5 | 5.0 |
|    | 0.016 | 2.0 | 1.0 | 1.0 | 6.0 | 2.0 | 0.0 | 1.0 | 1.0 | 1.0 | 6.0 | 2.0 | 2.0 |
| 58 | 0.032 | 9.0 | 9.0 | 9.0 | 9.0 | 9.0 | 3.0 | 6.0 | 7.0 | 8.0 | 8.5 | 5.0 | 8.0 |
|    | 0.016 | 9.0 | 9.0 | 8.0 | 9.0 | 9.0 | 3.0 | 5.0 | 6.0 | 8.0 | 8.5 | 4.5 | 8.0 |
| 59 | 0.032 | 9.0 | 9.0 | 8.0 | 9.0 | 9.0 | 4.0 | 5.0 | 7.0 | 8.0 | 8.5 | 4.5 | 8.0 |
|    | 0.016 | 9.0 | 7.0 | 7.0 | 9.0 | 9.0 | 3.0 | 4.0 | 6.0 | 7.0 | 8.0 | 4.0 | 8.0 |
| 60 | 0.032 | 9.0 | 9.0 | 9.0 | 9.0 | 9.0 | 3.0 | 7.0 | 7.0 | 9.0 | 8.5 | 6.0 | 8.0 |
|    | 0.016 | 9.0 | 9.0 | 8.0 | 9.0 | 9.0 | 3.0 | 6.0 | 8.0 | 8.0 | 8.5 | 6.0 | 8.0 |
| 61 | 0.032 | 9.0 | 9.0 | 8.0 | 9.0 | 9.0 | 1.0 | 6.0 | 8.0 | 9.0 | 8.5 | 6.5 | 7.5 |
|    | 0.016 | 9.0 | 9.0 | 9.0 | 8.0 | 9.0 | 1.0 | 7.0 | 7.0 | 7.0 | 8.5 | 6.0 | 7.5 |
| 62 | 0.032 | 9.0 | 9.0 | 8.0 | 9.0 | 9.0 | 2.0 | 5.0 | 7.0 | 6.0 | 8.0 | 6.5 | 6.5 |
|    | 0.016 | 9.0 | 9.0 | 7.0 | 9.0 | 9.0 | 2.0 | 5.0 | 6.0 | 6.0 | 8.0 | 5.5 | 6.5 |
| 63 | 0.032 | 9.0 | 9.0 | 9.0 | 9.0 | 9.0 | 2.0 | 4.0 | 6.0 | 9.0 | 8.0 | 7.0 | 8.0 |
|    | 0.016 | 9.0 | 9.0 | 7.0 | 9.0 | 9.0 | 2.0 | 4.0 | 4.0 | 7.0 | 8.0 | 6.0 | 7.0 |
| 64 | 0.032 | 9.0 | 9.0 | 9.0 | 9.0 | 9.0 | 5.0 | 5.0 | 9.0 | 9.0 | 8.0 | 7.0 | 8.0 |
|    | 0.016 | 9.0 | 9.0 | 9.0 | 9.0 | 9.0 | 3.0 | 5.0 | 9.0 | 8.0 | 7.5 | 6.0 | 7.5 |
| 65 | 0.032 | 9.0 | 9.0 | 9.0 | 9.0 | 9.0 | 3.0 | 8.0 | 9.0 | 8.0 | 8.5 | 6.5 | 8.0 |
|    | 0.016 | 9.0 | 9.0 | 8.0 | 9.0 | 9.0 | 2.0 | 6.0 | 8.0 | 8.0 | 8.0 | 5.5 | 7.5 |
| 66 | 0.032 | 9.0 | 9.0 | 9.0 | 9.0 | 9.0 | 2.0 | 6.0 | 8.0 | 9.0 | 9.0 | 6.5 | 7.5 |
|    | 0.016 | 9.0 | 9.0 | 8.0 | 9.0 | 9.0 | 1.0 | 5.0 | 8.0 | 8.0 | 8.0 | 5.0 | 7.0 |
| 67 | 0.032 | 9.0 | 9.0 | 9.0 | 9.0 | 9.0 | 3.0 | 6.0 | 8.0 | 8.0 | 8.5 | 7.0 | 7.5 |
|    | 0.016 | 9.0 | 9.0 | 9.0 | 9.0 | 9.0 | 2.0 | 6.0 | 8.0 | 8.0 | 8.0 | 6.5 | 7.5 |
| 68 | 0.032 | 9.0 | 9.0 | 8.0 | 9.0 | 9.0 | 1.0 | 6.0 | 8.0 | 9.0 | 8.5 | 5.5 | 7.5 |
|    | 0.016 | 9.0 | 9.0 | 8.0 | 9.0 | 9.0 | 1.0 | 6.0 | 8.0 | 7.0 | 8.5 | 5.0 | 7.0 |
| 69 | 0.032 | 9.0 | 9.0 | 8.0 | 9.0 | 9.0 | 2.0 | 6.0 | 7.0 | 6.0 | 8.0 | 6.5 | 7.5 |
|    | 0.016 | 9.0 | 9.0 | 8.0 | 9.0 | 9.0 | 1.0 | 4.0 | 5.0 | 5.0 | 8.0 | 5.0 | 7.0 |
| 70 | 0.032 | 9.0 | 7.0 | 7.0 | 9.0 | — | 1.0 | 3.0 | 8.0 | 5.0 | 7.5 | 5.0 | 7.0 |
|    | 0.016 | 9.0 | 5.0 | 6.0 | 9.0 | — | 1.0 | 2.0 | 4.0 | 4.0 | 6.5 | 4.5 | 7.0 |
| 71 | 0.032 | 9.0 | 9.0 | 5.0 | 9.0 | — | 1.0 | 3.0 | 3.0 | 5.0 | 8.0 | 4.5 | 6.5 |
|    | 0.016 | 9.0 | 6.0 | 5.0 | 8.0 | — | 1.0 | 2.0 | 2.0 | 4.0 | 8.0 | 4.5 | 6.5 |
| 72 | 0.032 | 9.0 | 9.0 | 8.0 | 9.0 | — | 2.0 | 4.0 | 8.0 | 6.0 | 8.5 | 6.5 | 7.0 |
|    | 0.016 | 9.0 | 9.0 | 8.0 | 9.0 | — | 1.0 | 4.0 | 6.0 | 5.0 | 8.5 | 5.5 | 7.0 |
| 73 | 0.032 | 9.0 | 9.0 | 9.0 | 9.0 | — | 3.0 | 6.0 | 7.0 | 5.0 | 8.5 | 6.5 | 7.5 |

TABLE A-continued

Postemergence Herbicidal Evaluation

| Ex. No. | Rate [kg/ha] | ABUTH | AMBEL | CHEAL | IPOHE | XANST | ALMOY | DIGSA | ECHCG | SETVI | GLXMA | TRZAW | ZEAMX |
|---|---|---|---|---|---|---|---|---|---|---|---|---|---|
|  | 0.016 | 9.0 | 9.0 | 8.0 | 9.0 | — | 2.0 | 4.0 | 4.0 | 4.0 | 8.5 | 5.5 | 7.0 |
| 76 | 0.032 | 9.0 | 8.0 | 6.0 | 9.0 | 9.0 | 1.0 | 4.0 | 6.0 | 6.0 | 7.5 | 6.0 | 6.5 |
|  | 0.016 | 9.0 | 8.0 | 6.0 | 9.0 | 9.0 | 1.0 | 3.0 | 5.0 | 5.0 | 7.5 | 5.0 | 5.5 |
| 77 | 0.032 | 9.0 | 8.0 | 7.0 | 9.0 | 9.0 | 1.0 | 4.0 | 6.0 | 6.0 | 7.5 | 5.0 | 6.5 |
|  | 0.016 | 9.0 | 8.0 | 6.0 | 9.0 | 9.0 | 1.0 | 4.0 | 4.0 | 5.0 | 7.5 | 4.5 | 6.0 |
| 78 | 0.032 | 9.0 | 9.0 | 9.0 | 9.0 | 9.0 | 2.0 | 6.0 | 9.0 | 9.0 | 8.0 | 6.5 | 7.0 |
|  | 0.016 | 9.0 | 9.0 | 7.0 | 9.0 | 9.0 | 2.0 | 5.0 | 8.0 | 8.0 | 7.0 | 5.5 | 6.5 |
| 80 | 0.032 | 9.0 | 8.0 | 4.0 | 9.0 | 9.0 | 1.0 | 4.0 | 6.0 | 6.0 | 8.0 | 4.0 | 4.0 |
|  | 0.016 | 7.0 | 7.0 | 3.0 | 9.0 | 8.0 | 0.0 | 3.0 | 4.0 | 5.0 | 8.0 | 3.0 | 1.5 |
| 82 | 0.032 | 9.0 | 9.0 | 9.0 | 9.0 | 9.0 | 2.0 | 3.0 | 8.0 | 7.0 | 8.5 | 6.0 | 6.5 |
|  | 0.016 | 9.0 | 9.0 | 9.0 | 9.0 | 9.0 | 1.0 | 3.0 | 7.0 | 6.0 | 8.0 | 5.5 | 6.5 |
| 83 | 0.032 | 9.0 | 8.0 | 5.0 | 9.0 | 9.0 | 1.0 | 4.0 | 8.0 | 8.0 | 7.5 | 5.5 | 6.0 |
|  | 0.016 | 9.0 | 6.0 | 5.0 | 8.0 | 9.0 | 0.0 | 3.0 | 8.0 | 7.0 | 7.0 | 4.5 | 5.5 |
| 84 | 0.032 | 9.0 | 9.0 | 9.0 | 9.0 | 9.0 | 2.0 | 6.0 | 9.0 | 8.0 | 8.5 | 5.5 | 8.0 |
|  | 0.016 | 9.0 | 8.0 | 7.0 | 9.0 | 9.0 | 1.0 | 5.0 | 8.0 | 7.0 | 7.0 | 5.0 | 7.0 |

Example 148

Preemergence herbicidal evaluation Of test compounds

The herbicidal activity of the compounds of the present invention was evaluated by the following tests wherein the seeds of a variety of monocotyledonous and dicotyledonous plants were separately mixed with potting soil and planted on top of approximately one inch of soil in separate pint cups. After planting, the cups were sprayed with the selected aqueous acetone solution containing test compound in sufficient quantity to provide the equivalent of about 0.125 to 0.250 kg per hectare of test compound per cup. The treated cups were then placed on greenhouse benches, watered and cared for in accordance with conventional greenhouse procedures. From two to four weeks after treatment, the tests were terminated and each cup was examined and rated according to the rating system provided in Example 94. When more than one test was performed for a given compound, the data were averaged. The results obtained are shown in Table B.

TABLE B

Preemergence Herbicidal Evaluation

| Ex. No. | Rate [kg/ha] | ABUTH | AMBEL | CHEAL | IPOHE | XANST | ALMOY | DIGSA | ECHCG | SETVI | GLXMA | TRZAW | ZEAMX |
|---|---|---|---|---|---|---|---|---|---|---|---|---|---|
| 53 | 0.25 | 9.0 | 9.0 | 9.0 | 9.0 | 9.0 | 2.7 | 8.8 | 8.4 | 7.3 | 8.8 | 2.0 | 4.3 |
|  | 0.125 | 9.0 | 8.9 | 9.0 | 9.0 | 9.0 | 1.3 | 8.1 | 7.5 | 5.7 | 8.1 | 1.3 | 2.3 |
| 54 | 0.25 | 9.0 | 8.0 | 9.0 | 1.0 | 3.0 | 0.0 | 6.0 | 3.0 | 3.0 | 0.0 | 0.0 | 0.0 |
|  | 0.125 | 9.0 | 7.0 | 9.0 | 0.0 | 1.0 | 0.0 | 4.0 | 3.0 | 2.0 | 0.0 | 0.0 | 0.0 |
| 55 | 0.25 | 9.0 | 9.0 | 9.0 | 9.0 | 7.0 | 0.0 | 8.0 | 9.0 | 8.0 | 8.0 | 2.0 | 1.0 |
|  | 0.125 | 9.0 | 8.0 | 8.0 | 8.0 | 6.0 | 0.0 | 8.0 | 5.0 | 6.0 | 8.0 | 1.0 | 0.0 |
| 56 | 0.25 | 9.0 | 9.0 | 9.0 | 9.0 | 9.0 | 0.0 | 7.0 | 7.0 | 8.0 | 9.0 | 0.0 | 2.0 |
|  | 0.125 | 9.0 | 9.0 | 9.0 | 8.0 | 8.0 | 0.0 | 7.0 | 3.0 | 4.0 | 2.0 | 0.0 | 0.0 |
| 57 | 0.25 | 2.0 | 2.0 | 8.0 | 3.0 | 0.0 | 0.0 | 3.0 | 2.0 | 1.0 | 1.0 | 0.0 | 0.0 |
|  | 0.125 | 2.0 | 2.0 | 6.0 | 0.0 | 0.0 | 0.0 | 1.0 | 1.0 | 0.0 | 0.0 | 0.0 | 0.0 |
| 58 | 0.25 | 9.0 | 9.0 | 9.0 | 9.0 | 8.0 | 0.0 | 3.0 | 6.0 | 6.0 | 9.0 | 3.0 | 1.0 |
|  | 0.125 | 9.0 | 9.0 | 9.0 | 9.0 | 5.0 | 0.0 | 0.0 | 4.0 | 2.0 | 9.0 | 0.0 | 0.0 |
| 59 | 0.25 | 9.0 | 9.0 | 9.0 | 9.0 | 9.0 | 4.0 | 7.0 | 3.0 | 9.0 | 8.0 | 0.0 | 2.0 |
|  | 0.125 | 9.0 | 9.0 | 9.0 | 9.0 | 0.0 | 0.0 | 3.0 | 0.0 | 4.0 | 2.0 | 0.0 | 0.0 |
| 60 | 0.25 | 9.0 | 9.0 | 9.0 | 6.0 | 4.0 | 0.0 | 6.0 | 4.0 | 9.0 | 6.0 | 0.0 | 0.0 |
|  | 0.125 | 9.0 | 9.0 | 9.0 | 7.0 | 0.0 | 0.0 | 6.0 | 0.0 | 5.0 | 0.0 | 0.0 | 0.0 |
| 61 | 0.25 | 9.0 | 9.0 | 9.0 | 9.0 | 9.0 | 0.0 | 9.0 | 7.0 | 6.0 | 9.0 | 3.0 | 2.0 |
|  | 0.125 | 9.0 | 9.0 | 9.0 | 9.0 | 9.0 | 0.0 | 6.0 | 4.0 | 3.0 | 9.0 | 2.0 | 2.0 |
| 62 | 0.25 | 9.0 | 9.0 | 9.0 | 9.0 | 9.0 | 0.0 | 7.0 | 6.0 | 7.0 | 9.0 | 5.0 | 1.0 |
|  | 0.125 | 9.0 | 9.0 | 9.0 | 9.0 | 9.0 | 0.0 | 5.0 | 3.0 | 3.0 | 5.0 | 3.0 | 1.0 |
| 63 | 0.25 | 9.0 | 9.0 | 9.0 | 9.0 | — | 0.0 | 8.0 | 9.0 | 8.0 | 5.0 | 0.0 | 0.0 |
|  | 0.125 | 9.0 | 9.0 | 9.0 | 9.0 | — | 0.0 | 3.0 | 4.0 | 4.0 | 1.0 | 0.0 | 0.0 |
| 64 | 0.25 | 9.0 | 9.0 | 9.0 | 9.0 | — | 4.0 | 9.0 | 7.0 | 9.0 | — | 3.0 | 2.0 |
|  | 0.125 | 9.0 | 9.0 | 9.0 | 9.0 | — | 0.0 | 8.0 | 3.0 | 8.0 | — | 0.0 | 0.0 |
| 65 | 0.25 | 9.0 | 9.0 | 9.0 | 9.0 | — | 0.0 | 9.0 | 9.0 | 6.0 | — | 1.0 | 1.0 |
|  | 0.125 | 9.0 | 9.0 | 9.0 | 9.0 | — | 0.0 | 7.0 | 8.0 | 3.0 | — | 1.0 | 0.0 |
| 66 | 0.25 | 9.0 | 9.0 | 9.0 | 9.0 | — | 2.0 | 8.0 | 8.0 | 6.0 | — | 1.0 | 2.0 |
|  | 0.125 | 9.0 | 9.0 | 9.0 | 9.0 | — | 0.0 | 4.0 | 4.0 | 4.0 | 0.0 | 1.0 | 1.0 |
| 67 | 0.25 | 9.0 | 7.0 | 9.0 | 9.0 | — | 0.0 | 8.0 | 9.0 | 8.0 |  | 1.0 | 1.0 |
|  | 0.125 | 9.0 | 9.0 | 9.0 | 9.0 | — | 0.0 | 7.0 | 8.0 | 8.0 |  | 0.0 | 0.0 |
| 68 | 0.25 | 9.0 | 9.0 | 8.0 | 9.0 | 9.0 | 0.0 | 4.0 | 4.0 | 8.0 | 8.0 | 0.0 | 2.0 |
|  | 0.125 | 9.0 | 9.0 | 8.0 | 9.0 | 9.0 | 0.0 | 3.0 | 3.0 | 4.0 | 7.0 | 0.0 | 1.0 |

TABLE B-continued

Preemergence Herbicidal Evaluation

| Ex. No. | Rate [kg/ha] | ABUTH | AMBEL | CHEAL | IPOHE | XANST | ALMOY | DIGSA | ECHCG | SETVI | GLXMA | TRZAW | ZEAMX |
|---|---|---|---|---|---|---|---|---|---|---|---|---|---|
| 69 | 0.25 | 9.0 | 9.0 | 9.0 | 9.0 | 4.0 | 0.0 | 3.0 | 3.0 | 1.0 | 3.0 | 0.0 | 3.0 |
|  | 0.125 | 9.0 | 8.0 | 9.0 | 9.0 | 3.0 | 0.0 | 3.0 | 2.0 | 0.0 | 0.0 | 0.0 | 2.0 |
| 70 | 0.25 | 9.0 | 9.0 | 9.0 | 9.0 | 9.0 | 0.0 | 5.0 | 7.0 | 5.0 | 3.0 | 1.0 | 0.0 |
|  | 0.125 | 9.0 | 9.0 | 8.0 | 9.0 | 8.0 | 0.0 | 2.0 | 2.0 | 3.0 | 1.0 | 0.0 | 0.0 |
| 71 | 0.25 | 9.0 | 8.0 | 7.0 | 9.0 | 7.0 | 0.0 | 3.0 | 3.0 | 2.0 | 2.0 | 0.0 | 1.0 |
|  | 0.125 | 9.0 | 8.0 | 9.0 | 9.0 | 0.0 | 0.0 | 0.0 | 0.0 | 0.0 | 0.0 | 0.0 | 0.0 |
| 72 | 0.25 | 9.0 | 9.0 | 9.0 | 9.0 | 9.0 | 2.0 | 7.0 | 6.0 | 8.0 | 9.0 | 1.0 | 0.0 |
|  | 0.125 | 9.0 | 9.0 | 9.0 | 9.0 | 7.0 | 1.0 | 2.0 | 7.0 | 4.0 | 8.0 | 0.0 | 0.0 |
| 73 | 0.25 | 9.0 | 9.0 | 9.0 | 9.0 | 9.0 | 0.0 | 3.0 | 3.0 | 5.0 | 0.0 | 0.0 | 0.0 |
|  | 0.125 | 9.0 | 9.0 | 9.0 | 9.0 | 3.0 | 0.0 | 3.0 | 0.0 | 2.0 | 0.0 | 0.0 | 0.0 |
| 76 | 0.25 | 9.0 | 9.0 | 9.0 | 9.0 | 5.0 | 2.0 | 3.0 | 2.0 | 2.0 | 3.0 | 1.0 | 1.0 |
|  | 0.125 | 9.0 | 8.0 | 8.0 | 5.0 | 3.0 | 0.0 | 2.0 | 1.0 | 1.0 | 1.0 | 0.0 | 1.0 |
| 77 | 0.25 | 9.0 | 9.0 | 9.0 | 9.0 | 8.0 | 0.0 | 4.0 | 3.0 | 2.0 | — | 0.0 | 1.0 |
|  | 0.125 | 9.0 | 9.0 | 9.0 | 7.0 | 3.0 | 0.0 | 2.0 | 2.0 | 2.0 | 1.0 | 0.0 | 0.0 |
| 78 | 0.25 | 9.0 | 9.0 | 9.0 | 9.0 | 9.0 | 2.0 | 8.0 | 7.0 | 7.0 | 5.0 | 1.0 | 1.0 |
|  | 0.125 | 9.0 | 9.0 | 9.0 | 9.0 | 9.0 | 1.0 | 4.0 | 4.0 | 5.0 | 3.0 | 1.0 | 0.0 |
| 80 | 0.25 | 5.0 | 3.0 | 8.0 | 0.0 | 1.0 | 0.0 | 1.0 | 3.0 | 0.0 | 0.0 | 0.0 | 0.0 |
|  | 0.125 | 1.0 | 1.0 | 5.0 | 0.0 | 0.0 | 0.0 | 0.0 | 0.0 | 0.0 | 0.0 | 0.0 | 0.0 |
| 82 | 0.25 | 9.0 | 9.0 | 9.0 | 9.0 | 9.0 | 0.0 | 4.0 | 4.0 | 7.0 | 9.0 | 1.0 | 2.0 |
|  | 0.125 | 9.0 | 9.0 | 9.0 | 9.0 | 9.0 | 0.0 | 4.0 | 3.0 | 3.0 | 9.0 | 0.0 | 0.0 |
| 83 | 0.25 | 9.0 | 8.0 | 9.0 | 8.0 | 5.0 | 0.0 | 9.0 | 5.0 | 6.0 | 4.0 | 0.0 | 2.0 |
|  | 0.125 | 8.0 | 8.0 | 9.0 | 7.0 | 4.0 | 0.0 | 1.0 | 4.0 | 3.0 | 1.0 | 0.0 | 0.0 |
| 84 | 0.25 | 9.0 | 9.0 | 9.0 | 9.0 | 9.0 | 1.0 | 8.0 | 6.0 | 7.0 | 7.0 | 2.0 | 1.0 |
|  | 0.125 | 9.0 | 9.0 | 9.0 | 9.0 | 9.0 | 0.0 | 7.0 | 5.0 | 7.0 | 2.0 | 0.0 | 0.0 |

Example 149

The herbicidal action of the uracil substituted phenyl sulfamoyl carboxamides no. Ij.86, Ip.86 and Iy.86 was demonstrated by the following greenhouse experiments:

The culture containers used were plastic flowerpots containing loamy sand with approximately 3.01 of humus as substrate. The seeds of the test plants were sown separately for each species.

For the post-emergence treatment, the test plants were grown to a plant height of from 3 to 15 cm, depending on the plant habit, and only then treated with the active ingredients which had been suspended or emulsified in water. To this end, the test plants were either sown directly and grown in the same containers, or they were first grown separately as seedlings and transplanted into the test containers a few days prior to treatment. The rate of application for the post-emergence treatment was 15.6 or 7.8 g/ha active ingredient.

Depending on the species, the plants were kept at from 10–25° C. and 20–35° C., respectively. The test period extended over 2 to 4 weeks. During this time, the plants were tended, and their response to the individual treatments was evaluated.

Evaluation was carried out using a scale of from 0 to 100. 100 means no emergence of the plants, or complete destruction of at least the aerial parts, and 0 means no damage or normal course of growth.

The plants used in the greenhouse experiments belonged to the following species:

| Scientific Name | Common Name |
|---|---|
| *Amaranthus retroflexus* (AMARE) | Redroot pigweed |
| *Pharbitis purpurea* (PHBPU) | common or tall morningglory |
| *Polygonum persicaria* (POLPE) | redshank; ladysthumb |

At a rate of application of 15.6 or 7.8 g/ha of a.i., compound nos. Ij.86, Ip.86 and Iy.86 showed a very good herbicial action against the abovementioned undesired plants.

Desiccant/Defoliant Activity of the Compounds I

Example 150

Greenhouse-Trials

The test plants used were young cotton plants with 4 leaves (without cotyledons) which had been grown under greenhouse conditions (relative atmospheric humidity 50 to 70%; day/night temperature 27/20° C.).

The young cotton plants were subjected to foliar treatment to run-off point with aqueous preparations of the active ingredients (with an addition of 0.15% by weight of the fatty alcohol alkoxylate Plurafac® LF 700[1]), based on the spray mixture). The amount of water applied was 1000 l/ha (converted). After 13 days, the number of leaves shed and the degree of defoliation in % were determined.

No leaves were shed in the untreated control plants.
1) a low-foam, nonionic surfactant from BASF AG

Example 151

Field Trials

Field evaluations of preharvest desiccant activity were performed at several different locations using compound Ia.86.

In each experiment treatments wag replicated three times in a randomized complete block experimental design. Potatoes were grown using good agronomic practices of each area. Treatments were applied a few weeks before planned potato harvest.

The test compound was formulated as an emulsifiable concentrate (EC) formulation with 120 grams a.i./liter. The formulation was diluted with water, spray adjuvants were added, and the treatment solution was applied to the foliage of potatoes in from 187 to 600 l/ha of total spray volume. Unless indicated otherwise, the treatments also contained 15 v/v of methylated seed oil adjuvant (Hasten or SUN-IT II. In the case of split applications, the second application was made about 1 week after the initial application.

At various intervals after treatment, desiccation of stems and leaves was evaluated separately, on a visual % desiccation scale. In each test the test compound was compared to appropriate commercial standards at the normal rate for each standard for the area.

The results showed that the abovementioned compound is very effective to desiccate the leaves and stems of potato plants.

What is claimed is:

1. A compound of formula I

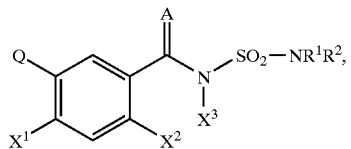

wherein the variables have the following meanings:

A oxygen or sulfur;

$X^1$ hydrogen, halogen or $C_1$–$C_4$-alkyl;

$X^2$ hydrogen, cyano, CS—$NH_2$, halogen, $C_1$–$C_4$-alkyl or $C_1$–$C_4$-haloalkyl;

$X^3$ hydrogen, cyano, $C_1$–$C_6$-alkyl, $C_1$–$C_6$-alkoxy-alkyl, $C_3$–$C_7$-cycloalkyl, $C_3$–$C_6$-alkenyl, $C_3$–$C_6$-alkynyl or optionally substituted benzyl;

$R^1$ and $R^2$ independently of one another hydrogen, halogen, $OR^{48}$, $C_1$–$C_{10}$-alkyl, $C_2$–$C_{10}$-alkenyl, $C_3$–$C_{10}$-alkynyl, $C_3$–$C_7$-cycloalkyl, phenyl, benzyl or $C_5$–$C_7$-cycloalkenyl, whereas each of the lastmentioned 7 groups can be substituted with any combination of one to six halogen atoms, one to three $C_1$–$C_6$-alkoxy groups, one or two $C_1$–$C_8$-haloalkoxy groups, one or two cyano groups, one or two $C_3$–$C_7$-cycloalkyl groups, one or two $C(O)R^{49}$ groups, one or two CO—$OR^{50}$ groups, one or two CO—$SR^{51}$ groups, one or two CO—$NR^{52}R^{53}$ groups, one to three $OR^{54}$ groups, one to three $SR^{54}$ groups, one optionally substituted four to 10-membered monocyclic or fused bicyclic heterocyclic ring, one or two optionally substituted phenyl groups or one or two optionally substituted benzyl groups, or $R^1$ and $R^2$ together with the atom to which they are attached form a 3- to 7-membered heterocyclic ring;

Q is selected from

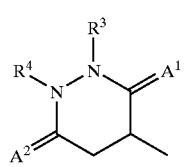

Q⁶

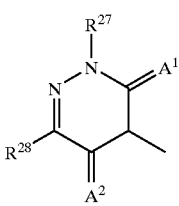

Q²⁰

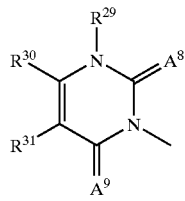

Q²¹

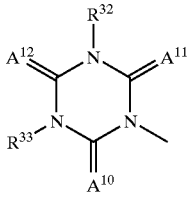

Q²²

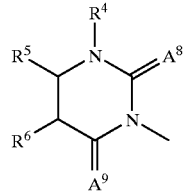

Q²³

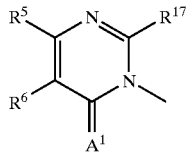

Q²⁴

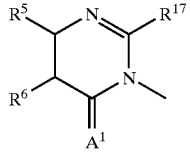

Q²⁵

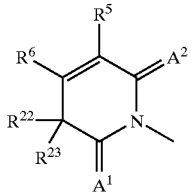

Q²⁶

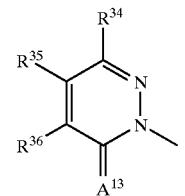

Q²⁷

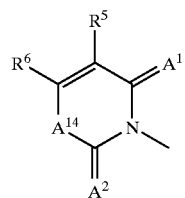

Q²⁹

-continued

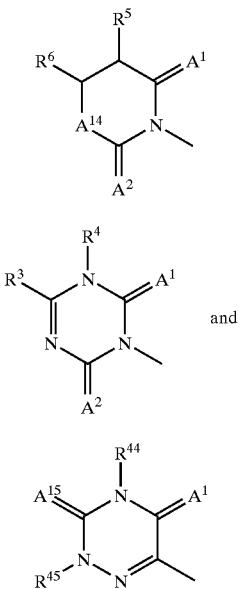

wherein
- $A^1$, $A^2$ and $A^8$ to $A^{15}$ are each independently oxygen or sulfur;
- $R^3$, $R^4$, $R^{27}$, $R^{29}$, $R^{32}$, $R^{33}$, $R^{44}$ and $R^{45}$ are each independently
  hydrogen, cyano, amino, $C_1$–$C_6$-alkyl, $C_1$–$C_6$-haloalkyl, $C_1$–$C_6$-haloalkoxy, $C_3$–$C_7$-cycloalkyl, $C_2$–$C_6$-alkenyl, $C_2$–$C_6$-haloalkenyl, $C_3$–$C_6$-alkynyl, benzyl, $OR^{55}$, $C_1$–$C_3$-cyanoalkyl, or
- $R^3$ and $R^4$ together with the atoms to which they are attached to represent a four- to seven-membered ring, optionally interrupted by oxygen, sulfur or nitrogen and optionally substituted with one or more halogen or $C_1$–$C_4$-alkyl groups;
- $R^5$, $R^6$, $R^{30}$, $R^{31}$, $R^{35}$ and $R^{36}$, are each independently
  hydrogen, $C_1$–$C_6$-alkyl, $C_1$–$C_6$-haloalkyl, $C_3$–$C_7$-cycloalkyl, $C_2$–$C_6$-alkenyl, $C_2$–$C_6$-haloalkenyl, $C_3$–$C_6$-alkynyl, $OR^{56}$, $S(O)_nR^{57}$, $O$—$SO_2$—$R^{57}$, $NR^{58}R^{59}$ or
- $R^5$ and $R^6$ or $R^{30}$ and $R^{31}$ together with the atoms to which they are attached to represent a four- to seven membered ring optionally substituted with one or more halogen or $C_1$–$C_4$-alkyl groups;
- $R^{22}$ and $R^{23}$ are each independently hydrogen, halogen or $C_1$–$C_6$-alkyl;
- $R^{17}$, $R^{28}$ and $R^{34}$, are each independently hydrogen, halogen, $C_1$–$C_6$-alkyl, $C_1$–$C_6$-haloalkyl, $C_3$–$C_7$-cycloalkyl, $C_2$–$C_6$-alkenyl, $C_2$–$C_6$-haloalkenyl, $C_3$–$C_6$-alkynyl, $OR^{60}$ or $SR^{61}$;
- $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$ and $R^{61}$ are independently of one another
  hydrogen, $C_1$–$C_6$-alkyl, $C_1$–$C_6$-haloalkyl, $C_3$–$C_7$-cycloalkyl, $C_2$–$C_6$-alkenyl, $C_3$–$C_6$-alkynyl, optionally substituted phenyl or optionally substituted benzyl;
- n is zero, 1 or 2;
or an agriculturally useful salt thereof.

2. The compound defined in claim 1, wherein Q is selected from $Q^{21}$, $Q^{22}$, $Q^{27}$ and $Q^{39}$.

3. A herbicidal composition, comprising a herbicidally effective amount of at least one compound of formula I as defined in claim 1 or of an agriculturally useful salt thereof, and at least one inert liquid or solid carrier and optionally at least one surfactant.

4. A composition for the desiccation or defoliation of plants, comprising an effective amount of at least one compound of formula I as defined in claim 1 or of an agriculturally useful salt thereof, and at least one inert liquid or solid carrier and optionally at least one surfactant.

5. A method of controlling undesirable vegetation, which comprises treating the vegetation or its environment or seed with an effective amount of at least one compound of formula I as defined in claim 1 or of an agriculturally useful salt thereof.

6. A method for desiccation or defoliation of plants, which comprises treating the plants with an effective amount of at least one compound of formula I as defined in claim 1 or an agriculturally useful salt thereof.

7. The method of claim 6, wherein the treated plants are cotton plants.

8. A process for the preparation of the compound of formula I as defined in claim 1, which process comprises reacting a benzoic acid derivative of formula II

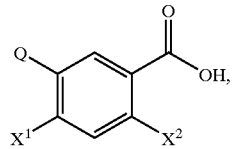

II optionally in the presence of a coupling agent, or the corresponding acid chloride of II, with a sulfamide of formula III

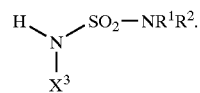

III

9. A process for the preparation of the compound of formula I as defined in claim 1, where A is oxygen, $X^3$ is hydrogen, Q is $Q^{21}$, $A^8$ and $A^9$ are oxygen and $R^{29}$ is hydrogen,
which process comprises reacting an aniline intermediate VI

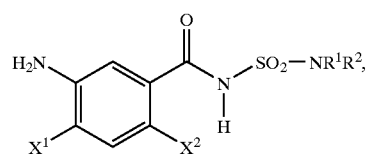

VI with an oxazinone compound of the formula VII

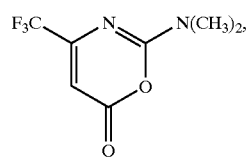

VII optionally followed by alkylation and hydrolysis.

10. A process for the preparation of a compound of formula VI

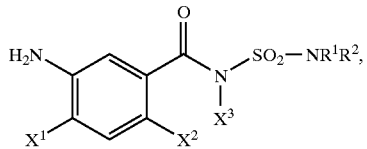

wherein
  $X^1$ is hydrogen, halogen or $C_1$–$C_4$-alkyl;
  $X^2$ is hydrogen, cyano, CS—$NH_2$, halogen, $C_1$–$C_4$-alkyl or $C_1$–$C_4$-haloalkyl;
  $X^3$ is hydrogen, cyano, $C_1$–$C_6$-alkyl, $C_1$–$C_6$-alkoxy-alkyl, $C_3$–$C_7$-cycloalkyl, $C_3$–$C_6$-alkenyl, $C_3$–$C_6$-alkynyl or optionally substituted benzyl; and
  $R^1$ and $R^2$ independently of one another
    hydrogen, halogen, $OR^{48}$, $C_1$–$C_{10}$-alkyl, $C_2$–$C_{10}$-alkenyl, $C_3$–$C_{10}$-alkynyl, $C_3$–$C_7$-cycloalkyl, phenyl, benzyl or $C_5$–$C_7$-cycloalkenyl, whereas each of the lastmentioned 7 groups can be substituted with any combination of one to six halogen atoms, one to three $C_1$–$C_6$-alkoxy groups, one or two $C_1$–$C_8$-haloalkoxy groups, one or two cyano groups, one or two $C_3$–$C_7$-cycloalkyl groups, one or two $C(O)R^{49}$ groups, one or two CO—$OR^{50}$ groups, one or two CO—$SR^{51}$ groups, one or two CO—$NR^{52}R^{53}$ groups, one to three $OR^{54}$ groups, one to three $SR^{54}$ groups, one optionally substituted four to 10-membered monocyclic or fused bicyclic heterocyclic ring, one or two optionally substituted phenyl groups or one or two optionally substituted benzyl groups, or
  $R^1$ and $R^2$ together with the atom to which they are attached form a 3- to 7-membered heterocyclic ring;
  $R^{48}$, $R^{49}$, $R^{50}$, $R^{51}$, $R^{52}$, $R^{53}$ and $R^{54}$ are independently of one another
    hydrogen, $C_1$–$C_6$-alkyl, $C_1$–$C_6$-haloalkyl, $C_3$–$C_7$-cycloalkyl, $C_2$–$C_6$-alkenyl, $C_3$–$C_6$-alkynyl, optionally substituted phenyl or optionally substituted benzyl;
which process comprises treating a sulfamoyl carboxamide X

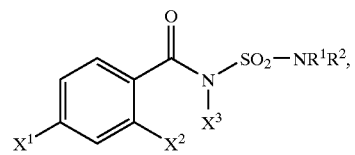

with a nitration reagent to give the corresponding nitrated compound XI

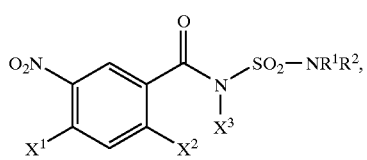

and subsequently reducing the nitro group with a transition metal under acidic conditions or with a complex hydride.

11. A process for the preparation of a sulfamoyl carboxamide X

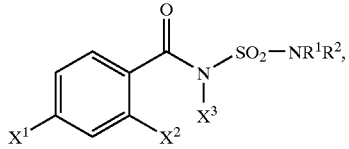

wherein
  $X^1$ is hydrogen, halogen or $C_1$–$C_4$-alkyl;
  $X^2$ is hydrogen, cyano, CS—$NH_2$, halogen, $C_1$–$C_4$-alkyl or $C_1$–$C_4$-haloalkyl;
  $X^3$ is hydrogen, cyano, $C_1$–$C_6$-alkyl, $C_1$–$C_6$-alkoxy-alkyl, $C_3$–$C_7$-cycloalkyl, $C_3$–$C_6$-alkenyl, $C_3$–$C_6$-alkynyl or optionally substituted benzyl; and
  $R^1$ and $R^2$ independently of one another
    hydrogen, halogen, $OR^{48}$, $C_1$–$C_{10}$-alkyl, $C_2$–$C_{10}$-alkenyl, $C_3$–$C_{10}$-alkynyl, $C_3$–$C_7$-cycloalkyl, phenyl, benzyl or $C_5$–$C_7$-cycloalkenyl, whereas each of the lastmentioned 7 groups can be substituted with any combination of one to six halogen atoms, one to three $C_1$–$C_6$-alkoxy groups, one or two $C_1$–$C_8$-haloalkoxy groups, one or two cyano groups, one or two $C_1$–$C_8$-cycloalkyl groups, one or two $C(O)R^{49}$ groups, one or two CO—$OR^{50}$ groups, one or two CO—$SR^{51}$ groups, one or two CO—$NR^{52}R^{53}$ groups, one to three $OR^{54}$ groups, one to three $SR^{54}$ groups, one optionally substituted four to 10-membered monocyclic or fused bicyclic heterocyclic ring, one or two optionally substituted phenyl groups or one or two optionally substituted benzyl groups, or
  $R^1$ and $R^2$ together with the atom to which they are attached form a 3- to 7-membered heterocyclic ring;
  $R^{48}$, $R^{49}$, $R^{50}$, $R^{51}$, $R^{52}$, $R^{53}$ and $R^{54}$ are independently of one another
    hydrogen, $C_1$–$C_6$-alkyl, $C_1$–$C_6$-haloalkyl, $C_3$–$C_7$-cycloalkyl, $C_2$–$C_6$-alkenyl, $C_3$–$C_6$-alkynyl, optionally substituted phenyl or optionally substituted benzyl;
which process comprises reacting a benzoic acid IX

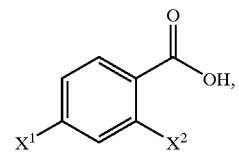

optionally in the presence of a coupling agent, or the corresponding acid chloride of IX, with a sulfamide of the formula III

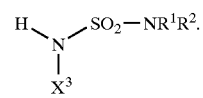

12. The method according to claim 5 wherein the compound is applied in the presence of a crop.

13. The method according to claim 12 wherein the crop is a cereal crop or a leguminous crop.

14. The method according to claim 13 wherein the crop is corn, wheat or rice.

* * * * *

UNITED STATES PATENT AND TRADEMARK OFFICE
CERTIFICATE OF CORRECTION

PATENT NO. : 6,849,618 B2
APPLICATION NO. : 10/684940
DATED : February 1, 2005
INVENTOR(S) : Carlsen et al.

Page 1 of 1

It is certified that error appears in the above-identified patent and that said Letters Patent is hereby corrected as shown below:

Claim 10: Column 65, line 16, "$Ci_1$-$C_6$-alkyl" should read --$C_1$-$C_6$-alkyl--

Claim 11: Column 66, line 26, "$C_1$-$C_8$-cycloalkyl" should read --$C_3$-$C_7$-cycloalkyl--

Signed and Sealed this

Third Day of April, 2007

JON W. DUDAS
*Director of the United States Patent and Trademark Office*